(12) United States Patent
Cohen et al.

(10) Patent No.: US 7,083,511 B1
(45) Date of Patent: Aug. 1, 2006

(54) METHODS

(75) Inventors: Philip Cohen, Dundee (GB); Takayasu Kobayashi, Dundee (GB); Maria Deak, Dundee (GB)

(73) Assignee: The University of Dundee, Dundee (GB)

( * ) Notice: Subject to any disclaimer, the term of this patent is extended or adjusted under 35 U.S.C. 154(b) by 0 days.

(21) Appl. No.: 09/868,131

(22) PCT Filed: Dec. 14, 1999

(86) PCT No.: PCT/GB99/04232

§ 371 (c)(1),
(2), (4) Date: Apr. 11, 2002

(87) PCT Pub. No.: WO00/35940

PCT Pub. Date: Jun. 22, 2000

Related U.S. Application Data

(60) Provisional application No. 60/112,217, filed on Dec. 14, 1998.

(30) Foreign Application Priority Data

Aug. 19, 1999 (GB) ................................. 9919676.8

(51) Int. Cl.
*C12Q 1/48* (2006.01)
*C12N 9/12* (2006.01)
*C12N 1/20* (2006.01)
*C07H 21/04* (2006.01)

(52) U.S. Cl. ........................ 453/15; 435/194; 530/300; 530/350; 536/23.2

(58) Field of Classification Search .................. 435/15, 435/194; 530/350, 300; 536/23.2
See application file for complete search history.

(56) References Cited

OTHER PUBLICATIONS

Webster et al Characterization of sgk, a novel member of the serine/threonine protein kinase gene family which is transcriptionally induced by glucocorticoids and serum. Mol Cell Biol. Apr. 1993; 13(4):2031-40.*
Accession No. Y10032.*
Waldegger et al.PNAS, USA., 94(9): 4440-4445 (1997).*
Alessi et al. Current Biology 1997, 8: 69-81.*
Waldegger et al., Pflugers Arch Eur J. Physiol, 436:575-580(1998).
Kobayashi et al., Biochem. J., 344:189-197(1999).
Kobayashi et al., Biochem J., 339:319-328(1999).
Webster et al., Mol. Cell. Biol., 13(4):2031-2040(1993).
Dutil et al., Curr. Biol., 8:1366-1375(1998).
Le Good, Science, 281:2042-2045(1998).
Alessi et al., Curr. Biol., 7:776-789(1997).
Webster et al., J. Biol.. Chem., 268:11482-11485(1993).
Hollister et al., Neurosci Lett., 79:1111-1119(1997).
Imaizumi et al., Mol. Brain Res., 26:189-196(1994).
Maiyar et al., J. Biol. Chem., 271:12414-12422(1996).
Maiyar et al., Mol. Endocrinol., 11(3):312-329(1997).
Pearson et al., EMBO J., 14: 5279-5287(1995).
Cross et al., Nature, 378:785-789(1995).
Genbank Accession Y10032.
Genbank Accession L01624.
AA130828(IMAGE Consortium, St Louis, MO.
AI386362.
AA790370.
AA138663.
AA219166.
Richards et al., Hormone Res., 50:223-255(1995).

* cited by examiner

*Primary Examiner*—Tekchand Saidha
(74) *Attorney, Agent, or Firm*—Rogalskyj & Weyand, LLP

(57) ABSTRACT

A method of activating serum and glucocorticoid-induced protein kinase (SGK) is provided wherein the SGK is phosphorylated. The SGK may be phosphorylated by PDK1 and/or a preparation containing PDK2 activity. A method of identifying a compound that modulates the activity of SGK is provided, wherein the activity of SGK is measured by measuring the phosphorylation by SGK of a polypeptide comprising an amino acid sequence corresponding to the consensus sequence (Arg/Lys; preferably Arg)-X-(X/Arg)-X-X-Ser/Thr)-Z wherein X indicates any amino acid, X/Arg indicates any amino acid, with a preference for arginine, and Z indicates that the amino acid residue is preferably a hydrophobic residue. The SGK may be activated by phosphorylation.

10 Claims, 20 Drawing Sheets

Figure 3:
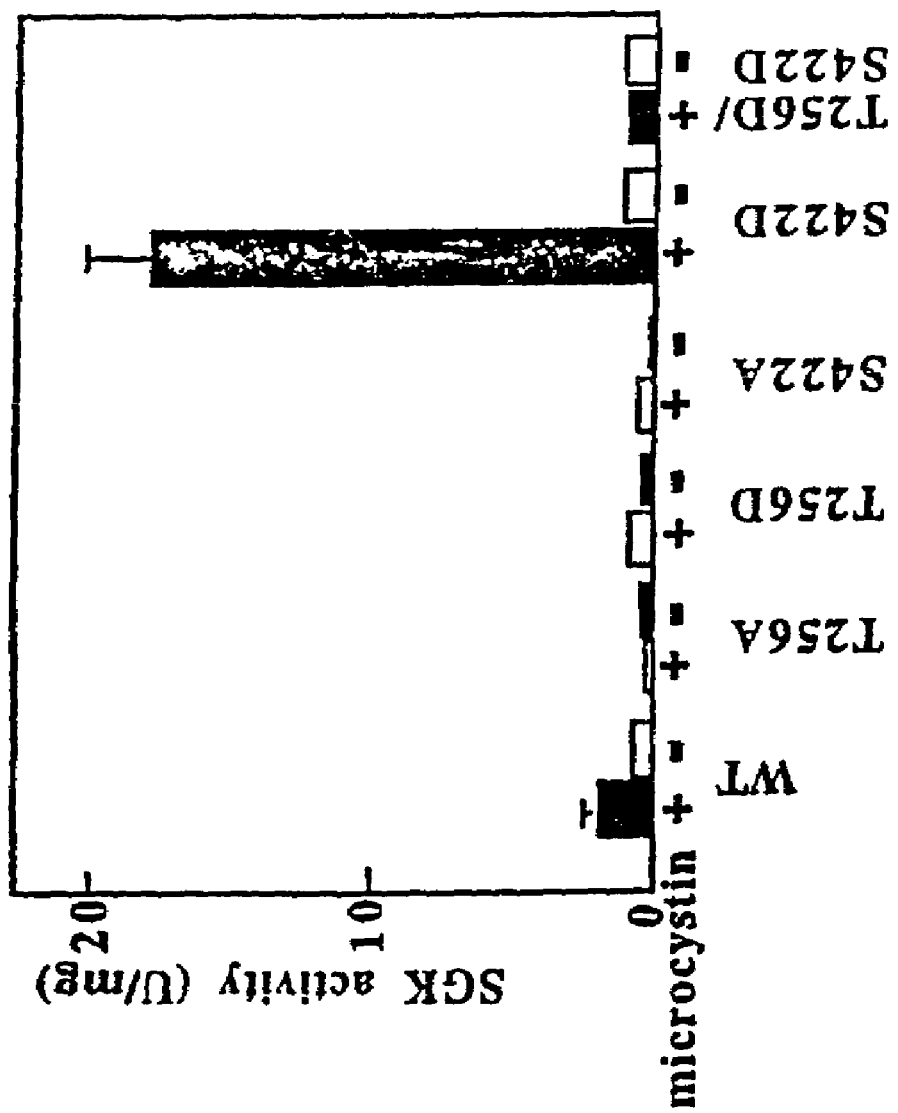

SGK      256                              422
         TTSTFCGTPEYLAPE......FLGFSYAPP

PKBα     308                              473
         TMKTFCGTPEYLAPE......FPQFSYSAS p70 S6K  229                              389
         VTHTFCGTIEYMAPE......FLGFTYVAP

PKCδ     507                              664
         RASTFCGTPDYIAPE......FAGFSFVNP   } SEQ ID NO: 45

Figure 1

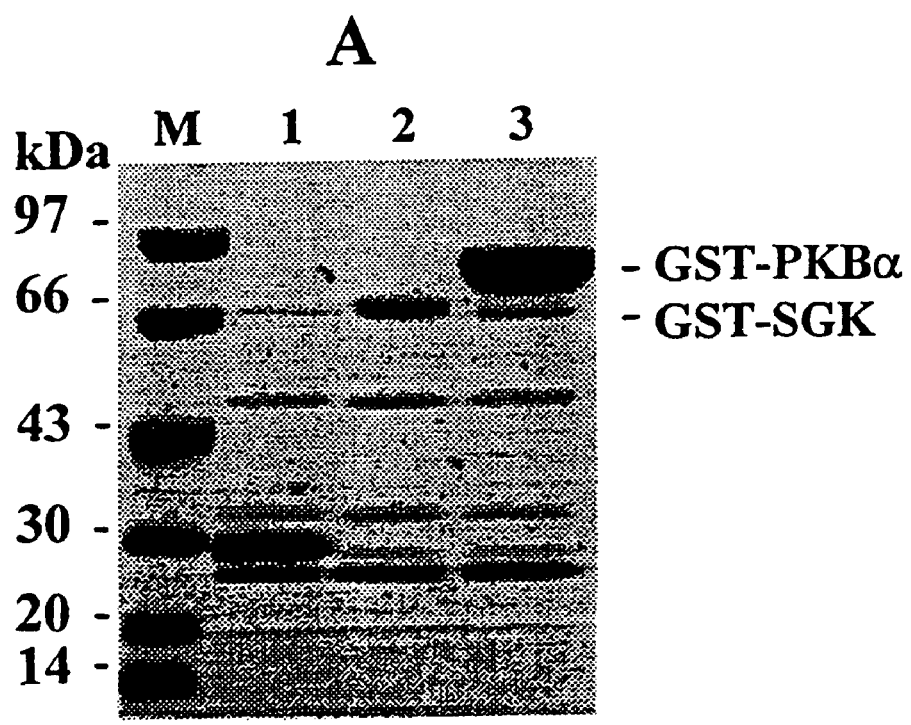
Fig. 2

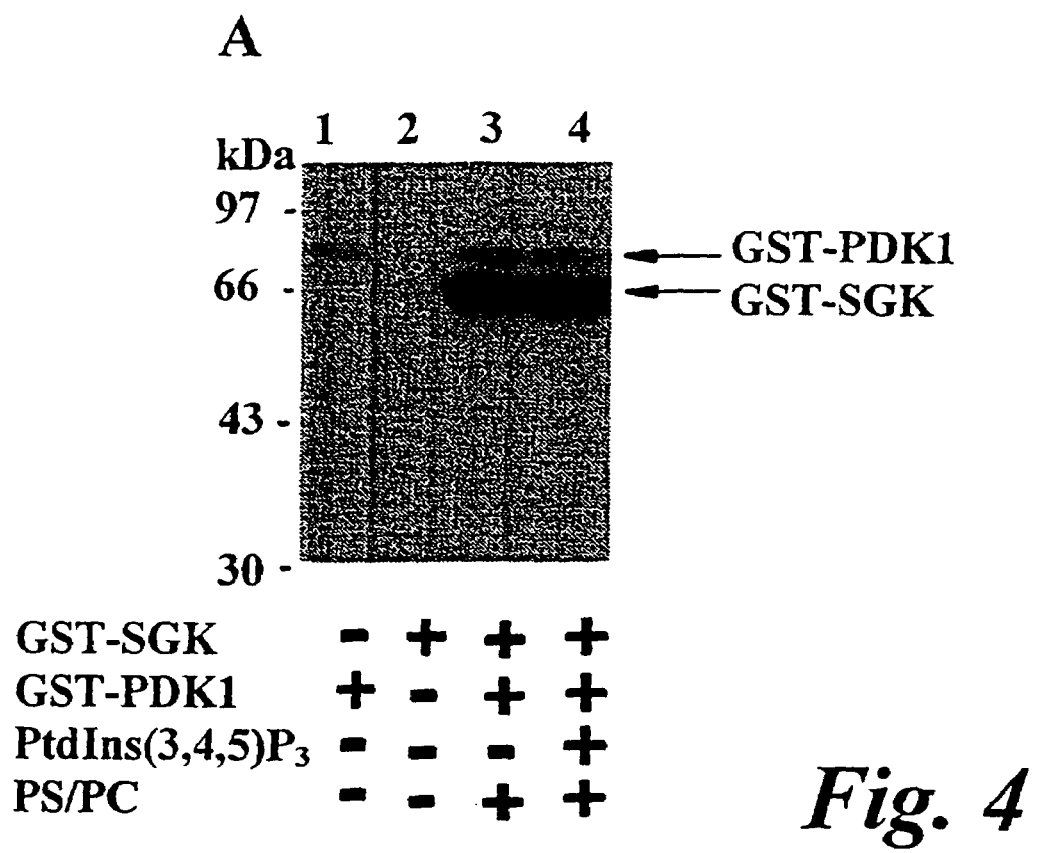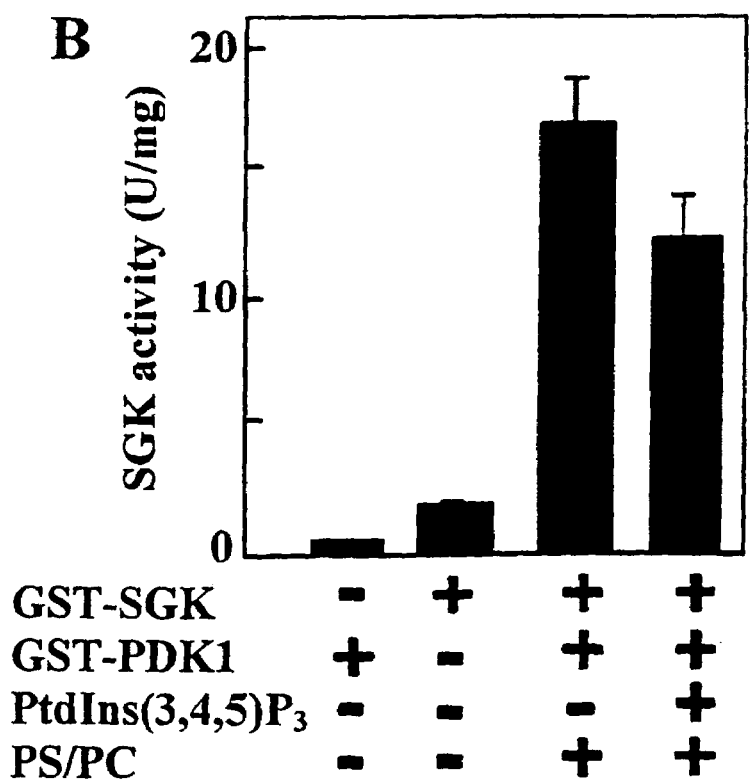
Fig. 4

Figure 11

Figure 12

\* SEQ ID NO: 3                                    \*\* SEQ ID NO: 4

```
              ┌──→SGK2β SEQ ID NO: 8
hSGK1   MTVKTEAAKG  TLTYSRMRGM  VAILIAEMKQ  RREGLNHFIQ  KIANNSYACK
hSGK2   MQGLLTSGRK  PSGGGRCTGR  GGWRGQWCLK  PWMGGAD---  -PPTPTLSCL
mSGK2*  ----------  ----------  ----------  ----------  ----------
hSGK3** MALRIPAKRI  FGD-------  -NFDPDEIKQ  RRAGLNEFIQ  NLVRYPELYN
                                     ┌──→SGK2α SEQ ID NO: 1
hSGK1   HPFVQSDLKI  SQPQEPELMN  ANPSPPPSP-  ---S-QQINL  GPSSNPEAKP
hSGK2   LLPVPPELPD  HCYRMNSSEA  GTPSEQPSR-  ---ANGNINL  GPSANENACP
mSGK2   ----------  ----MASSPV  GVPSPQPSR-  ---ANGNINL  GPSANENACP
hSGK3   HPDVRAFLQM  DSPKHQSDPS  EDEDERSSQK  LHSTSQNINL  GPSGNPFAKP hSGK1   SDFHFLKVIG  KGSFGKVLLA  RHKAEEVFYA  VKVLQKRAIL  RKKEEKHIMS
hSGK2   IDFDFLKVIG  KGNFGKVILA  KRKSLGAFYA  VKVLQKKSIL  RKKEQSHILA
mSGK2   IDFDFLKVIG  KGNFGKVILA  KRKSLGAFYA  VKVLQKKSIL  RNKEQNHILA
hSGK3   IDFDFLKVIG  KGSFGKVLLA  KRKLDGKFYA  VKVLQKRIVL  NREEDKHIMA hSGK1   ERNVLLKNVK  HPFLVGLHFS  FQTADKLYFV  LDYINGGELF  YHLQRERCFL
hSGK2   ERSVLLKNVR  HPFLVGLRYS  FQTEERLYFV  LDYVNGGELF  FHLQRERRFL
mSGK2   ERNVLLKNVR  HPFLVGLRYS  FQTEERLYFV  LDYVNGGELF  FHLQRERRFL
hSGK3   ERNVLLKNVK  HPFLVGLHYS  FQTTERLYFV  LDFVNGGELF  FHLQRERSFP hSGK1   EPRARFYAAE  IASALGYLHS  LNIVYRDLKP  ENILLDSQGH  IVLTDFGLCK
hSGK2   EPRARFYAAE  VASAIGYLHS  LNIIYRDLKP  ENILLDCQGH  VVLTDFGLCK
mSGK2   EPRARFYIAE  VASAIGYLHS  LNIIYRDLKP  ENILLDCQGH  VVLTDFGLCK
hSGK3   EPRARFYAAE  IASALGYLHS  IKIVYRDLKP  ENILLDSVGH  VVLTDFGLCK

*
hSGK1   ENIEHNSTTS  TFCGTPEYLA  PEVLRKQEYD  RTVDWWCLGA  VLYEMLYGLP
hSGK2   EGVPPETTTS  TFCGTPEYLA  PEVLRKEPYD  RAVDWWCLGA  VLYEMLHGLP
mSGK2   EGVPPETTTS  TFCGTPEYLA  PEVLRKEPYD  RAVDWWCLGA  VLYEMLHGLP
hSGK3   EGIAISDTTT  TFCGTPEYLA  PEVIRKQPYD  NTVDWWCLGA  VLYEMLYGLP hSGK1   PFYSRNTAEM  YDNILNKPLQ  LKPNITNSAR  HLLEGLLQKD  RTKRLGAKDD
hSGK2   PFYSCDVSQM  YDNILHQPLQ  IPGGRTVAAC  DLLQSLLHKD  QRORLGSKDD
mSGK2   PFFNTDVAQM  YDNILHQPLQ  IPGGRTVAAC  DLLQGLLHKD  QRORLGSKDD
hSGK3   PFYCRDVAEM  YDNILEKPLS  LRPGVSLTAW  SILEELLEKD  RQNRLGAKED hSGK1   FLEIKSHVFF  SLINWDDLIN  KKITPPFNPN  VSGPNDLRHF  DPEFTEEVP
hSGK2   FLEIQNHVFF  SFINWDDLYH  KKITPPFNPN  VTGPADLKHF  DPEFTQEAVS
mSGK2   FLEIKNHMFF  SFINWDDLLH  KRLTPPFNPN  VEGPADLKHF  DPEFTQEAVS
hSGK3   FLEIQNHPFF  ESLSWADLVQ  KKIPPPFNPN  VAGPDDIRNF  DTAFTEETVP

*
hSGK1   NSIGKSPDSV  LVTASVKEAA  EAFLGFSYAP  PTDSFL--
hSGK2   RSIGCTPDTV  ---ASSSCAS  SAFLGFSYAP  DDDDLADC
mSGK2   RSIGCTPDTV  ---ASSSCAS  SAFLGFSYAQ  DDDDEDS
hSGK3   NSVCVSSDYS  LVNASVLEAD  DAFVGFSYAP  PSEDLFL-
```

Figure 13

A- Rat2 fibroblasts
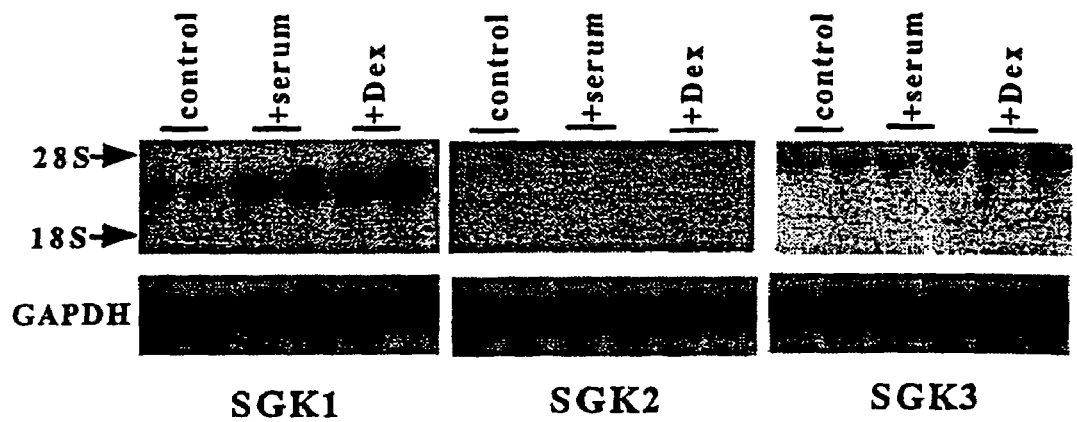
B- H4IIE Hepatoma cells
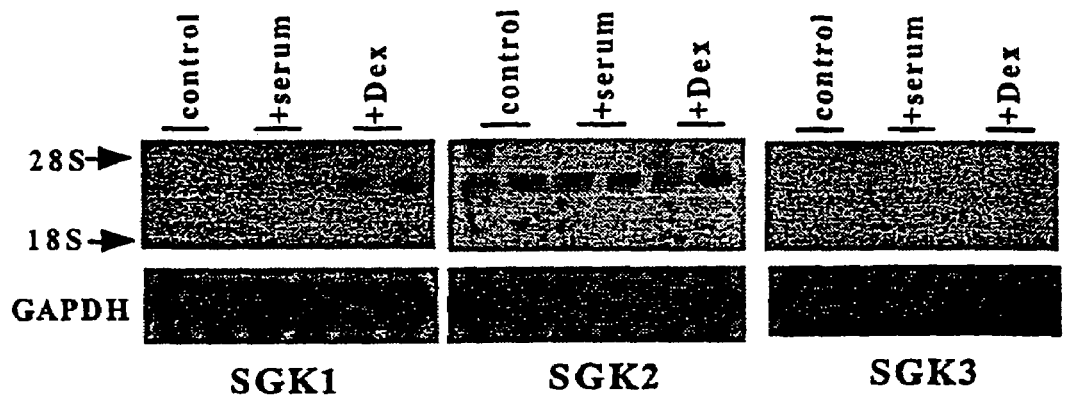
Figure 15

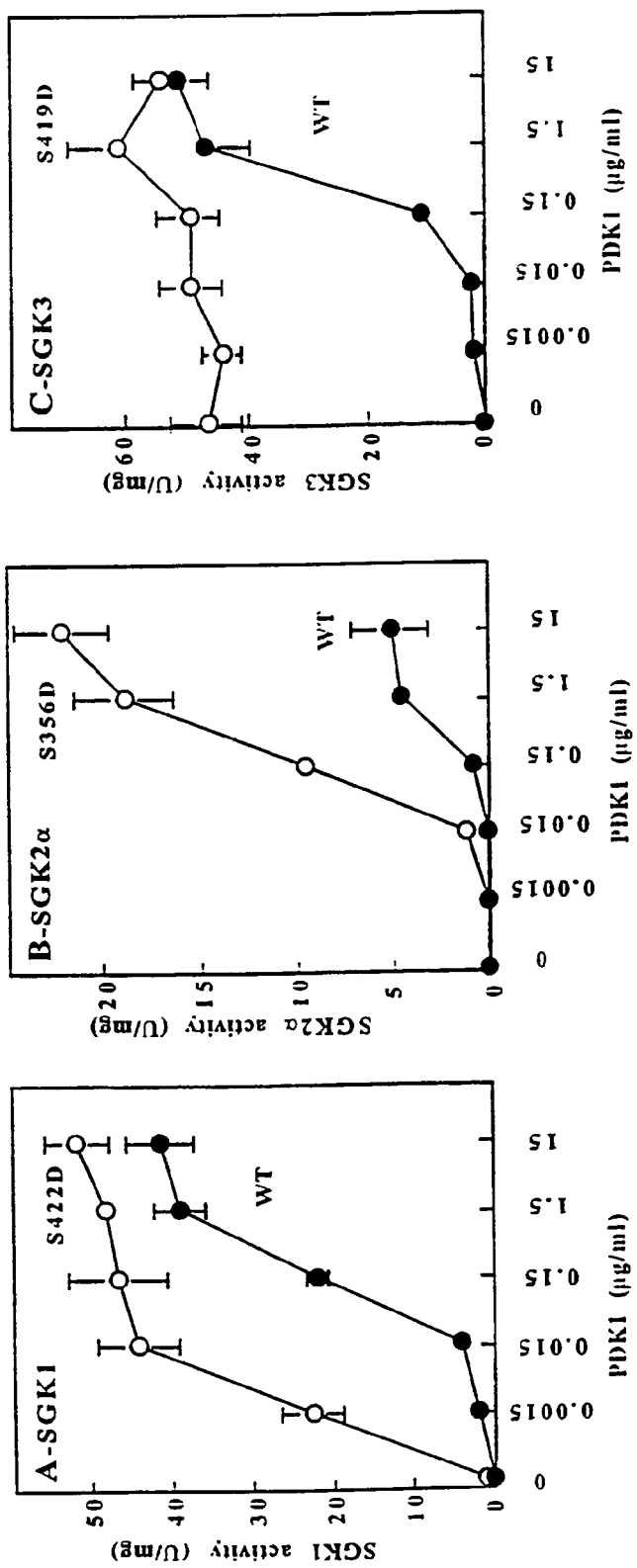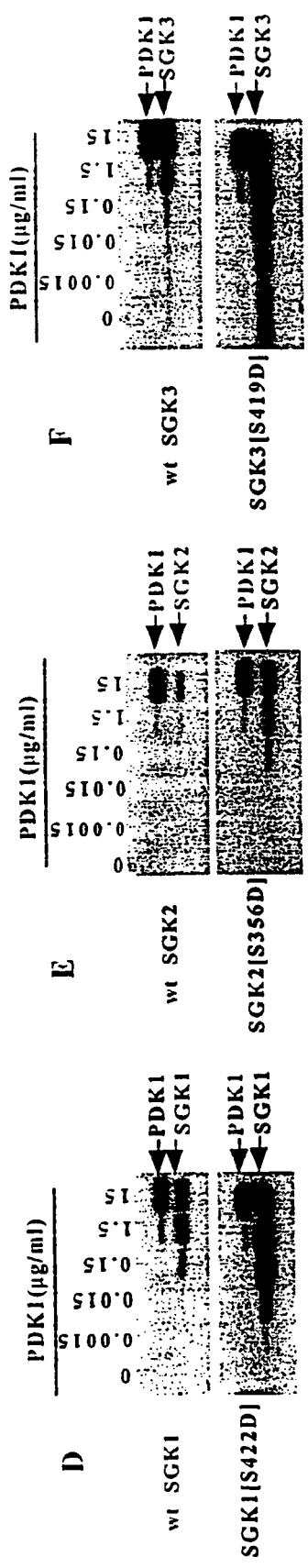
Figure 17

METHODS

The present application is a national stage filing of PCT/GB99/04232, filed Dec. 14, 1999, which claims priority to GB 9919676.8, filed August 19, 1999. The present application claims priority to U.S. Provisional Application 60/112,217, filed Dec. 14, 1998.

The present invention relates to screening methods for new drugs or lead compounds.

Protein kinase B (PKB) (also called c-Akt or RAC kinase) is believed to play a key role in mediating many of the metabolic actions of insulin, as well as the anti-apoptotic effects of survival factors such as insulin-like growth factor-1 (IGF-1) (reviewed in [1,2]). PKB is activated within a few minutes in response to insulin or survival factors via a phosphatidylinositol (PtdIns) 3-kinase dependent mechanism [3–5]. Activation results from the phosphorylation of Thr308 and Ser473, and the phosphorylation of both residues is prevented by inhibitors of PtdIns 3-kinase [6]. 3-phosphoinositide-dependent protein kinase-1 (PDK1) phosphorylates Thr308, which is located in the "activation loop" between subdomains VII and VIII of the catalytic domain, in vitro [7–9], and can be converted to a form that phosphorylates Ser473, which lies close to the C-terminus, as well as Thr308 upon interaction with a peptide corresponding to the C-terminal sequence of protein kinase C-related kinase-2 (PRK2) (Balendran et al (1999) *Curr. Biol.* 9, 393–404). However, whether Ser473 is phosphorylated in vivo by PDK1 remains to be established.

The activation of PKB by PDK1 in vitro only takes place in the presence of lipid vesicles containing PtdIns(3,4,5)P$_3$, the product of the PtdIns 3-kinase reaction, and results from the interaction of this "second messenger" with the pleckstrin homology (PH) domains of both PKB and PDK1 [9, 10].

PtdIns(3,4,5)P$_3$ is associated with the inner leaflet of the plasma membrane. The insulin or IGF-1 induced increase in PtdIns(3,4,5)P$_3$ is therefore accompanied by the recruitment of PKB from the cytosol to the plasma membrane where it becomes activated [12, 13]. Membrane recruitment appears to facilitate activation by PDK1 and PDK2 [12]. PDK1 binds to PtdIns(3,4,5)P$_3$ much more avidly than does PKB [10], and an interaction of PDK1 with the low levels of PtdIns(3,4,5)P$_3$ present under basal conditions may explain, at least in part, its constitutive association with the plasma membrane. Translocation of PDK1 from the cytosol to the plasma membrane in response to IGF-1 or PDGF may occur [14].

The amino acid sequence immediately C-terminal to Thr308 of PKB is similar to that found in other protein kinases that play important roles in signal transduction, such as p70 S6 kinase and protein kinase C (FIG. 1). PDK1 activates p70 S6 kinase [15, 16], PKCδ and PKCζ [17, Chou et al (1998) *Curr Biol* 8, 1069–1077] in vitro, and in cotransfection experiments, by phosphorylating the residue equivalent to Thr308 of PKB. The activation of p70 S6 kinase by PDK1 in vitro is not affected by PtdIns(3,4,5)P$_3$.

Like PKB, p70 S6 kinase and PKC contain the proposed consensus sequence for phosphorylation by the protein kinase activity termed PDK2 (Phe-Xaa-Xaa-(Phe/Tyr)-(Ser/Thr)-(Phe/Tyr)) (SEQ. ID. NO:45), which is always located 160–165 residues C-terminal to the PDK1 phosphorylation site (FIG. 1). These observations suggest that PDK1 and the protein kinase activity termed PDK2 may participate together in the activation of a number of protein kinases. A PDK2 activity has been characterised (Balendran et al (1999) *Curr. Biol.* 9, 393–404; UK patent application No 9906245.7 filed 19 Mar. 1999 and Alessi et al U.S. patent application filed 2 Dec. 1999).

Serum and glucocorticoid-induced protein kinase (SGK) was originally identified in a differential screen aimed at finding glucocorticoid-inducible transcripts [18]. The levels of SGK mRNA and protein are both elevated 5–10 fold, with a half time of 30 min in Rat2 fibroblasts, following cell stimulation with serum or glucocorticoids [19]. SGK is also induced in response to other stimuli, such as follicle-stimulating hormone [20], increased extracellular osmolarity [21], injury of the brain [22, 23] and by transfection of mammary epithelial cells with p53 [24]. However, the glucocorticoid-stimulated induction of SGK is suppressed by wild type p53 in Rat2 fibroblasts, but not by mutant p53 [25].

The structure of SGK is similar to PKB, but it lacks a PH domain. The catalytic domain of SGK is 54% identical to PKB, 50% identical to p70 S6 kinase and 48% identical to PKC.

We demonstrate here that SGK is activated by IGF-1 or an oxidative stress in 293 cells via a PtdIns 3-kinase-dependent pathway. Activation appears to result from phosphorylation. Further, SGK possesses a threonine residue at the position equivalent to Thr308 of PKB and a serine residue equivalent to Ser473, and the sequences surrounding these residues are consistent with an ability to be phosphorylated by PDK1 and a PDK2 activity (FIG. 1). Activation appears to result from phosphorylation of the residues equivalent to Thr308 and Ser473, and the residue equivalent to Thr308 is phosphorylated and SGK activated by PDK1 in vitro. SGK preferentially phosphorylates serine and threonine residues that lie in an Arg-Xaa-Arg-Xaa-Xaa-(Ser/Thr)- motif (SEQ. ID. NO:46), and inactivates glycogen synthase kinase-3 (GSK3) at similar rates to PKB in vitro.

We further identify novel isoforms of SGK, termed SGK2 and SGK3, that are activated in a similar manner to the previously identified SGK [18] (herein termed SGK1). The catalytic domains of SGK2 and SGK3 share 80% amino acid sequence identity with each other and with SGK1.

A first aspect of the invention is a method of activating serum and glucocorticoid-induced protein kinase (SGK) wherein the SGK is phosphorylated. The SGK that is activated by the method may be partially or fully deactivated/dephosphorylated SGK.

A further aspect of the invention is a method of reducing the activity of SGK wherein the SGK is dephosphorylated. The SGK the activity of which is reduced may be partially or fully activated/phosphorylated SGK.

By "activating" is meant that the enzymatic activity of SGK is increased. By "reducing the activity" is meant that the enzymatic activity of SGK is reduced. The enzymatic activity that may be increased or reduced is protein kinase activity, preferably Serine/Threonine protein kinase activity ie the phosphorylation of a protein/polypeptide on one or more serine or threonine residues. The enzymatic activity may be increased or reduced by an alteration in the $V_{max}$ or the $K_m$ (or both) of the SGK for a particular substrate. For example, activity may be increased by an increased $V_{max}$ or decreased $K_m$. It will be appreciated that it may not be necessary to determine the value of either $V_{max}$ or $K_m$ in order to determine whether the SGK has been activated or deactivated. It will be appreciated that dephosphorylated (deactivated) SGK may retain some enzymatic activity.

Activity may be measured as the amount of a substrate phosphorylated in a given time; a change of activity may therefore be detected as a change in the amount of substrate (for example, at a single concentration) that is phosphorylated in a given time, as described in Example 1. The substrate may be a polypeptide comprising the consensus sequence Arg-X-(X/Arg)-X-X-(Ser/Thr)-Z (SEQ. ID. NO:46) where X indicates any amino acid, X/Arg indicates any amino acid, with a preference for arginine, and Z indicates that the amino acid residue is preferably a hydrophobic residue. An example of such a polypeptide is the peptide Crosstide (GRPRTSSFAEG) (SEQ. ID. NO: 30). The underlined residue may be phosphorylated by the said protein kinase. Other examples of polypeptides that may be substrates of SGK are shown in Table 1 and Table 2. Glycogen synthase kinase-3 (GSK3) may be a substrate of SGK, as discussed in Example 1.

It will be appreciated that if the SGK is already phosphorylated, further phosphorylation may not be possible and/or may not lead to further activation. Further, if the SGK is already partially dephosphorylated, then further dephosphorylation may not be possible and/or may not lead to further deactivation.

It will further be appreciated that SGK isolated from cells (either as an endogenous or recombinant polypeptide) may be heterogeneous with regard to its phosphorylation/activation state. For example, fully activated/phosphorylated, fully deactivated/dephosphorylated and/or partially activated/phosphorylated molecules of SGK may be present in a single cell or group/culture of cells.

It is preferred that the activity is increased or decreased, as appropriate, by at least 2, preferably 5, 10, 15, 20, 25, 30 or 50-fold.

By serum and glucocorticoid-induced protein kinase (SGK) is included a polypeptide, preferably a protein kinase, encoded by I.M.A.G.E Consortium clone ID 42669 (which comprises a full-length cDNA from a human infant brain library identified as encoding human serum and glucocorticoid-induced protein kinase). The term serum and glucocorticoid-induced protein kinase is well known to those skilled in the art (see, for example, references 18 to 25). The amino acid sequence of human serum and glucocorticoid-induced protein kinase (herein termed SGK1) may have the Genbank accession reference Y10032. The amino acid sequence of rat serum and glucocorticoid-induced protein kinase may have the Genbank accession reference L01624. Nematode (*Caenorhabditis elegans*) serum and glucocorticoid-induced protein kinase may be encoded by a portion of the 26 kb fragment from chromosome 3 genomic DNA with the accession number 281140.

By serum and glucocorticoid-induced protein kinase (SGK) is further included a polypeptide (termed SGK2) having the amino acid sequence

```
MNSSPAGTPSPQPSRANGNINLGPSANPNAQPTDFDFLKVIGKGNYGKVLLAKRK    (SEQ. ID. NO:1)

SDGAFYAVKVLQKKSILKKKEQSHIMAERSVLLKNVRHPFLVGLRYSFQTPEKLY

FVLDYVNGGELFFHLQRERRFLEPRARFYAAEVASAIGYLHSLNIIYRDLKPENI

LLDCQGHVVLTDFGLCKEGVEPEDTTSTFCGTPEYLAPEVLRKEPYDRAVDWWCL

GAVLYEMLHGLPPFYSQDVSQMYENILHQPLQIPGGRTVAACDLLQSLLHKDQRQ

RLGSKADFLEIKNHVFFSPINWDDLYHKRLTPPFNPNVTGPADLKHFDPEFTQEA

VSKSIGCTPDTVASSSGASSAFLGFSYAPEDDDILDC or

MQGLLTSGRKPSGGGRCTGRGGWRGQWCLKPWMGGADPPTPTLSCLLLPVPPELP    (SEQ. ID. NO:8)

DHCYRMNSSPAGTPSPQPSRANGNINLGPSANPNAQPTDFDFLKVIGKGNYGKVL

LAKRKSDGAFYAVKVLQKKSILKKKEQSHIMAERSVLLKNVRHPFLVGLRYSFQT

PEKLYFVLDYVNGGELFFHLQRERRFLEPRARFYAAEVASAIGYLHSLNIIYRDL

KPENILLDCQGHVVLTDFGLCKEGVEPEDTTSTFCGTPEYLAPEVLRKEPYDRAV

DWWCLGAVLYEMLHGLPPFYSQDVSQMYENILHQPLQIPGGRTVAACDLLQSLLH

KDQRQRLGSKADFLEIKNHVFFSPINWDDLYHKRLTPPFNPNVTGPADLKHFDPE

FTQEAVSKSIGCTPDTVASSSGASSAFLGFSYAPEDDDILDC or

MASSPVGVPSPQPSRANGNINLGPSANPNARPTDFDFLKVIGKGNYGKVLLAKRK    (SEQ. ID. NO:3)

SDGAFYAVKVLQKKSILKNKEQNHIMAERNVLLKNVRHPFLVGLRYSFQTPEKLY

FVLDYVNGGELFFHLQRERRFLEPRARFYTAEVASAIGYLHSLNIIYRDLKPENI

LLDCQGHVVLTDFGLCKECVEPEETTSTFCGTPEYLAPEVLRKEPYDRAVDWWCL

GAVLYEMLHGLPPFFNTDVAQMYENILHQPLQIPGGRTVAACDLLQGLLHKDQRQ

RLGSKEDFLDIKNHMFFSPINWDDLYHKRLTPPFNPNVEGPADLKHFDPEFTQEA

VSKSIGCTPDTVASSSGASSAFLGFSYAQDDDDILDS
```

The first sequence is that of human SGK2α, the second that of human SGK2β and the third sequence is that of mouse SGK2. SGK2β has an N-terminal 60 amino acids that are not present in SGKα.

By serum and glucocorticoid-induced protein kinase (SGK) is still further included a polypeptide (termed SGK3) having the amino acid sequence

```
MALKIPAKRIFGDNFDPDFIKQRRAGLNEFIQNLVRYPELYNHPDVRAFLQMDSP    (SEQ. ID. NO:4)
KHQSDPSEDEDERSSQKLHSTSQNINLGPSGNPHAKPTDFDFLKVIGKGSFGKVL
LAKRKLDGKFYAVKVLQKKIVLNRKEQKHIMAERNVLLKNVKHPFLVGLHYSFQT
TEKLYFVLDFVNGGELFFHLQRERSFPEHRARFYAAEIASALGYLHSIKIVYRDL
KPENILLDSVGHVVLTDFGLCKEGIAISDTTTTFCGTPEYLAPEVIRKQPYDNTV
DWWCLGAVLYEMLYGLPPFYCRDVAEMYDNILHKPLSLRPGVSLTAWSILEELLE
KDRQNRLGAKEDFLEIQNHPFFESLSWADLVQKKIPPPFNPNVAGPDDIRNFDTA
FTEETVPYSVCVSSDYSIVNASVLEADDAFVGFSYAPPSEDLFL
```

An alignment of the sequences of SGK1, 2, 3 and mouse SGK2 is shown in FIG. 13.

A further aspect of the invention provides a substantially pure polypeptide comprising the amino acid sequence

```
MNSSPAGTPSPQPSRANGNINLGPSANPNAQPTDFDFLKVIGKGNYGKVLLAKRK    (SEQ. ID. NO:1)
SDGAFYAVKVLQKKSILKKKEQSHIMAERSVLLKNVRHPFLVGLRYSFQTPEKLY
FVLDYVNGGELFFHLQRERRFLEPRARFYAAEVASAIGYLHSLNIIYRDLKPENI
LLDCQGHVVLTDFGLCKEGVEPEDTTSTFCGTPEYLAPEVLRKEPYDRAVDWWCL
GAVLYEMLHGLPPFYSQDVSQMYENILHQPLQIPGGRTVAACDLLQSLLHKDQRQ
RLGSKADFLEIKNHVFFSPINWDDLYHKRLTPPFNPNVTGPADLKHFDPEFTQEA
VSKSIGCTPDTVASSSGASSAFLGFSYAPEDDDILDC
``` or

```
MQGLLTSGRKPSGGGRCTGRGGWRGQWCLKPWMGGADPPTPTLSCLLLPVPPELP    (SEQ. ID. NO:8)
DHCYRMNSSPAGTPSPQPSRANGNINLGPSANPNAQPTDFDFLKVIGKGNYGKVL
LAKRKSDGAFYAVKVLQKKSILKKKEQSHIMAERSVLLKNVRHPFLVGLRYSFQT
PEKLYFVLDYVNGGELFFHLQRERRFLEPRARFYAAEVASAIGYLHSLNIIYRDL
KPENILLDCQGHVVLTDFGLCKEGVEPEDTTSTFCGTPEYLAPEVLRKEPYDRAV
DWWCLGAVLYEMLHGLPPFYSQDVSQMYENILHQPLQIPGGRTVAACDLLQSLLH
KDQRQRLGSKADFLEIKNHVFFSPINWDDLYHKRLTPPFNPNVTGPADLKHFDPE
FTQEAVSKSIGCTPDTVASSSGASSAFLGFSYAPEDDDILDC
``` or

```
MASSPVGVPSPQPSRANGNINLGPSANPNARPTDFDFLKVIGKGNYGKVLLAKRK    (SEQ. ID. NO:3)
SDGAFYAVKVLQKKSILKNKEQNHIMAERNVLLKNVRHPFLVGLRYSFQTPEKLY
FVLDYVNGGELFFHLQRERRFLEPRARFYTAEVASAIGYLHSLNIIYRDLKPENI
LLDCQGHVVLTDFGLCKECVEPEETTSTFCGTPEYLAPEVLRKEPYDRAVDWWCL
GAVLYEMLHGLPPFFNTDVAQMYENILHQPLQIPGGRTVAACDLLQGLLHKDQRQ
RLGSKEDFLDIKNHMFFSPINWDDLYHKRLTPPFNPNVEGPADLKHFDPEFTQEA
VSKSIGCTPDTVASSSGASSAFLGFSYAQDDDDILDS
``` or

-continued

```
MALKIPAKRIFGDNFDPDFIKQRRAGLNEFIQNLVRYPELYNHPDVRAFLQMDSP  (SEQ. ID. NO:4)

KHQSDPSEDEDERSSQKLHSTSQNINLGPSGNPHAKPTDFDFLKVIGKGSFGKVL

LAKRKLDGKFYAVKVLQKKIVLNRKEQKHIMAERNVLLKNVKHPFLVGLHYSFQT

TEKLYFVLDFVNGGELFFHLQRERSFPEHRARFYAAEIASALGYLHSIKIVYRDL

KPENILLDSVGHVVLTDFGLCKEGIAISDTTTTFCGTPEYLAPEVIRKQPYDNTV

DWWCLGAVLYEMLYGLPPFYCRDVAEMYDNILHKPLSLRPGVSLTAWSILEELLE

KDRQNRLGAKEDFLEIQNHPFFESLSWADLVQKKIPPPFNPNVAGPDDIRNFDTA

FTEETVPYSVCVSSDYSIVNASVLEADDAFVGFSYAPPSEDLFL
``` or a variant, fragment, fusion or derivative thereof, or a fusion of a said variant or fragment or derivative. The said variant, fragment, fusion or derivative thereof is preferably a protein kinase, more preferably a protein kinase that is capable of phosphorylating a polypeptide comprising the consensus Arg-X-(X/Arg)-X-X-(Ser/Thr)-Z (SEQ. ID. NO:47), as discussed further below, and is not SGK1, PKBα, PKCδ, PKCξ, p70 S6 kinase, MSK1 or MSK2 or a fragment or fusion thereof. The polypeptides whose amino acid sequences are shown above are considered to be serum and glucocorticoid-induced protein kinases. The SGK2 mRNA is present at highest levels in liver, kidney and pancreas and is also present in the brain, whereas levels of mRNA encoding SGK1 and SGK3 are similar in all tissues tested (see Example 5).

By "substantially pure" we mean that the said polypeptide is substantially free of other proteins. Thus, we include any composition that includes at least 30% of the protein content by weight as the said polypeptide, preferably at least 50%, more preferably at least 70%, still more preferably at least 90% and most preferably at least 95% of the protein content is the said polypeptide.

Thus, the invention also includes compositions comprising the said polypeptide and a contaminant wherein the contaminant comprises less than 70% of the composition by weight, preferably less than 50% of the composition, more preferably less than 30% of the composition, still more preferably less than 10% of the composition and most preferably less than 5% of the composition by weight.

The invention also includes the substantially pure said polypeptide when combined with other components ex vivo, said other components not being all of the components found in the cell in which said polypeptide is found.

SGK, for example the activated or deactivated SGK obtained or obtainable by the above methods of the invention, may be useful, for example in screening methods, such as those set out below. Thus, it will be appreciated that the term SGK as used herein includes a polypeptide comprising an amino acid sequence given above for SGK2 or SGK3 or the amino acid sequence of the polypeptide, preferably a protein kinase, encoded by I.M.A.G.E Consortium clone ID 42669, or a variant, fragment, fusion or derivative thereof, or a fusion of a said variant or fragment or derivative, wherein the said polypeptide is a protein kinase. It is preferred that the said polypeptide is a protein kinase that is capable of phosphorylating a polypeptide comprising the consensus Arg-X-(X/Arg)-X-X-(Ser/Thr)-Z (SEQ. ID. NO:47) where X indicates any amino acid, X/Arg indicates any amino acid, with a preference for arginine, and Z indicates that the amino acid residue is preferably a hydrophobic residue. An example of such a polypeptide is Crosstide (GRPRTS$\underline{S}$FAEG) (SEQ. ID. NO:30). The underlined residue may be phosphorylated by the said protein kinase. Other examples of polypeptides that may be phosphorylated by the said protein kinase are shown in Table 1 and may include GSK3, as discussed in Example 1. As discussed in Example 5, serine 279 of SGK2 lies in a sequence conforming to the consensus sequence for phosphorylation by SGK and PKB. SGK2 may therefore be capable of being phosphorylated by the said protein kinase, for example SGK2. It will be appreciated that the said protein kinase is not PKB (for example, PKBα), p70 S6 kinase, protein kinase C (for example, PKCδ or PKCξ), MAPKAP kinase-1 (Leighton et al (1995) FEBS Lett 375, 289–293) or MSK1 or MSK2 (see, for example, UK patent applications 9817303.2, filed 10 Aug. 1998 and 9813467.9, filed 24 Jun. 1998). As discussed in Example 5, SGK3, for example, may also be capable of phosphorylating a serine residue equivalent to serine 77 or serine 79 of full-length human SGK3.

It will be appreciated that a said polypeptide may be useful, for example in some of the screening assays as set out below, even if it does not possess protein kinase activity as defined above. It will further be appreciated that the phosphorylation of such a polypeptide may be detected by means described herein other than by detecting a change in enzymatic, in particular protein kinase, activity of the polypeptide.

It is preferred that the SGK comprises an amino acid sequence corresponding to the consensus sequence B-$\underline{T}$-F-C-G-T-(P/I)-(D/E)-Y-(L/I/M)-A-P-E (SEQ. ID. NO:48), where B is a basic residue, the consensus sequence for phosphorylation of a polypeptide by PDK1, and/or the consensus sequence Phe-Xaa-Xaa-(Phe/Tyr)-(Ser/Thr)-(Phe/Tyr) (SEQ. ID. NO:45), the consensus sequence proposed for phosphorylation of a polypeptide by PDK2 protein kinase activity. Preferably both consensus sequences are present. Alternatively, the Ser/Thr in either consensus sequence may be replaced by an aspartate or glutamate (ie acidic) residue; it is preferred that only one such consensus sequence in a polypeptide is replaced in this way. It is preferred that the Ser/Thr in the consensus sequence for phosphorylation by PDK1 is not replaced in this way; as described in Example 1, replacement of Thr256 to Asp in human SGK1 may abolish activation of SGK.

By "variants" of the polypeptide we include insertions, deletions and substitutions, either conservative or non-conservative. In particular we include variants of the polypeptide where such changes do not substantially alter the activity of the said protein kinase.

By "conservative substitutions" is intended combinations such as Gly, Ala; Val, Ile, Leu; Asp, Glu; Asn, Gln; Ser, Thr; Lys, Arg; and Phe, Tyr.

It is particularly preferred if the SGK variant has an amino acid sequence which has at least 65% identity with the amino acid sequence of the polypeptide, preferably a protein kinase, encoded by I.M.A.G.E Consortium clone ID 42669, more preferably at least 70%, 71%, 72%, 73% or 74%, still more preferably at least 75%, yet still more preferably at least 80%, in further preference at least 85%, in still further preference at least 90% and most preferably at least 95% or 97% identity with the amino acid sequence encoded by I.M.A.G.E Consortium clone ID 42669.

It is particularly preferred that a SGK2 or SGK3 variant has an amino acid sequence which has at least 65% identity with the amino acid sequence of SGK2 or SGK3, as appropriate, indicated above, more preferably at least 70%, 71%, 72%, 73% or 74%, still more preferably at least 75%, yet still more preferably at least 80%, in further preference at least 85%, in still further preference at least 90% and most preferably at least 95% or 97% identity with the amino acid sequence of SGK2 or SGK3 indicated above.

It is still further preferred if the SGK variant has an amino acid sequence which has at least 65% identity with the amino acid sequence of the catalytic domain of the polypeptide, preferably a protein kinase, encoded by I.M.A.G.E Consortium clone ID 42669, more preferably at least 70%, 71%, 72%, 73% or 74%, still more preferably at least 75%, yet still more preferably at least 80%, in further preference at least 83 or 85%, in still further preference at least 90% and most preferably at least 95% or 97% identity with the amino acid sequence defined above.

It is still further preferred that a SGK2 or SGK3 variant has an amino acid sequence which has at least 65% identity with the amino acid sequence of the catalytic domain of an SGK2 or SGK3 polypeptide whose sequence is indicated above, as appropriate, more preferably at least 70%, 71%, 72%, 73% or 74%, still more preferably at least 75%, yet still more preferably at least 80%, in further preference at least 83 or 85%, in still further preference at least 90% and most preferably at least 95% or 97% identity with the SGK2 or SGK3 amino acid sequence defined above.

It will be appreciated that the catalytic domain of a protein kinase-related polypeptide may be readily identified by a person skilled in the art, for example using sequence comparisons as described below, and as described in relation to SGK in, for example, Webster et al (1993) *Mol Cell Biol* 13(4), 2031–2040. For example, as discussed in Example 5, the amino acid sequences of the three SGK isoforms are about 80% identical to one another in the catalytic domain, while the short C-terminal non-catalytic domains are less similar (44–68% identity). The N-terminal 85 residues that precede the catalytic domain are much less similar. In this region there is only about 25% identity between SGK1 and SGK3 and almost no identity between SGK2 and the other isoforms (FIG. 13).

The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (Thompson et al., 1994). The parameters used may be as follows:

Fast pairwise alignment parameters: K-tuple(word) size; 1, window size; 5, gap penalty; 3, number of top diagonals;

5. Scoring method: x percent. Multiple alignment parameters: gap open penalty; 10, gap extension penalty; 0.05.

Scoring matrix: BLOSUM.

It will be appreciated that SGK2 and SGK3, as defined above by their amino acid sequence, are examples of SGK variants as defined above.

It is preferred that the SGK is a polypeptide which consists of the amino acid sequence of the protein kinase encoded by I.M.A.G.E Consortium clone ID 42669, or SGK2 or SGK3, the amino acid sequences of which are given above, or naturally occurring allelic variants (including splice variants) thereof.

It is also preferred that the SGK is one of the following:

(1) a polypeptide encoded by I.M.A.G.E Consortium clone ID 42669 (SGK1) or SGK2 or SGK3 as defined above lacking the amino acids equivalent to the N-terminal 60 amino acids of full-length human SGK1 (for example ΔN-SKG(61–431) as described in Example 1 or SGK2α as described in Example 5 and shown in FIG. 13)

(2) full-length SGK or SGK lacking the N-terminal 60 amino acids, as described above, in which the residue equivalent to serine 422 of full-length SGK1 is replaced by aspartate or glutamate (preferably aspartate) and/or the residue equivalent to threonine 256 of full-length SGK1 is replaced by aspartate or glutamate or alanine (3) a fusion polypeptide of glutathione-S-transferase (GST) and any of the variants of SGK described above, for example a fusion protein comprising the GST encoded by the GST sequence of the plasmid pEBG2T, as known to those skilled in the art. Examples include GST-ΔN-SGK [S422D], as described in Example 1.

It will be appreciated that SGK in which the residue equivalent to threonine 256 of full-length SGK1 is replaced, for example by an alanine, glutamate or aspartate residue, may not be capable of being significantly activated by phosphorylation and may therefore be less preferred than some other SGKs for use in the screening methods of the invention. Thus, GST-SGK[T256D], GST-SGK[T256E], GST-SGK[T256A], as described in Example 1, may not be capable of being significantly activated by phosphorylation and may therefore be less preferred than some other SGKs for use in the screening methods of the invention.

As discussed in Example 5, the residue equivalent to serine 422 of SGK1 in SGK2α is serine 356 and in SGK3 is serine 419. The residue equivalent to threonine 256 of SGK1 in SGK2α is threonine 193 and in SGK3 is threonine 253.

It will further be appreciated that SGK in which the residue equivalent to serine 422 of full-length SGK1 is replaced by an amino acid residue other than glutamate or aspartate (ie an acidic residue) or a residue that may be phosphorylated, for example by an alanine residue, may not be capable of being activated by phosphorylation or may be less capable of being activated by phosphorylation than SGK in which the said residue equivalent to serine 422 is not so replaced.

It will be appreciated that a mutated SGK which does not have any protein kinase activity ("kinase dead" mutant) may be phosphorylated in a similar manner to SGK that does have protein kinase activity, but that no change in protein kinase activity may be discernible. Such a mutated SGK may be SGK in which the residue equivalent to lysine 127 of full-length SGK1 (which may lie in the ATP binding site) is replaced by alanine, as described in Example 1.

SGK (as defined above) may be phosphorylated by phosphatidylinositol dependent kinase 1 (PDK1), or a variant, fragment, fusion or derivative thereof, or a fusion of a said variant, fragment or derivative. The term PDK1 is well known to those skilled in the art (see, for example, references 7 to 9) and includes, in particular, PDK1 as described and expressed in reference 9 and in co-pending application PCT/GB98/00777. It is preferred that the said variant, fragment, fusion or derivative of PDK1, or a fusion of a said variant, fragment or derivative is a protein kinase, preferably a protein kinase capable of phosphorylating a polypeptide comprising an amino acid sequence corresponding to the consensus sequence B-T-F-C-G-T-(P/I)-(D/E)-Y-(L/I/M)-A-P-E (SEQ. ID. NO:48). Such variants of PDK1 may be functional equivalents of PDK1 and include Pkh1 and Pkh2 from *Saccharomyces cerevisiae* as described in the U.S. patent application entitled "Screening Methods" filed on the same day as this application.

SGK may be dephosphorylated by a serine/threonine protein phosphatase, for example PP1 (Berndt et al (1987) *FEBS Lett* 223, 340–346), PP2C (Mann et al (1992) *Biochem et Biophys Acta* 1130, 100–104 or protein phosphorylase 2A (PP2A; da Cruz E Silva (1987) *FEBS Lett* 221, 415–422) or a variant, fragment, fusion or derivative any thereof, or a fusion of a said variant, fragment or derivative. PP1, PP2C or PP2A or a variant, fragment, fusion or derivative any thereof, or a fusion of a said variant, fragment or derivative is capable of dephosphorylating phosphorylase a. The terms PP1, PP2C, PP2A and phosphorylase a are well known to those skilled in the art. PP2A may be inactivated by microcystin-LR at 1 µM.

A further aspect of the invention is the use of a serine/threonine protein phosphatase, for example PP1, PP2C, PP2A or a variant, fragment, fusion or derivative any thereof, or a fusion of a said variant, fragment or derivative (as defined above) in a method of deactivating and/or dephosphorylating SGK. The SGK may be phosphorylated SGK, as discussed above.

A still further aspect of the invention is the use of a protein kinase, preferably PDK1 or a variant, fragment, fusion or derivative thereof, or a fusion of a said variant, fragment or derivative (as defined above) in a method of activating and/or phosphorylating SGK. The SGK may be dephosphorylated SGK, as discussed above.

A further aspect of the invention is a method of activating SGK (as defined above) wherein SGK is phosphorylated on the residue equivalent to Thr256 of full-length human SGK1. SGK (for example full-length human SGK and ΔN-SGK(61–431), may be phosphorylated on the residue equivalent to Thr 256 of full-length human SGK1 by PDK1. SGK may be activated by phosphorylation on this residue, as described in Example 1 and Example 5. It will be appreciated that SGK in which the residue equivalent to serine 422 of full-length SGK1 is replaced by an acidic residue, for example glutamate or aspartate, may be more readily phosphorylated and/or activated than SGK in which the said residue equivalent to serine 422 is not so replaced. For example, recombinant SGK in which the residue equivalent to serine 422 of full-length SGK1 is replaced by an acidic residue, for example glutamate or aspartate, may be substantially phosphorylated on the residue equivalent to Thr256 of full-length human SGK1 when expressed in a eukaryotic, preferably mammalian, cell. Such recombinant SGK may be useful in screening assays in which activated SGK is required, as discussed further below.

It will be appreciated that a protein kinase capable of phosphorylating SGK on the residue equivalent to Thr256 of full-length human SGK1 may be identified by determining whether any particular protein kinase is capable of activating SGK and/or determining what, if any residue of SGK may be phosphorylated by the said particular protein kinase, for example as described in Example 1.

By "residue equivalent to Thr256 of full-length human SGK1", for example, is included the meaning that the amino acid residue that occupies a position in the native three dimensional structure of a protein kinase corresponding to the position occupied by Thr 256 in the native three dimensional structure of human full-length SGK1. It will be appreciated that Thr256 of human full-length SGK1 is located in the "activation loop" between subdomains VII and VIII of the catalytic domain.

Protein kinases show a conserved catalytic core, as reviewed in Johnson et al (1996) *Cell*, 85, 149–158 and Taylor & Radzio-Andzelm (1994) *Structure* 2, 345–355. This core folds into a small N-terminal lobe largely comprising anti-parallel β-sheet, and a large C-terminal lobe which is mostly α-helical.

The residue equivalent to, for example, Thr 256 of full-length human SGK1 may be identified by alignment of the sequence of the polypeptide with that of full-length human SGK1 in such a way as to maximise the match between the sequences. The alignment may be carried out by visual inspection and/or by the use of suitable computer programs, for example the GAP program of the University of Wisconsin Genetic Computing Group, which will also allow the percent identity of the polypeptides to be calculated. The Align program (Pearson (1994) in: Methods in Molecular Biology, Computer Analysis of Sequence Data, Part II (Griffin, AM and Griffin, HG eds) pp 365–389, Humana Press, Clifton). Thus, residues identified in this manner are also "equivalent residues".

It will be appreciated that in the case of truncated forms of SGK or in forms where simple replacements of amino acids have occurred it is facile to identify the "equivalent residue".

The sequence for human SGK1 is given, for example, in Webster et al (1993) *Mol cell Biol* 13(4), 2031–2040.

It will be appreciated that identification of the residue equivalent to Thr 256, for example, may depend on the alignment of surrounding conserved residues.

A further aspect of the invention is a method of activating SGK (as defined above) wherein SGK is phosphorylated on the residue equivalent to Ser422 of full-length human SGK. SGK (for example full-length human SGK and ΔN-SGK (61–431), may be phosphorylated on the residue equivalent to Ser 422 of full-length human SGK1 by a preparation containing PDK2 activity. SGK may be activated by phosphorylation on this residue, as described in Example 1. The method may be performed in a cell, for example a mammalian cell that is stimulated by, for example, IGF-1 and/or hydrogen peroxide. The method may comprise culturing a host cell comprising a recombinant polynucleotide or a replicable vector which encodes SGK, stimulating the cell, for example with IGF-1 and/or hydrogen peroxide and isolating said polypeptide from said host cell. Methods of cultivating host cells and isolating recombinant proteins are well known in the art.

The residue equivalent to Ser422 or other residue of full-length human SGK1 may be identified by methods analagous to those described above for the residue equivalent to Thr256 of full-length human SGK1. Ser422 of human full-length SGK1 lies towards the C-terminus of the polypeptide.

A preparation containing PDK2 activity may phosphorylate polypeptides comprising an amino acid sequence corresponding to the consensus sequence Phe-Xaa-Xaa-Phe/Tyr-Ser/Thr-Phe/Tyr (SEQ. ID. NO:45).

SGK may be phosphorylated on the residue equivalent to Ser422 of full-length human SGK1, for example in vitro, by a protein kinase that may not have the physiological characteristics of PDK2 or may not require the consensus sequence thought to be required by PDK2. Thus, in vitro, SGK may be phosphorylated by a protein kinase that may not phosphorylate SGK in a physiologically relevant manner in vivo and may not correspond to an activity identified as PDK2. This may be analagous to the phosphorylation in vitro of PKBα on the site equivalent to Ser422 of SGK (Ser473) by MAPKAP Kinase-2 (Alessi et al (1996) *EMBO J.* 15, 6541–6551). MAPKAP Kinase-2 does not require the consensus sequence identified as required by PDK2.

It will be appreciated that a protein kinase that is capable of phosphorylating the residue equivalent to Ser422 of full-length human SGK1 may be identified by methods similar to those described above and in Example 1 for identifying a protein kinase that may phosphorylate the residue equivalent to Thr256 of full-length human SGK1.

The phosphorylation of SGK may be PtdIns(3,4,5)P$_3$ dependent. In particular, the phosphorylation of the residue equivalent to Ser422, for example by a preparation containing PDK2 activity, may be PtdIns(3,4,5)P$_3$ dependent. Thus, in vivo, the phosphorylation of the residue equivalent to Ser422 may be dependent upon the activity of PtdIns 3-kinase.

The phosphorylation of SGK on the residue equivalent to Thr256 of full-length human SGK1 may be dependent upon the phosphorylation of the residue equivalent to Ser 422 of full-length human SGK1. Alternatively, if serine 422 is replaced by an aspartate residue, as described in Examples 1 and 5, then the phosphorylation of the residue equivalent to Thr256, for example by PDK1, may be potentiated. Thus, the phosphorylation of Thr256 may require that (or be enhanced if) the residue equivalent to Ser422 is phosphorylated or is replaced by an aspartate residue.

As discussed in Example 5, SGK2 may be phosphorylated at residues Ser279 and/or Ser334. Ser279 may be phosphorylated by SGK, for example SGK2, or PKB. It may be necessary for the SGK, for example SGK2, or PKB to be activated, for example by phosphorylation by PDK1. Ser334 may be phosphorylated by PDK1. SGK3 may be phosphorylated at residues Ser77 and/or Ser79. These residues may be phosphorylated by SGK, for example SGK3, or PKB. It may be necessary for the SGK, for example SGK3, or PKB to be activated, for example by phosphorylation by PDK1 but phosphorylation of Ser77 and Ser79 of SGK3 may take place in the absence of phosphorylation by PDK1.

A further aspect of the invention is a fusion polypeptide of SGK or a variant, fragment or derivative thereof. The fusion polypeptide may comprise, for example, a fragment of SGK or variant or derivative thereof wherein the residues equivalent to the N-terminal about 20, 30, 40, 50 or 60 amino acids of human full-length SGK1 are deleted. The fusion polypeptide may further comprise glutathione-S-transferase. The glutathione-S-transferase may be fused to the N-terminus or C-terminus of SGK or the said fragment variant or derivative thereof; preferably it is fused to the N-terminus, for example as shown in Examples 1 and 5.

It is particularly preferred that the fusion polypeptide has at least 5%, 10%, 15%, 20%, 25% or 30% of the enzyme activity of SGK, for example SGK1, with respect to the phosphorylation of Crosstide (GRPRTSSFAEG (SEQ. ID. NO:30); see Example 1). It is more preferred if the fusion polypeptide has at least 50%, preferably at least 70% and more preferably at least 90% of the enzyme activity of SGK with respect to the phosphorylation of Crosstide. It is preferred that the fusion polypeptide comprises the residue equivalent to Thr256 and/or the residue equivalent to Ser 422 of full-length human SGK1. It will be appreciated that a fusion polypeptide with low enzymic activity may be useful in applications including high throughput screening, for example if it is expressed in high amounts or may be easily purified or stored. However, it will be appreciated that fusion polypeptides which are devoid of enzymatic activity may nevertheless also be useful, for example by interacting with another polypeptide, or as antigens in raising antibodies, or the phosphorylation of such variants or fusions or derivatives or fragments may be measured. It will be appreciated that fusions of PKBα, PKCδ, PKCξ, p70 S6 kinase, MSK1 and MSK2 are not polypeptides of the invention, unless they include all or part of SGK.

A further aspect of the invention is a polypeptide comprising the amino acid sequence of human SGK or a fragment, variant, derivative or fusion thereof wherein the residue equivalent to serine 422 of full-length human SGK1 is replaced (for example by an aspartate, glutamate or alanine residue) and/or the residue equivalent to threonine 256 of full-length human SGK1 is replaced (for example by an alanine residue), and/or the residue equivalent to lysine 127 of full-length human SGK1 is replaced (for example by an alanine residue). The residue equivalent to lysine 127 of full-length human SGK1 may be identified in a manner analogous to that described above for the residue equivalent to serine 422, and may lie in the ATP binding site. The residue equivalent to serine 422 of full-length human SGK1 may be replaced by a residue that is capable of carrying a negative charge (for example an aspartate or glutamate residue), which may mimic the effect of phosphorylation of serine 422. Alternatively, the residue equivalent to serine 422 of full-length human SGK1 may be replaced by a residue, for example alanine, that cannot be phosphorylated and is not capable of carrying a negative charge, and preferably is of a similar bulk to serine or threonine. The residue equivalent to threonine 256 of full-length human SGK1 may similarly be replaced by a residue that is capable of carrying a negative charge (for example an aspartate or glutamate residue), or by a residue, for example alanine, that cannot be phosphorylated and is not capable of carrying a negative charge and preferably is of a similar bulk to serine or threonine. The residue equivalent to lysine 127 of full-length human SGK1 may be replaced by a residue that is not capable of carrying a positive charge, for example an alanine residue.

It is preferred that the residue equivalent to serine 422 of full-length human SGK1 is replaced by an aspartate residue and the residues equivalent to threonine 256 and lysine 127 of the full-length human SGK1 are unmutated, ie are threonine and lysine respectively. It is further preferred that the amino acids equivalent to the N-terminal 20, 30, 40, 50 or 60 amino acids of full-length human SGK1 are not present, ie are deleted in relation to SGK1, SGK2β or SGK3. It will be appreciated that human SGK2α does not have an amino acid sequence equivalent to the N-terminal 60 amino acids of full-length human SGK1. It will further be appreciated that this may have the consequence that the interaction with a cellular component may not be the same for human SGK2α as for other SGKs, for example SGK1, SGK2β or SGK3.

SGK2 is capable of being phosphorylated at Ser279 and Ser334, as well as Thr193. Thus, it may alternatively or additionally be preferred that the residue equivalent to Ser279 and/or Ser334 of full length SGK2 is replaced by a residue that is capable of carrying a negative charge (for example an aspartate or glutamate residue), or by a residue, for example alanine, that cannot be phosphorylated and is not capable of carrying a negative charge and preferably is of a similar bulk to serine or threonine.

SGK3 is capable of being phosphorylated at Ser77 and Ser79. Thus, it may alternatively or additionally be preferred that the residue equivalent to Ser77 and/or Ser79 of full length SGK3 is replaced by a residue that is capable of carrying a negative charge (for example an aspartate or glutamate residue), or by a residue, for example alanine, that cannot be phosphorylated and is not capable of carrying a negative charge and preferably is of a similar bulk to serine or threonine.

It will be appreciated that phosphorylation of SGK2 at Ser279 and/or Ser334 or phosphorylation of SGK3 at Ser77 and/or Ser79 may modulate the activity or, for example, the cellular location of SGK2 or SKG3.

It will be appreciated that a polypeptide comprising the amino acid sequence of human SGK or a fragment, variant, derivative or fusion thereof wherein the residue equivalent to threonine 256 of full-length human SGK1 is replaced by an alanine residue, and/or the residue equivalent to lysine 127 of full-length human SGK1 is replaced by an alanine residue may not be capable of being activated by phosphorylation and/or may be devoid of protein kinase activity, respectively, and therefore may not be useful in screening methods of the invention.

A further aspect of the invention is a polynucleotide encoding a polypeptide of the invention, for example encoding SGK2 or SGK3 or encoding a variant or fragment or derivative of fusion of said SGK2 or SGK3 or a fusion of a said variant or fragment or derivative. Preferences and exclusions for the said polynucleotide variant are the same as in the first aspect of the invention, except that the following Expressed Sequence Tags (ESTs) are also excluded:

The polynucleotide may be a recombinant polynucleotide. The following Expressed Sequence Tags (ESTs) are excluded:

AA130828 (IMAGE Consortium, St Louis, Mo., USA); AI386362; AA790370; AA138663; AA219166 (related to SGK2)

AA219166 (related to SGK3).

All ESTs are identified by the Genbank accession number, as described in Examples 1 and 5.

The polynucleotide may be a vector suitable for replication and/or expression of the polypeptide in a mammalian/eukaryotic cell.

A still further aspect of the invention is a recombinant polynucleotide suitable for expressing a polypeptide of the invention. It is not considered that any of the ESTs listed above are polynucleotides as defined above; however, for the avoidance of doubt, the ESTs excluded above are further excluded from this aspect of the invention.

The polynucleotide or recombinant polynucleotide may be DNA or RNA, preferably DNA. The polynucleotide may or may not contain introns in the coding sequence; preferably the polynucleotide is or comprises a cDNA.

In one preferred embodiment the polynucleotide comprises the nucleotide sequence

```
GAAGAGGGCAGAGCCGTGCATGGGGCTGCTCCCCAGGACCTGAGCAGGAACCTGG    (SEQ. ID. NO:7)

AGTTTTCAGAGCTGCCTGATCATTGCTACAGAATGAACTCTAGCCCAGCTGGGAC

CCCAAGTCCACAGCCCTCCAGGGCCAATGGGAACATCAACCTGGGGCCTTCAGCC

AACCCAAATGCCCAGCCCACGGACTTCGACTTCCTCAAAGTCATCGGCAAAGGGA

ACTACGGGAAGGTCCTACTGGCCAAGCGCAAGTCTGATGGGGCGTTCTATGCAGT

GAAGGTACTACAGAAAAAGTCCATCTTAAAGAAGAAAGAGCAGAGCCACATCATG

GCAGAGCGCAGTGTGCTTCTGAAGAACGTGCGGCACCCCTTCCTCGTGGGCCTGC

GCTACTCCTTCCAGACACCTGAGAAGCTCTACTTCGTGCTCGACTATGTCAACGG

GGGAGAGCTCTTCTTCCACCTGCAGCGGGAGCGCCGGTTCCTGGAGCCCCGGGCC

AGGTTCTACGCTGCTGAGGTGGCCAGCGCCATTGGCTACCTGCACTCCCTCAACA

TCATTTACAGGGATCTGAAACCAGAGAACATTCTCTTGGACTGCCAGGGACACGT

GGTGCTGACGGATTTTGGCCTCTGCAAGGAAGGTGTAGAGCCTGAAGACACCACA

TCCACATTCTGTGGTACCCCTGAGTACTTGGCACCTGAAGTGCTTCGGAAAGAGC

CTTATGATCGAGCAGTGGACTGGTGGTGCTTGGGGGCAGTCCTCTACGAGATGCT

CCATGGCCTGCCGCCCTTCTACAGCCAAGATGTATCCCAGATGTATGAGAACATT

CTGCACCAGCCGCTACAGATCCCCGGAGGCCGGACAGTGGCCGCCTGTGACCTCC

TGCAAAGCCTTCTCCACAAGGACCAGAGGCAGCGGCTGGGCTCCAAAGCAGACTT

TCTTGAGATTAAGAACCATGTATTCTTCAGCCCCATAAACTGGGATGACCTGTAC

CACAAGAGGCTAACTCCACCCTTCAACCCAAATGTGACAGGACCTGCTGACTTGA

AGCATTTTGACCCAGAGTTCACCCAGGAAGCTGTGTCCAAGTCCATTGGCTGTAC
```

-continued

```
CCCTGACACTGTGGCCAGCAGCTCTGGGGCCTCAAGTGCATTCCTGGGATTTTCT
TATGCGCCAGAGGATGATGACATCTTGGATTGCTAGAAGAGAAGGACCTGTGAAA
CTACTGAGGCCAGCTGGTATTAGTAAGGAATTACCTTCAGCTGCTAGGAAGAGCG
ACTCAAACTAACAATGGCTTCAACGAGAAGCAGGTTTATTTTTTCCAGCACATAA
AAGAAAAATAATGTTTCGGAGTCCAGGACTGGCAGGACAGGTCATCAGATACTCA
GAGGCTGTATCTCTGCCCTGCCAACCTTGACAAATGGCTTCCAATGTTAGGTTTG
CTACAAGATGGTTACTGGAGCTCTAGCTGCCTATTTTGTGTTTAGGGAAGGGAAA
ATGGAGGAAAGGGGAGAAGAGCAAAGGGCGCTTTTAAAGAGCTTTCCCAAAAGCT
CCCCCCAATGACTTTTGCTTCCATCTCACTAACCACCCACCCCTACCTGGAATGG
AGGCTGGGAAATGTGGCTTATTTGCTGGGTACGTGACTATCCCTAATAACAAAGG
GGTTTTGACCCTAAGACATTAGGGGAGAATGTTGGGTAGGCAGCCAGCCCTCTTT
TACCATAGGGCCTCCTGGTGTTTGGATTTTGATCTCAATGTGTAAAATGACAGAG
ATGTAACAAGCTCATAGGGTATCAATATCTCTTATTGTTCTATGTTGAAAAAAAA
AAAAAAAAAAAAAAAAAAA
``` or

```
ATGGGTTCAGACTTTATGCCCTGAAAAGATCCTTCCAGCCCTGGCCATCTTGGAC   (SEQ. ID. NO:5)
TTCTGGAGCTACCCTGGCTCACAGGGGTCTTGTTGCCCTGGGTGTCCCCAGTTCT
TGAAAAGAATCAGCCTGGGAGGGGCCACACCCTGACCATCCCCCTTTATCCCTTC
TGAGATGTTTGTTAGGAAGTCTGGGTCCAGGGGATATCATTTCTTGTTCCATCCA
TGCAGGGGTTGCTTACCTCGGGTAGGAAACCCTCAGGCGGTGGCAGGTGCACAGG
TAGGGGAGGATGGAGAGGGCAGTGGTGCCTGAAGCCCTGGATGGGCGGAGCTGAC
CCCCCAACACCAACTCTATCATGCCTGCTCCTCCCTGTCCCCCCAGAGCTGCCTG
ATCATTGCTACAGAATGAACTCTAGCCCAGCTGGGACCCCAAGTCCACAGCCCTC
CAGGGCCAATGGGAACATCAACCTGGGGCCTTCAGCCAACCCAAATGCCCAGCCC
ACGGACTTCGACTTCCTCAAAGTCATCGGCAAAGGGAACTACGGGAAGGTCCTAC
TGGCCAAGCGCAAGTCTGATGGGCGTTCTATGCAGTGAAGGTACTACAGAAAAA
GTCCATCTTAAAGAAGAAAGAGCAGAGCCACATCATGGCAGAGCGCAGTGTGCTT
CTGAAGAACGTGCGGCACCCCTTCCTCGTGGGCCTGCGCTACTCCTTCCAGACAC
CTGAGAAGCTCTACTTCGTGCTCGACTATGTCAACGGGGAGAGCTCTTCTTCCA
CCTGCAGCGGGAGCGCCGGTTCCTGGAGCCCCGGGCCAGGTTCTACGCTGCTGAG
GTGGCCAGCGCCATTGGCTACCTGCACTCCCTCAACATCATTTACAGGGATCTGA
AACCAGAGAACATTCTCTTGGACTGCCAGGGACACGTGGTGCTGACGGATTTTGG
CCTCTGCAAGGAAGGTGTAGAGCCTGAAGACACCACATCCACATTCTGTGGTACC
CCTGAGTACTTGGCACCTGAAGTGCTTCGGAAAGAGCCTTATGATCGAGCAGTGG
ACTGGTGGTGCTTGGGGGCAGTCCTCTACGAGATGCTCCATGGCCTGCCGCCCTT
CTACAGCCAAGATGTATCCCAGATGTATGAGAACATTCTGCACCAGCCGCTACAG
ATCCCCGGAGGCCGGACAGTGGCCGCCTGTGACCTCCTGCAAAGCCTTCTCCACA
AGGACCAGAGGCAGCGGCTGGGCTCCAAAGCAGACTTTCTTGAGATTAAGAACCA
TGTATTCTTCAGCCCCATAAACTGGGATGACCTGTACCACAAGAGGCTAACTCCA
CCCTTCAACCCAAATGTGACAGGACCTGCTGACTTGAAGCATTTTGACCCAGAGT
```

-continued

```
TCACCCAGGAAGCTGTGTCCAAGTCCATTGGCTGTACCCCTGACACTGTGGCCAG

CAGCTCTGGGGCCTCAAGTGCATTCCTGGGATTTTCTTATGCGCCAGAGGATGAT

GACATCTTGGATTGCTAGAAGAGAAGGACCTGTGAAACTACTGAGGCCAGCTGGT

ATTAGTAAGGAATTACCTTCAGCTGCTAGGAAGAGCGACTCAAACTAACAATGGC

TTCAACGAGAAGCAGGTTTATTTTTTCCAGCACATAAAAGAAAAATAATGTTTCG

GAGTCCAGGACTGGCAGGACAGGTCATCAGATACTCAGAGGCTGTATCTCTGCCC

TGCCAACCTTGACAAATGGCTTCCAATGTTAGGTTTGCTACAAGATGGTTACTGG

AGCTCTAGCTGCCTATTTTGTGTTTAGGGAAGGGAAAATGGAGGAAAGGGGAGAA

GAGCAAAGGGCGCTTTTAAAGAGCTTTCCCAAAAGCTCCCCCCAATGACTTTTGC

TTCCATCTCACTAACCACCCACCCCTACCTGGAATGGAGGCTGGGAAATGTGGCT

TATTTGCTGGGTACGTGACTATCCCTAATAACAAAGGGGTTTTGACCCTAAGACA

TTAGGGGAGAATGTTGGGTAGGCAGCCAGCCCTCTTTTACCATAGGGCCTCCTGG

TGTTTGGATTTTGATCTCAATGTGTAAAATGACAGAGATGTAACAAGCTCATAGG

GTATCAATATCTCTTATTGTTCTATGTTGAAAAAAAAAAAAAAAAAAAAAAAAAA

A
``` or a variant, fragment, fusion or derivative thereof. The first nucleotide sequence encodes SGK2α and the second encodes SGK2β. The nucleotide sequences are shown in FIG. 1 together with the translations of the relevant open reading frames.

In another preferred embodiment the polynucleotide comprises the nucleotide sequence

```
GGTGTGCTCTTGAGGGATTAAATGCAAAGAGATCACACCATGGACTACAAG       (SEQ. ID. NO:6)

GAAAGCTGCCCAAGTGTAAGCATTCCCAGCTCCGATGAACACAGAGAGAAA

AAGAAGAGGTTTACTGTTTATAAAGTTCTGGTTTCAGTGGGAAGAAGTGAA

TGGTTTGTCTTCAGGAGATATGCAGAGTTTGATAAACTTTATAACACTTTA

AAAAAACAGTTTCCTGCTATGGCCCTGAAGATTCCTGCCAAGAGAATATTT

GGTGATAATTTTGATCCAGATTTTATTAAACAAAGACGAGCAGGACTAAAC

GAATTCATTCAGAACCTAGTTAGGTATCCAGAACTTTATAACCATCCAGAT

GTCAGAGCATTCCTTCAAATGGACAGTCCAAAACACCAGTCAGATCCATCT

GAAGATGAGGATGAAAGAAGTTCTCAGAAGCTACACTCTACCTCACAGAAC

ATCAACCTGGGACCGTCTGGAAATCCTCATGCCAAACCAACTGACTTTGAT

TTCTTAAAAGTTATTGGAAAAGGCAGCTTTGGCAAGGTTCTTCTTGCAAAA

CGGAAACTGGATGGAAAATTTTATGCTGTCAAAGTGTTACAGAAAAAAATA

GTTCTCAACAGAAAAGAGCAAAAACATATTATGGCTGAACGTAATGTGCTC

TTGAAAAATGTGAAACATCCGTTTTTGGTTGGATTGCATTATTCCTTCCAA

ACAACTGAAAAGCTTTATTTTGTTCTGGATTTTGTTAATGGAGGGGAGCTT

TTTTTCCACTTACAAAGAGAACGGTCCTTTCCTGAGCACAGAGCTAGGTTT

TACGCTGCTGAAATTGCTAGTGCATTGGGTTACTTACATTCCATCAAAATA

GTATACAGAGACTTGAAACCAGAAAATATTCTTTTGGATTCAGTAGGACAT

GTTGTCTTAACAGATTTTGGGCTTTGTAAAGAAGGAATTGCTATTTCTGAC
```

-continued

```
ACCACTACCACATTTTGTGGGACACCAGAGTATCTTGCACCTGAAGTAATT

AGAAAACAGCCCTATGACAATACTGTAGATTGGTGGTGCCTTGGGCTGTT

CTGTATGAAATGCTGTATGGATTGCCTCCTTTTTATTGCCGAGATGTTGCT

GAAATGTATGACAATATCCTTCACAAACCCCTAAGTTTGAGGCCAGGAGTG

AGTCTTACAGCCTGGTCCATTCTGGAAGAACTCCTAGAAAAAGACAGGCAA

AATCGACTTGGTGCCAAGGAAGACTTTCTTGAAATTCAGAATCATCCTTTT

TTTGAATCACTCAGCTGGGCTGACCTTGTACAAAAGAAGATTCCACCACCA

TTTAATCCTAATGTGGCTGGACCAGATGATATCAGAAACTTTGACACAGCA

TTTACAGAAGAAACAGTTCCATATTCTGTGTGTGTATCTTCTGACTATTCT

ATAGTGAATGCCAGTGTATTGGAGGCAGATGATGCATTCGTTGGTTTCTCT

TATGCACCTCCTTCAGAAGACTTATTTTTGTGAGCAGTTTGCCATTCAGAA

ACCATTGAGCAAAATAAGTCTATAGATGGGACTGAAACTTCTATTTGTGTGA

ATATATTCAAATATGTATAACTAGTGCCTCATTTTTATATGTAATGATGAAAACT

ATGAAAAAATGTATTTTCTTCTATGTGCAAGAAAAATAGGGCATTTCAAAGAGCT

GTTTTGATTAAAATTTATATTCTTGTTTAATAAGCTTATTTTTAAACAATTTAAA

AGCTATTATTCTTAGCATTAACCTATTTTTAAAGAAACCTTTTTTGCTATTGACT

GTTTTTTCCCTCTAAGTTTACACTAACATCTACCCAAGATAGACTGTTTTTTAAC

AGTCAATTTCAGTTCAGCTAACATATATTAATACCTTTGTAACTCTTTGCTATGG

CTTTTGTTATCACACCAAAACTATGCAATTGGTACATGGTTGTTTAAGAAGAAAC

CGTATTTTTCCATGATAAATCACTGTTTGAAATATTTGGTTCATGGTATGATCGA

AATGTAAAAGCATAATTAACACATTGGCTGCTAGTTAACAATTGGAATAACTTTA

TTCTGCAGATCATTTAAGAAGTAACAGGCCGGGCGCGGTGGCTCACGCCTGTAAT

CCCAGCACTTTGGGAGGCTGAGGCGGGCAGATCACCTGAGGTCAGGAGTTGGAGA

CCAGCCTGACCAACATGGACAAACCCCGTCTCTACTAAAAATACAAAATTGGCAG

GGTGTGGTGGCACATGCCTATAATCCCAGCTACTTGGGAGGCTAAGGCAGGAGAA

TCGCTTGAACCCGGGAGGCGGAGGTTGCAGTGAGCCGAGATCGCACCATTGCACT

CCTGCCTGGGCAACAAGAGTGAAACTCCATCTCCAAAAAAAAAAAAAAAAAA
``` or a variant, fragment, fusion or derivative thereof. The nucleotide sequence encodes SGK3 and is shown in FIG. 2 together with the translation of the relevant open reading frame.

Site-directed mutagenesis or other techniques can be employed to create single or multiple mutations, such as replacements, insertions, deletions, and transpositions, as described in Botstein and Shortle, ☐Strategies and Applications of In Vitro Mutagenesis,☐ *Science*, 229: 193–210 (1985), which is incorporated herein by reference. Polymerase chain reaction based methods of site-directed mutagenesis may be used, as well known to those skilled in the art, for example as described in Example 1.

By "suitable for expressing" is mean that the polynucleotide is a polynucleotide that may be translated to form the polypeptide, for example RNA, or that the polynucleotide (which is preferably DNA) encoding the polypeptide of the invention is inserted into an expression vector, such as a plasmid, in proper orientation and correct reading frame for expression. The polynucleotide may be linked to the appropriate transcriptional and translational regulatory control nucleotide sequences recognised by any desired host; such controls may be incorporated in the expression vector.

Characteristics of vectors suitable for replication in mammalian/eukaryotic cells are well known to those skilled in the art, and examples are given below. It will be appreciated that a vector may be suitable for replication in both prokaryotic and eukaryotic cells.

A variety of methods have been developed to operably link polynucleotides, especially DNA, to vectors for example via complementary cohesive termini. Suitable methods are described in Sambrook et al (1989) *Molecular Cloning, A Laboratory Manual*, Cold Spring Harbor Laboratory, Cold Spring Harbor, N.Y.

A desirable way to modify the DNA encoding a polypeptide of the invention is to use the polymerase chain reaction as disclosed by Saiki et al (1988) *Science* 239, 487–491. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker, all of which are incorporated herein by reference.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

It will be appreciated that the host cell, for example a mammalian cell such as 293 cells as described in Example 1 or Example 5, may be stimulated, for example using IGF-1 of hydrogen peroxide, such that the SGK polypeptide may be phosphorylated and/or activated in the host cell. The activated SGK polypeptide may then be recovered, if necessary in the presence of phosphatase inhibitors, for example microcystin, for example as described in Example 1. Recovery may entail purification on glutathione-Sepharose, as described in Example 1.

293 cells are human transformed primary embryonal kidney cells that may be obtained from the American Type Culture Collection (ATCC), 12301 Parklawn Drive, Rockville, Md. 20852–1776; catalogue reference ATCC CRL 1573.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells.

The vectors include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403406 and pRS413416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413–416 are Yeast Centromere plasmids (YCps).

The present invention also relates to a host cell transformed with a polynucleotide vector construct of the present invention. The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic cell line. Yeast host cells include YPH499, YPH500 and YPH501 which are generally available from Stratagene Cloning Systems, La Jolla, Calif. 92037, USA. Preferred mammalian host cells include human embryonic kidney 293 cells (see Example 1), Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104–109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cell, bacterial cells, insect cells and vertebrate cells.

For example, many bacterial species may be transformed by the methods described in Luchansky et al (1988) *Mol. Microbiol.* 2, 637–646 incorporated herein by reference. The greatest number of transformants is consistently recovered following electroporation of the DNA-cell mixture suspended in 2.5× PEB using 6250 V per cm at 25:FD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

A further aspect of the invention provides a method of making the polypeptide of the invention the method comprising culturing a host cell comprising a recombinant polynucleotide or a replicable vector which encodes said polypeptide, and isolating said polypeptide from said host cell. Methods of cultivating host cells and isolating recombinant proteins are well known in the art.

A still further aspect of the invention provides a method of making and activating the polypeptide of the invention the method comprising culturing a host cell, preferably a eukaryotic cell, comprising a recombinant polynucleotide or a replicable vector which encodes said polypeptide, stimulating the cell, for example with IGF-1 and/or hydrogen peroxide and isolating said polypeptide from said host cell. Methods of cultivating host cells and isolating recombinant proteins are well known in the art. The host cell may be a mammalian cell that is stimulated by, for example, IGF-1 and/or hydrogen peroxide, for example a 293 cell.

A further aspect of the invention is a polypeptide obtainable by the above methods of the invention.

A still further aspect of the invention is a method of identifying a compound that modulates the activity of SGK wherein activated SGK is used.

A further aspect of the invention is the use of activated SGK in a screening assay for a drug-lie compound or lead compound for the development of a drug-like compound. It will be appreciated that by a drug-like compound or lead compound for the development of a drug-like compound are included compounds that may be useful in medicine and compounds that may be useful in the development of a compound that may be useful in medicine. Examples of such screening assays may include the methods of the invention described below.

A further aspect of the invention is a method of identifying a compound that modulates the activity of SGK (as defined above), the method comprising contacting a compound with SGK and determining whether the activity of the said polypeptide is changed compared to the activity of the said SGK in the absence of said compound wherein the activity of SGK is measured by measuring the phosphorylation by SGK, in the presence of a suitable phosphate donor, of a polypeptide comprising an amino acid sequence corresponding to the consensus sequence (Arg/Lys; preferably Arg)-X-(X/Arg)-X-X-(Ser/Thr)-Z (SEQ. ID. NO:49) wherein X indicates any amino acid, X/Arg indicates any amino acid, with a preference for arginine, and Z indicates that the amino acid residue is preferably a hydrophobic residue. The polypeptide may be Crosstide or other suitable polypeptide described in Table 1 or Table 2 or preferably a physiological substrate of SGK, which may be GSK3. It will be appreciated that SGK2 and SGK3 may be capable of autophosphorylation. In particular, SGK2 comprises a sequence corresponding to the above consensus sequence, surrounding Ser279; thus the polypeptide may be SGK2 or SGK3 or a fragment of either that comprises a potential autophosphorylation site, as discussed in Example 1, ie Ser279 of SGK2 or Ser77 or Ser 79 of SGK3.

It will be appreciated that in the methods of the invention wherein phosphorylation of a polypeptide may occur that the presence of a suitable phosphate donor may be required, as described for the above aspect of the invention. Suitable phosphate donors will be known to those skilled in the art and include ATP, for example as the magnesium salt (MgATP), as described in Example 1.

It is preferred for at least the above three aspects of the invention that the SGK is full-length human SGK or N-terminally truncated SGK (for example, 20, 30, 40, 50 or 60 amino acids of full-length human SGK, for example full-length human SGK1, may be deleted, such as in ΔN-SGK (61–431)) or a fusion (preferably a GST fusion) of full-length human SGK or N-terminally truncated SGK wherein the residue equivalent to serine 422 of full-length human SGK1 is replaced by an aspartate residue and the residues equivalent to threonine 256 and lysine 127 of the full-length human SGK1 are unmutated, ie remain as threonine and lysine respectively.

It is preferred that the SGK is activated by phosphorylation according to a method of the invention. It will be appreciated that if the SGK is an SGK in which the residue equivalent to serine 422 of full-length human SGK1 is replaced by an aspartate residue, for example the preferred SGK described above, that this residue will not be phosphoryated, but that the SGK may be activated by phosphorylation of the residue (preferably threonine) equivalent to threonine 256 of full-length human SGK1.

It will be appreciated that the SGK may be phosphorylated and/or activated in a cell by stimulating the said cell with, for example, IGF-1 or hydrogen peroxide. The cell may be an eukaryotic, preferably mammalian, for example, 293 cell in which a recombinant SGK is expressed. The SGK may be recovered and purified as described in Example 1, for example using glutathione sepharose (for a GST-SGK fusion polypeptide), as described above and in Examples 1 and 5.

In an embodiment of the above methods, the compound may act by interacting with the polypeptide of the invention and modulating, ie inhibiting or enhancing, its activation by, for example, PDK1 and/or a preparation containing PDK2 activity or other activating protein kinase or protein kinases.

It will be understood that it will be desirable to identify compounds that may modulate the activity of the polypeptide in vivo. Thus it will be understood that reagents and conditions used in the method may be chosen such that the interactions between the said SGK and its activating protein kinase or protein kinases are substantially the same as between human SGK and its activating protein kinase or protein kinases in vivo, which may be PDK1 and a polypeptide with PDK2 activity. Thus, it may be preferred that the activating protein kinase used in the assay is a physiological activating protein kinase of SGK, for example PDK1 or functional equivalent thereof and/or a preparation containing PDK2 activity for which interactions between the said SGK and the functional equivalent are substantially the same as between human SGK and the said physiological activating protein kinase. It will be appreciated that the compound may bind to the SGK or may bind to an activating protein kinase.

By a functional equivalent of a physiological activating protein kinase of SGK, for example PDK1, is meant a protein kinase with substantially the same substrate specificity as the physiological activating protein kinase, for example PDK1 (ie capable of phosphorylating the underlined residue in the consensus sequence B-T-F-C-G-T-(P/I)-(D/E)-Y-(L/I/M)-A-P-E (SEQ. ID. NO:48), where B is a basic residue), and/or capable of phosphorylating SGK on the same residue as the said physiological activating protein kinase.

It will be understood that it will be desirable to identify compounds that may modulate the activity of the polypeptide in vivo. Thus it will be understood that reagents and conditions used in the method may be chosen such that the interactions between the said SGK and its substrate are substantially the same as between human SGK and its substrate or substrates in vivo. Thus, it may be preferred that the substrate used in the assay is a physiological substrate of SGK or a fragment, variant, derivative or fusion thereof or fusion of a said fragment, variant or derivative (defined in an analagous manner to the definitions given above in relation to SGK) for which interactions between the said SGK and the said fragment, variant, derivative or fusion are substantially the same as between human SGK and the said physiological substrate. An example of a substrate of SGK, for example SGK1, is GSK3.

Physiological substrates of SGK may include substrates identified, for example in overexpression studies referred to in Example 1, as physiological substrates for PKB. The finding presented here concerning the activation and substrate specificity of SGK and its similarity to the activation and substrate specificity of PKB may indicate that substrates previously identified as physiological substrates for PKB may additionally or alternatively be physiological substrates for SGK, for example SGK1, SGK2 and/or SGK3.

PKB has been thought to mediate a number of the actions of insulin, including stimulation of glucose and amino acid uptake, glycogen and protein synthesis and cardiac muscle glycolysis (reviewed in [7, 8]) as well as regulation of the transcription of specific genes [9, 10]. Secondly, the PKBβ isoform is overexpressed in a significant percentage of ovarian and pancreatic cancers [11, 12] and the PKBα isoform in some breast cancers [2]. It appears that PKB or SGK may be capable of providing a survival signal that protects cells from apoptosis induced in a variety of ways (reviewed in [8, 13]). The activation of PKB or SGK by gene amplification and other mechanisms may therefore contribute to the generation of malignancies that are able to flourish in the absence of extracellular survival signals.

PKB phosphorylates proteins and peptides at serine and threonine residues that lie in Arg-Xaa-Arg, -Xaa-Xaa-Ser/Thr- (SEQ. ID. NO:46) sequences [14]. In insulin signal transduction two physiological substrates of PKB appear to be the protein kinase-glycogen synthase kinase-3 (GSK3) [15, 16] and the cardiac isoform of phosphofructokinase-2 (PFK2) [8, 17]. Phosphorylation by PKB inhibits GSK3 activity leading to dephosphorylation and activation of glycogen synthase and protein synthesis initiation factor eIF2B [18]. We show here that SGK is as effective in vitro at inactivating GSK3 as PKB. However, factors including the relative levels of PKB and SGK detected in appropriate tissues, suggest that PKB may be more important in the regulation of GSK3 than SGK.

Dephosphorylation and activation of glycogen synthase and protein synthesis initiation factor eIF2B [18] may contribute to the insulin-induced stimulation of glycogen synthesis and protein synthesis, respectively. PKB activates cardiac PFK2, which seems to underlie the insulin-induced stimulation of glycolysis in the heart. In the protection of cells against apoptosis, BAD appears to be one of the physiological substrates of PKB (and may therefore also be a physiological substrate of SGK). This protein, in its dephosphorylated form, interacts with the Bcl family member $Bcl_{XL}$, thereby inducing apoptosis in some cells. However, when PKB phosphorylates BAD at Ser136, it dissociates from $Bcl_{XL}$, interacts with 14-3-3 proteins instead, and apoptosis is prevented [19]. Thus, the polypeptide BAD, which may be involved in control of apoptosis, may be a physiological substrate of SGK, for example SGK1, 2 and/or 3.

In one embodiment, the compound decreases the activity of said SGK polypeptide. For example, the compound may bind substantially reversibly or substantially irreversibly to the active site of said polypeptide. In a further example, the compound may bind to a portion of said polypeptide that is not the active site so as to interfere with the binding of the said polypeptide to its substrate. In a still further example, the compound may bind to a portion of said polypeptide so as to decrease said polypeptide's activity by an allosteric effect. This allosteric effect may be an allosteric effect that is involved in the natural regulation of the said polypeptide's activity, for example in the activation of the said polypeptide by an "upstream activator" such as PDK1 and/or PDK2 (or a preparation containing PKD2 activity).

In a further embodiment, the compound increases the activity of said polypeptide. For example, the compound may bind to a portion of said polypeptide that is not the active site so as to aid the binding of the said polypeptide to its substrate. In a still further example, the compound may bind to a portion of said polypeptide so as to increase said polypeptide's activity by an allosteric effect. This allosteric effect may be an allosteric effect that is involved in the natural regulation of the said polypeptide's activity for example in the activation of the said polypeptide by an "upstream activator" such as PDK1 and/or PDK2 (or a preparation containing PDK2 activity).

Conveniently, the method makes use of the fact that SGK phosphorylates Crosstide as described in Example 1, but any suitable substrate, for example a physiological substrate of SGK, may be used. Thus the phosphorylation of Crosstide may be measured using techniques well known to those skilled in the art.

Conveniently, the method makes use of an assay which may be substantially the same as that described in Example 1. In Example 1, phosphorylation of Crosstide by SGK is measured. It is preferred that the SGK is recombinant SGK.

Alternatively, a change in the activity of the substrate may be measured. This may be done in a whole cell system or using purified or partially purified components. Thus, it will be appreciated that the phosphorylation of the substrate may be measured by measuring a change in the activity of the substrate. For example, the substrate may be GSK3 and the phosphorylation of GSK3 may be measured by measuring the activity of GSK3, as described in Example 1. It will be appreciated that it may be necessary to determine the effect of the compound on the activity of the substrate, for example by measuring the activity of the substrate when exposed to the compound (1) after exposure of the substrate to SGK, (2) before exposure of the substrate to SGK and/or (3) without exposure to SGK.

Similarly, expression of a protein encoded by an RNA transcribed from a promoter regulated (directly or indirectly) by a substrate of SGK may be measured. Expression of leptin may be affected by PKB (Barthel et al (1997) *Endocrinol* 183, 3559–3562) and/or SGK. The expression of the ob gene product leptin in adipose tissues has been previously described to be regulated by insulin in vivo and vitro. A constitutively active version of PKB induced production of leptin in 3T3-L1 adipocytes, possibly via a non-transcriptional mechanism. Leptin expression therefore may be controlled by PKB and/or SGK.

Expression of IGF-1 binding protein may be affected by PKB (Cichy et al (1998) *J Biol Chem* 273, 6482–6487). Expression of phosphoenolpyruvate carboxykinase (PEPCK) may also be affected by PKB (Sutherland et al (1998) *J Biol Chem* 273, 3198–3204). The protein may be one that is physiologically regulated by a substrate of SGK or may be a "reporter" protein, as well known to those skilled in the art (ie a recombinant construct may be used). A reporter protein may be one whose activity may easily be assayed, for example β-galactosidase, chloramphenicol acetyltransferase or luciferase (see, for example, Tan et al (1996)).

A still further aspect of the invention provides a method of identifying a compound which binds to a substrate, preferably a physiological substrate, of SGK, as discussed above, which may be, for example, GSK3 or BAD, and either enhances or prevents its activation and/or phosphorylation by SGK, the method comprising determining whether a compound enhances or prevents the interaction of the said substrate with SGK or determining whether the compound substantially blocks phosphorylation and/or activation of the said substrate by SGK.

Suitable assays may be similar to those described above.

A further aspect of the invention is a method of identifying a compound which modulates (for example, inhibits or enhances) the activation of SGK by an interacting polypeptide, preferably a physiological interacting polypeptide, as discussed above, such as PDK1 or a polypeptide with PDK2 activity (which may be present in a preparation containing PDK2 activity), the method comprising determining whether a compound enhances or disrupts the interaction between (a) SGK and (b) the interacting polypeptide, such as PDK1 or a preparation containing PDK2 activity or a functional equivalent of PDK1 or PDK2, or determining whether the compound modulates (for example, enhances, or inhibits, including substantially blocks) activation of the said SGK by the interacting polypeptide, such as PDK1 or a functional equivalent thereof or a preparation containing PDK2 activity or a functional equivalent thereof.

Expression of PDK1 is described in Example 1, in which references are also given which describe the sequence of PDK1.

A still further aspect of the invention provides a method of identifying a polypeptide that interacts with activated SGK, the method comprising (1) contacting (a) the said SGK with (b) a composition that may contain a polypeptide that interacts with the said activated SGK, (2) detecting the presence of a complex containing the said SGK and a polypeptide, and optionally (3) identifying any polypeptide bound to the said protein kinase.

In one embodiment, the composition may comprise material from cells. In particular, the cells may be selected from the following types: (1) cells which do not express SGK even when stimulated, (2) cells which express SGK after exposure to a stimulus, but which have not been so exposed, (3) cells of type 2 after exposure to the stimulus and (4) cells of type 3 after exposure to a stimulus that activates SGK (for example exposure of 293 cells to hydrogen peroxide or IGF-1). Polypeptides that are found in a subset only of types 1–4 are of particular interest and may be characterised further. Such a polypeptide may be an activator of SGK. Alternatively, it may be an inactivator of SGK.

It will be appreciated that the method may be performed within a cell, for example using the yeast two hybrid system as is well known in the art. In this example, cDNAs copied from mRNA from the three cell types described above would be used.

It will further be appreciated that a transgenic animal in which a SGK gene is altered and/or a recombinant SGK gene is present, for example a rodent, in particular a mouse, may be useful in, for example, identifying a substrate of SGK, for example a substrate of SGK1, SGK2 and/or SGK3. A said transgenic animal in which each SGK gene present is altered may be particularly useful (for example, in which at least the SGK1, SGK2 and SGK3 genes are altered). It will be appreciated that a said transgenic animal in which one or more, including all, PKB genes are also altered and/or a recombinant PKB gene is present may also be useful.

Conveniently, the SGK used in a method of the invention is one which is produced by recombinant DNA technology ie is recombinant SGK. Similarly, it is preferred if the PDK1 or other "upstream activator" used in the method is one which is produced by recombinant DNA technology Similarly, it is preferred but not essential that the substrate, for example GSK3 or Crosstide, is produced by recombinant DNA technology or automated synthetic techniques, as well known to those skilled in the art. GSK3 may alternatively be purified from rabbit skeletal muscle (see Example 1 and references therein).

It will be appreciated that it may be necessary to activate the SGK prior to its use in assays. In a preferred embodiment the SGK is activated in vitro by treating the polypeptide with PDK1 and MgATP, as described in Examples 1 and 5. Recombinant or endogenous SGK may be activated in a cell, for example a 293 cell, for example by stimulation of the cell with IGF-1 or hydrogen peroxide, as described in Examples 1 and 5. It is particularly preferred if the SGK is the recombinant polypeptide produced according to the methods of the invention. It is still more preferred that the SGK is SGK in which the residue equivalent to serine 422 of full-length human SGK1 is replaced by an aspartate residue and the residues equivalent to threonine 256 and lysine 127 of the full-length human SGK1 remain as threonine and lysine respectively.

It will be appreciated that by "suitable" we mean that the said components in the method are those that have interactions or activities which are substantially the same as those of SGK or a physiological substrate of SGK or Crosstide or GSK3 or other substrates, or the upstream activator such as PDK1 as the case may be but which may be more convenient to use in an assay. For example, fusions of SGK and PDK1 are particularly useful since said fusion may contain a moiety which may allow the fusion to be purified readily.

It will be appreciated that the methods described may be performed in cells. "Reporter gene" constructs may be prepared by methods known to those skilled in the art, using the teaching herein. For example, a reporter gene construct may be made with a leptin gene promoter sequence or IGF-1 binding protein gene promoter sequence or other PKB and/or SGK-dependent promoter sequence. This construct may be introduced together with an SGK construct into a cell line, in the parent cell line of which leptin is activated in response to known stimuli, and in which the endogenous SGK gene or genes (and optionally the PKB gene or genes) have been inactivated. Alternatively the reporter gene construct could be introduced into the cell line in which SGK and a substrate of SGK is activated in response to known stimuli. The expression of the reporter gene will be dependent on the activity of SGK and thus the effect of compounds can be measured. In a further example, the reporter gene may be fatal to the cells, or alternatively may allow cells to survive under otherwise fatal conditions. Cell survival can then be measured, for example using colorimetric assays for mitochondrial activity, such as reduction of WST-1 (Boehringer). WST-1 is a formosan dye that undergoes a change in absorbance on receiving electrons via succinate dehydrogenase. In a further embodiment the yeast two-hybrid system is used.

The enhancement or disruption of the interaction between SGK and an interacting polypeptide as defined above, or suitable derivatives, fragments, fusions or variants can be measured in vitro using methods well known in the art of biochemistry and include any methods which can be used to assess protein-protein interactions.

The said interaction can also be measured within a cell, for example using the yeast two hybrid system as is well known in the art.

It will be appreciated that the invention provides screening assays for drugs which may be useful in modulating, for example either enhancing or inhibiting, the activity of SGK or its interactions with upstream activators. The compounds identified in the methods may themselves be useful as a drug or they may represent lead compounds for the design and synthesis of more efficacious compounds.

It will be appreciated that screening assays which are capable of high throughput operation will be particularly preferred. Examples may include the cell based assays described and protein-protein binding assays. A further example is an SPA-based (Scintillation Proximity Assay) system as described in Example 2.

The compound may be a drug-like compound or lead compound for the development of a drug-like compound for each of the above methods of identifying a compound. It will be appreciated that the said methods may be useful as screening assays in the development of pharmaceutical compounds or drugs, as well known to those skilled in the art.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons and which may be water-soluble. A drug-like compound may additionally exhibit features of selective interaction with a particular protein or proteins and be bioavailable and/or able to penetrate target cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise or has poor bioavailability) may provide a starting-point for the design of other compounds that may have more desirable characteristics.

It will be appreciated that screening assays which are capable of high throughput operation will be particularly preferred. Examples may include cell based assays and protein-protein binding assays. An SPA-based (Scintillation Proximity Assay; Amersham International) system may be used. For example, beads comprising scintillant and a substrate polypeptide, for example Crosstide or a peptide comprising the amino acid sequence of Crosstide may be prepared. The beads may be mixed with a sample comprising $^{32}$P or $^{33}$P-γ-labelled ATP, SGK (as defined above) and with the test compound. Conveniently this is done in a 96-well format. The plate is then counted using a suitable scintillation counter, using known parameters for $^{32}$P or $^{33}$P SPA assays. Only $^{32}$P or $^{33}$P that is in proximity to the scintillant, i.e. only that bound to Crosstide that is bound to the beads, is detected. Variants of such an assay, for example in which the substrate polypeptide is immobilised on the scintillant beads via binding to an antibody or antibody fragment, may also be used.

Other methods of detecting polypeptide/polypeptide interactions include ultrafiltration with ion spray mass spectroscopy/HPLC methods or other physical and analytical methods. Fluorescence Energy Resonance Transfer (FRET) methods, for example, well known to those skilled in the art, may be used, in which binding of two fluorescent labelled entities may be measured by measuring the interaction of the fluorescent labels when in close proximity to each other.

A further aspect of the invention is a kit of parts useful in carrying out a method, for example a screening method, of the invention. Such a kit may comprise SGK (as defined above), PDK1 or a functional equivalent thereof or a preparation containing PDK2 activity or a functional equivalent therof and/or a substrate of SGK, for example Crosstide or GSK3 or BAD.

A further aspect of the invention is a compound identifiable or identified by a method of the invention.

It is preferred that a compound of the invention does not modulate the activity or activation of PKB, for example PKBα, or of PDK1. Thus, it may be desirable to assess the effect of any compound identified by a screening method of the invention on the activity or activation of PKB, for example PKBα, or PDK1. Methods of assessing the effect of any compound on the activity or activation of PKB will be known to the person skilled in the art and may be similar to the methods described herein for assessing the effect of any compound on the activity or activation of SGK, with the substitution of PKB or suitable variant, fragment derivative or fusion or fusion of a suitable variant, fragment or derivative, as defined in an analagous manner to SGK, above, for SGK.

A further aspect of the invention is a method of identifying a substrate of SKG wherein a compound that modulates the activity of, for example inhibits, SGK but does not modulate the activity of, for example inhibit PKB, for example PKBα is used. For example, the method may be a method in which the effect of a compound that inhibits SGK but does not inhibit PDK1 on cellular metabolism is assessed. Thus, for example, the effect of such a compound on signalling events thought to be mediated by activation of PKBα may be assessed, as discussed in Example 1. It will be appreciated that such a method may be carried out in whole cells or on partially or semi-purified cellular components. Alternatively, a compound that modulates the activity of, for example inhibits, PKB, for example PKBα but does not modulate the activity of, for example inhibit SGK, for may be used in a method of identifying a substrate of SKG in a similar manner to that described above.

A still further aspect of the invention is a compound identifiable or identified by a method of the invention for use in medicine.

A further aspect of the invention is the use of a compound identifiable or identified by a method of the invention in the manufacture of a medicament for treatment of a patient in need of modulation of the activity of SGK, for example SGK1, SGK2 and/or SGK3.

It is preferred that the patient is mammalian. It is further preferred that the patient is human.

A compound that is capable of reducing the activity of SGK may be useful in treating cancer. PKB and/or SGK may be capable of providing a survival signal that protects cells from apoptosis induced in a variety of ways (reviewed in [8, 13]). Thus, such compounds may aid apoptosis. Reduction of the activity of SGK may promote apoptosis and may therefore be useful in treating cancer. Conditions in which aiding apoptosis may be of benefit may also include resolution of inflammation.

It will be appreciated that a patient in need of modulation of the activity of SGK2 may have a disease or condition that affects the liver, kidney, pancreas and/or brain.

A compound is capable of increasing the activity of SGK may be useful in treating diabetes or obesity, or may be useful in inhibiting apoptosis. Increased activity of PKB and/or SGK may lead to increased levels of leptin, as discussed above, which may lead to weight loss; thus such compounds may lead to weight loss. For example, such compounds may suppress apoptosis, which may aid cell survival during or following cell damaging processes. It is believed that such compounds are useful in treating disease in which apoptosis is involved. Examples of such diseases include, but are not limited to, mechanical (including heat) tissue injury or ischaemic disease, for example stroke and myocardial infarction, neural injury and myocardial infarction. Thus the patient in need of modulation of the activity of SK may be a patient with cancer or with diabetes, or a patient in need of inhibition of apoptosis, for example a patient suffering from tissue injury or ischaemic injury, including stroke.

Thus, a further aspect of the invention provides a method of treating a patient with an ischaemic disease the method comprising administering to the patient an effective amount of a compound identifiable by the screening methods of the invention.

A still further invention provides a use of a compound identifiable by the screening methods of the invention in the manufacture of a medicament for treating an ischaemic disease in a patient.

Thus, a further aspect of the invention provides a method of treating a patient with an ischaemic disease the method comprising administering to the patient an effective amount of a compound identifiable by the screening methods of the invention.

If the patient is a patient in need of promotion of apoptosis, for example a patient with cancer, it is preferred that the compound of the invention that is used in the preparation of the medicament is capable of reducing the activity of SGK. If the patient is a patient with diabetes or a patient in need of inhibition of apoptosis, for example a patient with ischaemic disease, it is preferred that the compound of the invention that is used in the preparation of the medicament is capable of increasing the activity of SGK.

It will be appreciated that a compound of the invention may be capable of modulating the activity of SGK1, SGK2 and/or SGK3 to different extents. It will be appreciated that it may be desirable to select a compound with a particular profile of activity against the above forms of SGK for a particular use. SGK2 mRNA is present at highest levels in liver, kidney, pancreas and brain, whereas mRNA encoding SGK1 and SGK3 is similar in all tissues tested. Thus, it may be important to select a compound that is capable of increasing the activity of SGK2 for use in the preparation of a medicament for treating ischaermic liver disease.

The aforementioned compounds of the invention or a formulation thereof may be administered by any conventional method including oral and parenteral (e.g. subcutaneous or intramuscular) injection. The treatment may consist of a single dose or a plurality of doses over a period of time.

Whilst it is possible for a compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Typically, the carriers will be water or saline which will be sterile and pyrogen free.

Thus, the invention also provides pharmaceutical compositions comprising the compound identifiable by the screening methods of the invention and a pharmaceutically acceptable carrier.

FIGURE LEGENDS

FIG. 1.

Amino acid sequences surrounding the activating phosphorylation sites on PKB, p70 S6 kinase and PKCζ and their similarity to the corresponding regions of SGK. The proposed consensus sequence is shown (SEQ ID NO: 45). Identities are shown in boldface type and the phosphorylated residues in PKB and p70 S6 kinase are underlined. The phosphorylation sites are separated by 160–165 residues in each enzyme.

FIG. 2. Expression and purification of SGK and PKB fusion proteins in 293 cells. GST fusion proteins expressed in 293 cells were purified on glutathione-Sepharose from 200 µg of cell lysate protein, subjected to electrophoresis on 5–20% (panel A) or 10% (panel B) SDS-polyacrylamide gels and stained with Coomassie Blue. Cells were transfected with the following constructs:—Lane 1, pEBG2T expressing GST; lanes 2 and 4, PEBG-SGK expressing full length SGK; lane 3, pEBG-PKBa expressing full length PKBα; lane 5 pEBG-ΔN-SGK(61–431) expressing the N-terminally truncated form of SGK. The marker proteins (lanes M) and their molecular masses are also shown.

FIG. 3. Activity of GST-SGK fusion proteins purified from unstimulated 293 cells. Wild type SGK and the mutants indicated were expressed in 293 cells and purified on glutathione-Sepharose. Each fusion protein (1 µg) was incubated for 20 min at 30° C. with protein phosphatase 2A (30 mU/ml) in 50 µl of 50 mM Tris/HCl pH 7.5, 0.1 mM EGTA, 0.1% (v/v) 2-mercaptoethanol. Where indicated (+), microcystin-LR (1 µM) was included prior to the addition of PP2A. In the other incubations (−) microcystin-LR was only added after treatment with the phosphatase. SGK activity was then measured using "Crosstide" as substrate.

FIG. 4. Phosphorylation and activation and of SGK by PDK1 in Vitro (A) GST-SGK (0.3 µg) was phosphorylated using GST-PDK1 (0.1 µg) and [γ-$^{32}$P] ATP (500 cpm/pmol) as described under Methods. Where indicated (+), 1 µM PtdIns(3,4,5)P$_3$ in lipid vesicles containing phosphatidylserine (100 µM) and phosphatidylcholine (100 µM) (PS/PC) were also included. The reactions were stopped by the addition of SDS to 2% and, after heating for 5 min at 95° C., the samples were subjected to electrophoresis on 10% SDS/polyacrylamide gels, stained with Coomasssie blue and then autoradiographed. The positions of the molecular mass markers are also indicated (B) Same as (A), except that unlabelled ATP was used instead of [γ-$^{32}$P] ATP. After incubation for 10 min at 30° C., 10 µl aliquots were assayed for SGK activity using Crosstide as substrate. The results are shown ±SD for three separate experiments.

Figure 5:
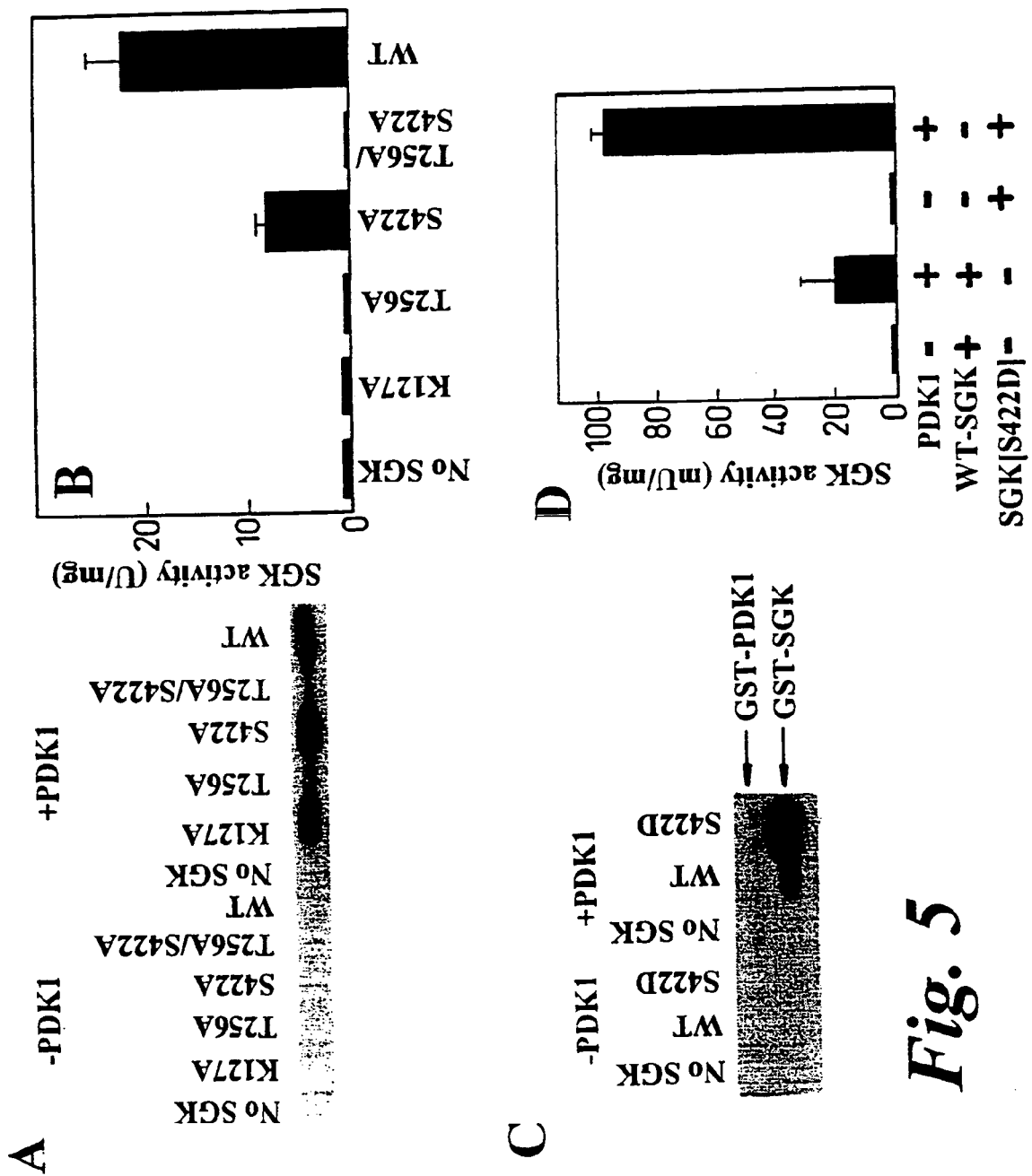

FIG. 5. Effect of mutations on the phosphorylation of SGK by PDK1 in vitro. (A) GST fusion proteins of wild type (WT) or mutant GSK (0.3 µg) were incubated with PP2A as described in the legend to FIG. 3 and, after the addition of microcystin-LR (1 µM) to inactivate the PP2A, the SGK proteins were incubated with [γ-$^{32}$P]ATP (500 cpm/pmol) with (+) and without (−) PDK1 (0.1 µg), subjected to SDS-PAGE, stained with Coomasssie blue and then autoradiographed. The Lys 127Ala mutation creates a catalytically inactive mutant. (B) Same as (A), except that unlabelled ATP was used instead of [γ-$^{32}$P] ATP (500 cpm/pmol). After incubation for 10 min at 30° C., 10 µl aliquots were assayed for SGK activity using Crosstide as substrate. The results are shown ±SD for three separate experiments. (C) GST fusion proteins of wild type SGK or the S422D mutant (1 µg) were incubated with PP2A and phosphorylated with PDK1 (0.2 µg) and [γ-$^{32}$P]ATP as in A, then subjected to SDS-PAGE followed by autoradiography. (D) Same as (C), except that unlabelled ATP was used instead of [γ-$^{32}$P]ATP. After incubation for 10 min at 30° C., aliquots of the reactions were assayed for SGK activity. The results are shown ±SD for three separate experiments.

Figure 6:
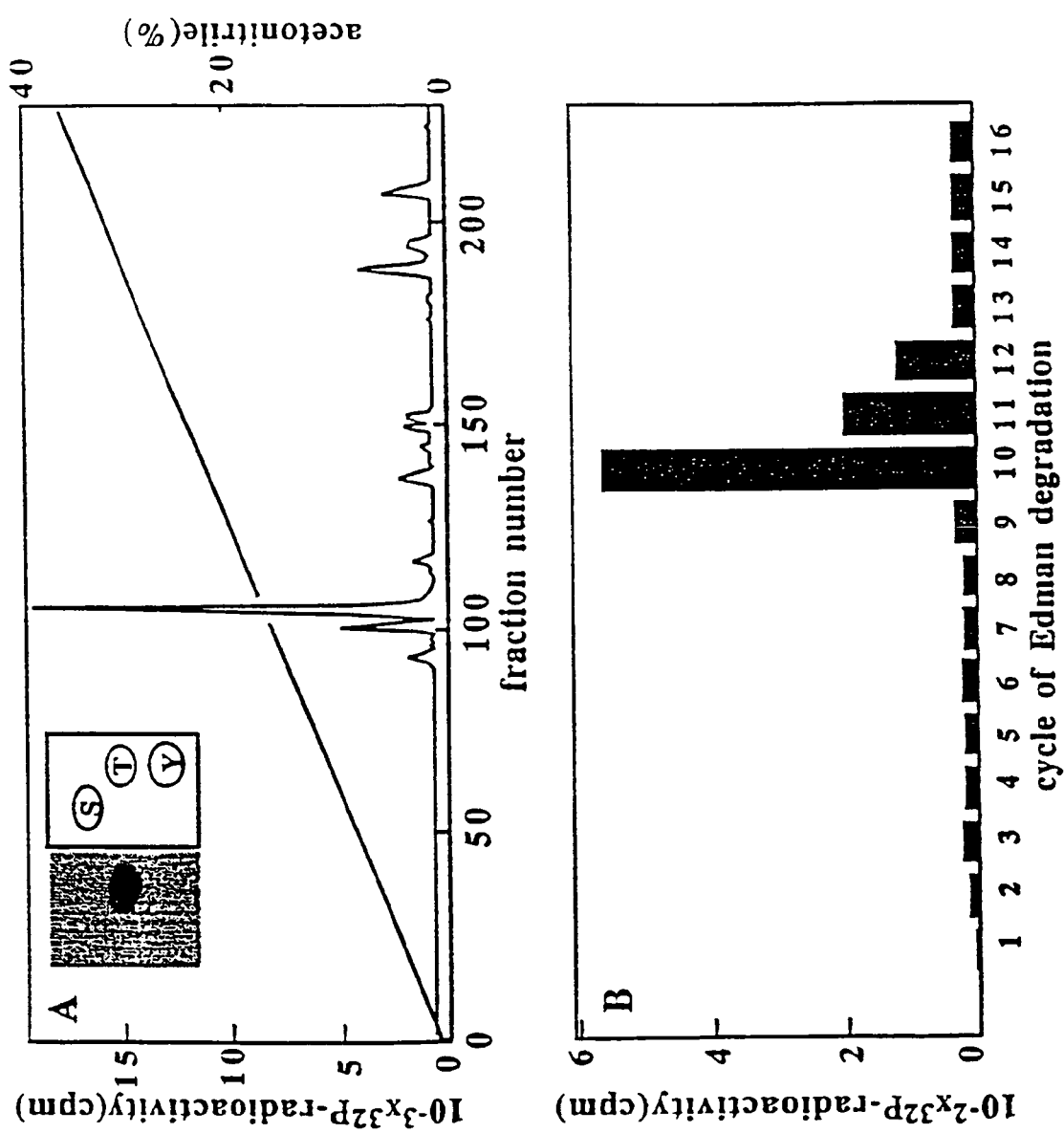

FIG. 6. Mapping the PDK1 phosphorylation site on SGK (A) GST-ΔN-SGK[S422D] (26 µg) was phosphorylated with PDK1 and digested with V8 protease as described under Methods. The digest was applied to a Vydac C18 column equilibrated in 0.1% (v/v) trifluoroacetic acid (TFA). The column was developed with a linear gradient of acetonitrile in 0.1% TFA at a flow rate of 0.8 ml/min and fractions of 0.4 ml were collected. $^{32}$P-radioactivity is shown by the full line and the acetonitrile gradient by the diagonal line. The inset shows phosphoamino acid analysis of the major $^{32}$P_labelled peptide. (B) An aliquot of the major phosphopeptide in panel A was analysed by solid-phase sequencing on an Applied Biosystems 470A sequencer [29] and $^{32}$P-radioactivity released after each cycle of Edman degradation was measured.

Figure 7:
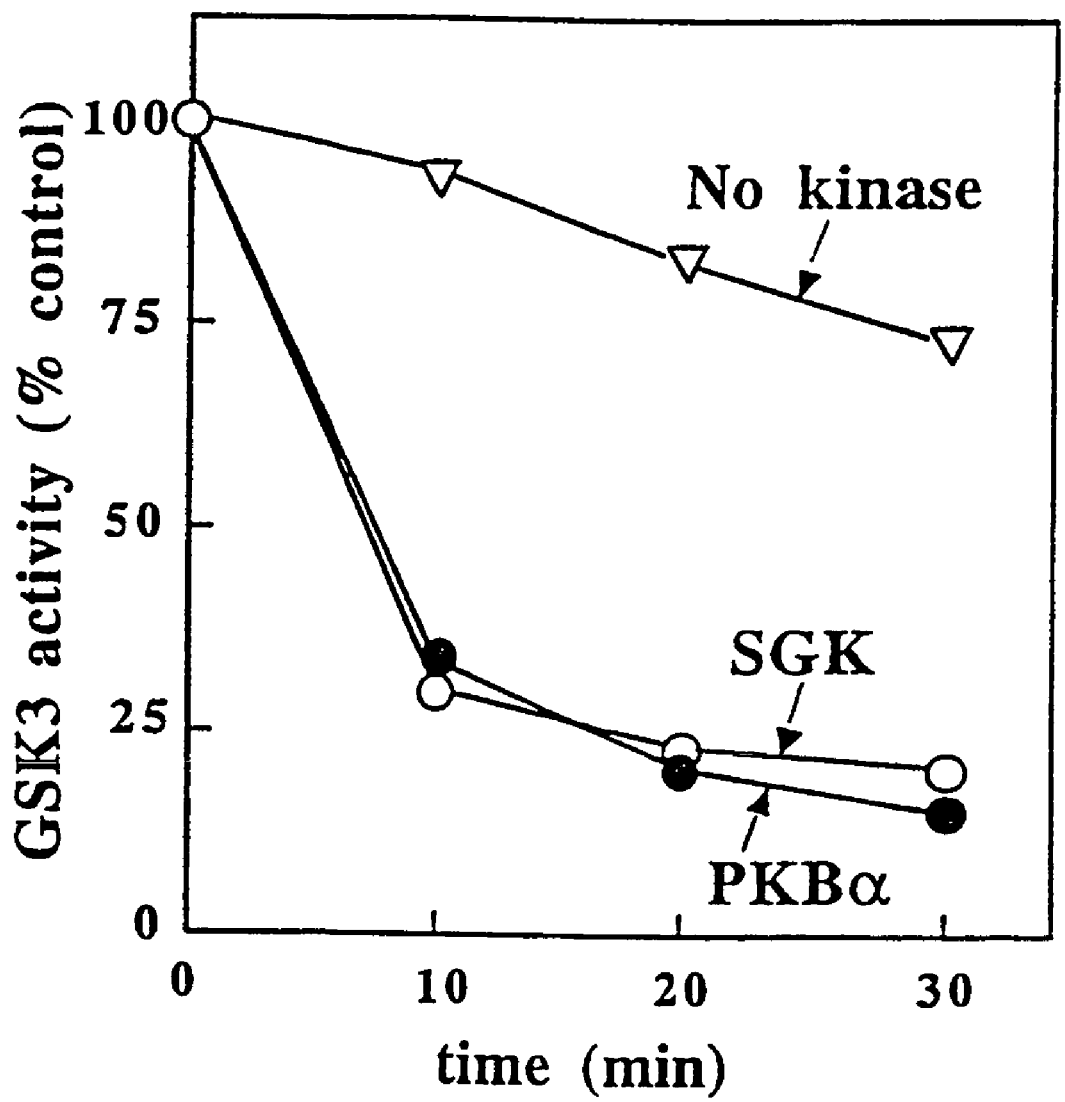

FIG. 7. SGK and PKBα inactivate GSK3 at similar rates. The incubations were carried out as described for peptide phosphorylation, except that GSK3 (50mU) purified from rabbit skeletal muscle replaced the peptide. Units of GSK3 activity are defined in [30]. At various times after incubation with MgATP alone (open triangles) and either SGK (open circles) or PKBα (closed circles) aliquots were removed and assayed for GSK3 activity as in [30].

Figure 8:
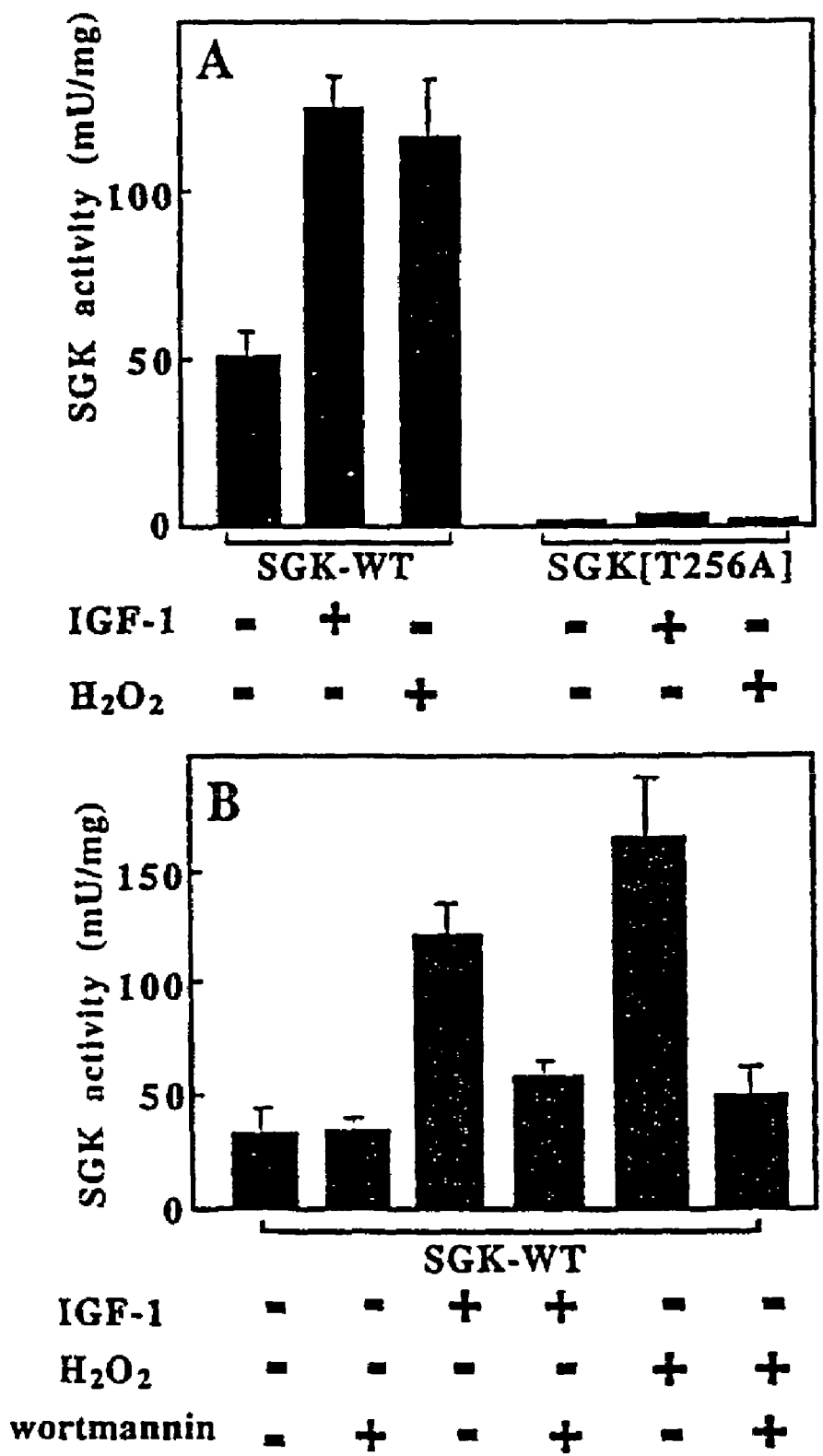

FIG. 8. Activation of SGK in 293 cells.

(A) Cells were transiently transfected with DNA constructs expressing wild type GST-SGK (SGK-WT) or GST-SGK[T256A], then stimulated for 10 min with 50 ng/ml IGF-1 or 25 min with 2 mM hydrogen peroxide, followed by lysis in ice-cold lysis buffer. 5 µl of glutathione Sepharose were added to 50 mg of cell lysate protein and after end over end rotation for 30 min at 40° C., the suspension was centrifuged for 1 min at 13,000×g. The supernatant was discarded and the beads washed four times with 1 ml of Buffer A containing 0.5 M NaCl, then three times with Buffer B. 40 41 of 60 mM Tris/HCl pH 7.5, 0.12 mM EGTA, 0.12% (v/v) 2-mercaptoethanol, 3.0 µM PKI, 1.2 µM microcystin-LR, 12 mM magnesium chloride and 36 µM "Crosstide" was added to the beads. After leaving on ice for 10 min, the beads were assayed for SGK activity at 30° C. by the addition of 5 µl of 1 mM [γ-$^{32}$P] ATP (500 cpm/pmol). The expression of wild-type and mutants SGKs in 293 cells were similar as judged by SDS/polyacrylamide gel electrophoresis followed by staining with Coomassie blue (data not shown). The results are presented ±S.D. for three separate experiments. (B) The experiment was carried with wild-type GST-SGK (SGK-WT) as in (A), except that the cells were pretreated for 10 min with 100 nM wortmannin before stimulation with IGF-1 or hydrogen peroxide.

Figure 9:
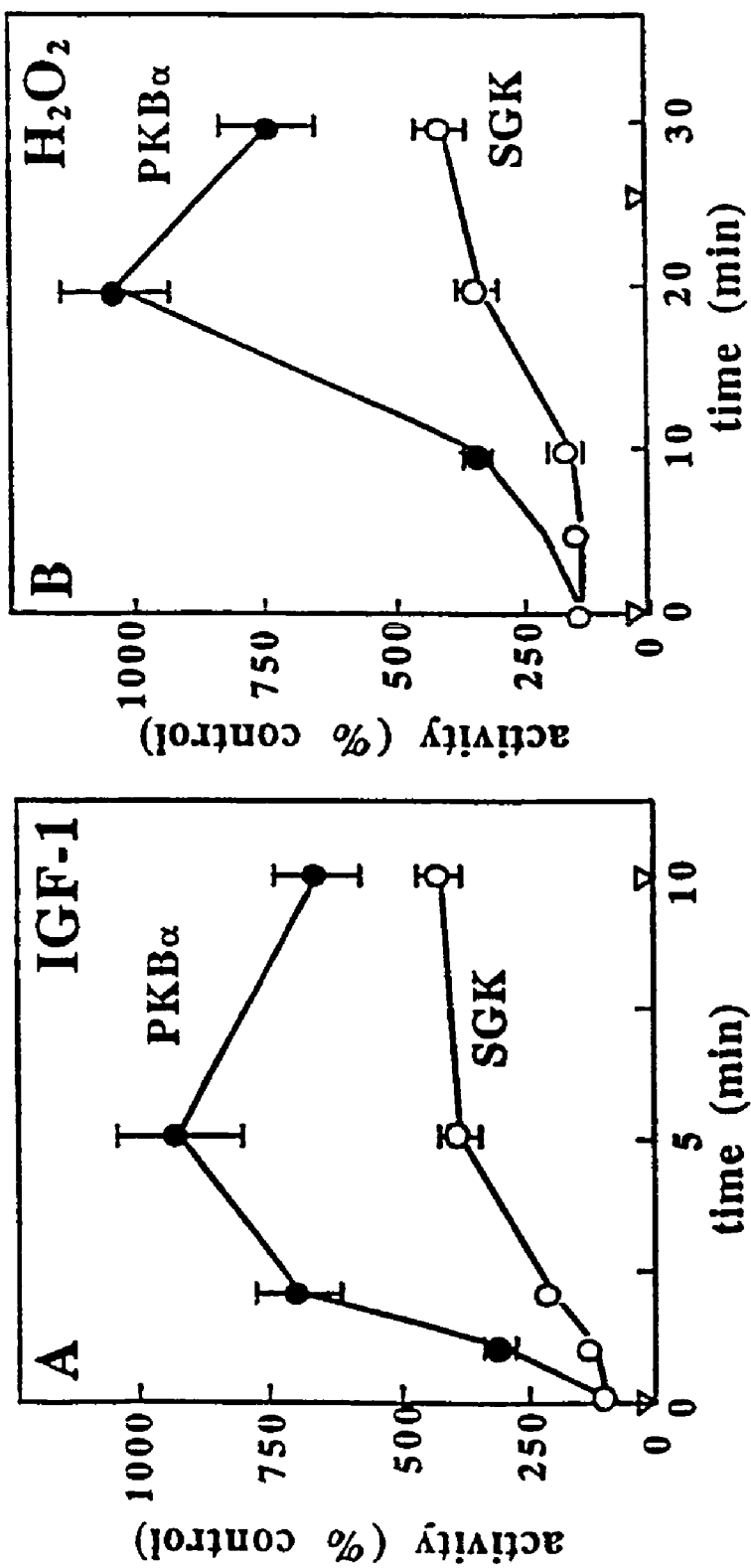

FIG. 9. Time course of activation of SGK in 293 cells. 293 cells were transiently transfected with pEBG-SGK (open circles) or pEBG-PKBα (closed circles) then stimulated with 50 ng/ml IGF-1 (A) or 2 mM hydrogen peroxide (B). At the times indicated, the cells were lysed and the GST-SGK or GST-PKBα purified on glutathione Sepharose as in FIG. 8 and assayed. The open triangle shows the GST-SGK activity after incubation with PP2A (30 mU/ml) as described in the legend to FIG. 3. The results are presented ±S.D. for a single experiment in which three separate dishes of cells were used at each time point. Similar results were obtained in another independent experiment.

Figure 10:
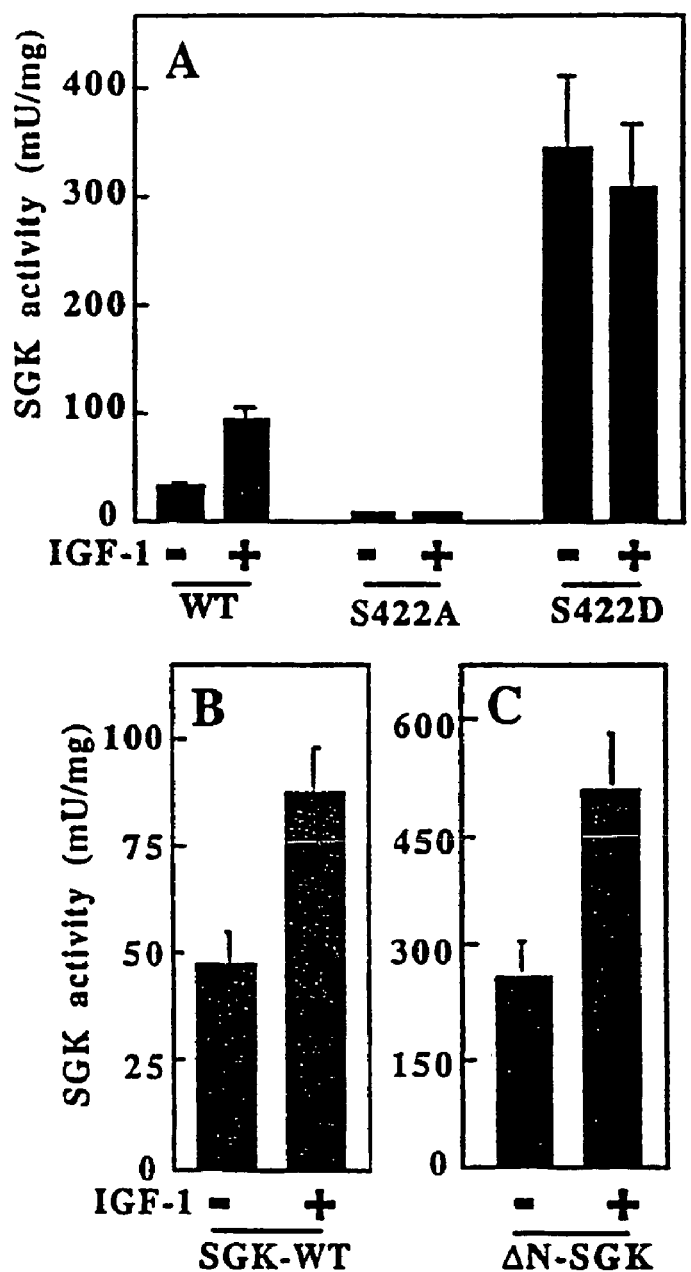

FIG. 10. Effect of mutations at Ser422 on the activation of SGK in 293 cells (A) 293 cells were transiently transfected with pEBG-SGK, pEBG-SGK[S422A] or pEBG-SGK [S422D] and then stimulated for 10 min with (+) or without (−) 50 ng/ml IGF-1. The cells were lysed and the GST-SGKs purified on glutathione-Sepharose as in FIG. 8 and assayed. 50 µg of cell lysate protein was used for the assay of wild type, SGK and SGK[S422A] and 25 µg for SGK[S422D]. Each protein was expressed in similar amounts as judged from SDS polyacrylamide gel electrophoresis followed by staining with Coomassie blue (data not shown). (B, C) Same as A except that the 293 cells were transiently transfected with pEBG-SGK (B) or pEBG-AN-SGK (C) as indicated and stimulated for 10 min with 50 ng/ml IGF-1. 50 µg of cell lysate protein was used for the assays of wild type SGK and 10 µg for the assays of the N-terminally truncated enzyme.

Figure 11:
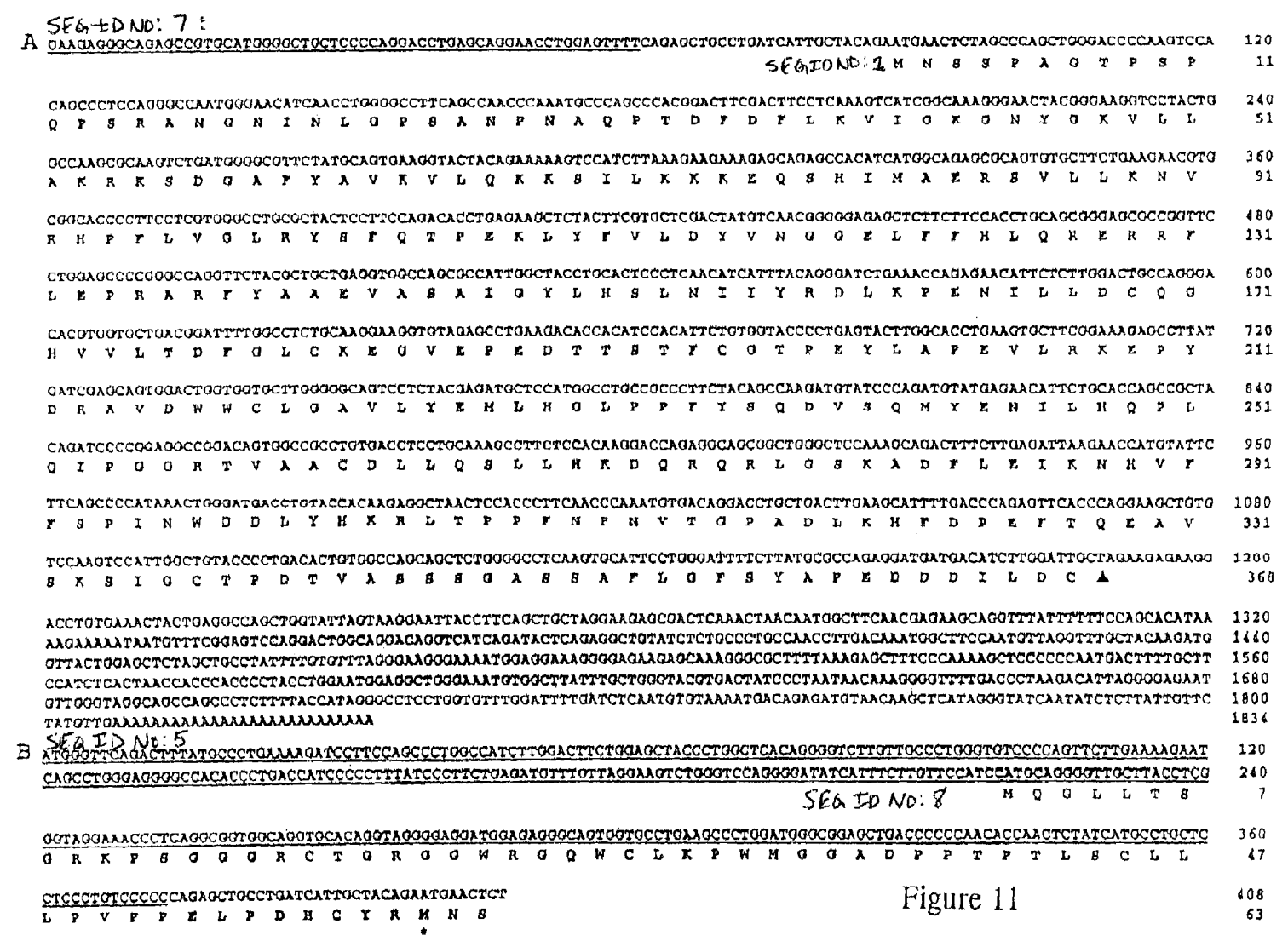

FIG. 11. Nucleotide and deduced amino acid sequences of human and mouse SGK2. A, SGK2α (SEQ ID NO:7) (Corresponding amino acid sequence shown as SEQ ID NO:1). Residues 33–239 correspond to the kinase catalytic domain. The termination codon is marked by a solid triangle. B, SGK2β; (SEQ ID NO:5) (Corresponding amino acid sequence shown as SEQ ID NO:8); The 5' region of SGK2β where it differs from SGK2α. The initiating methionine which starts the sequence of SGK2α is marked by an asterisk. After this residue, the sequences of SGK2α and SGK2β are identical.

Figure 12:
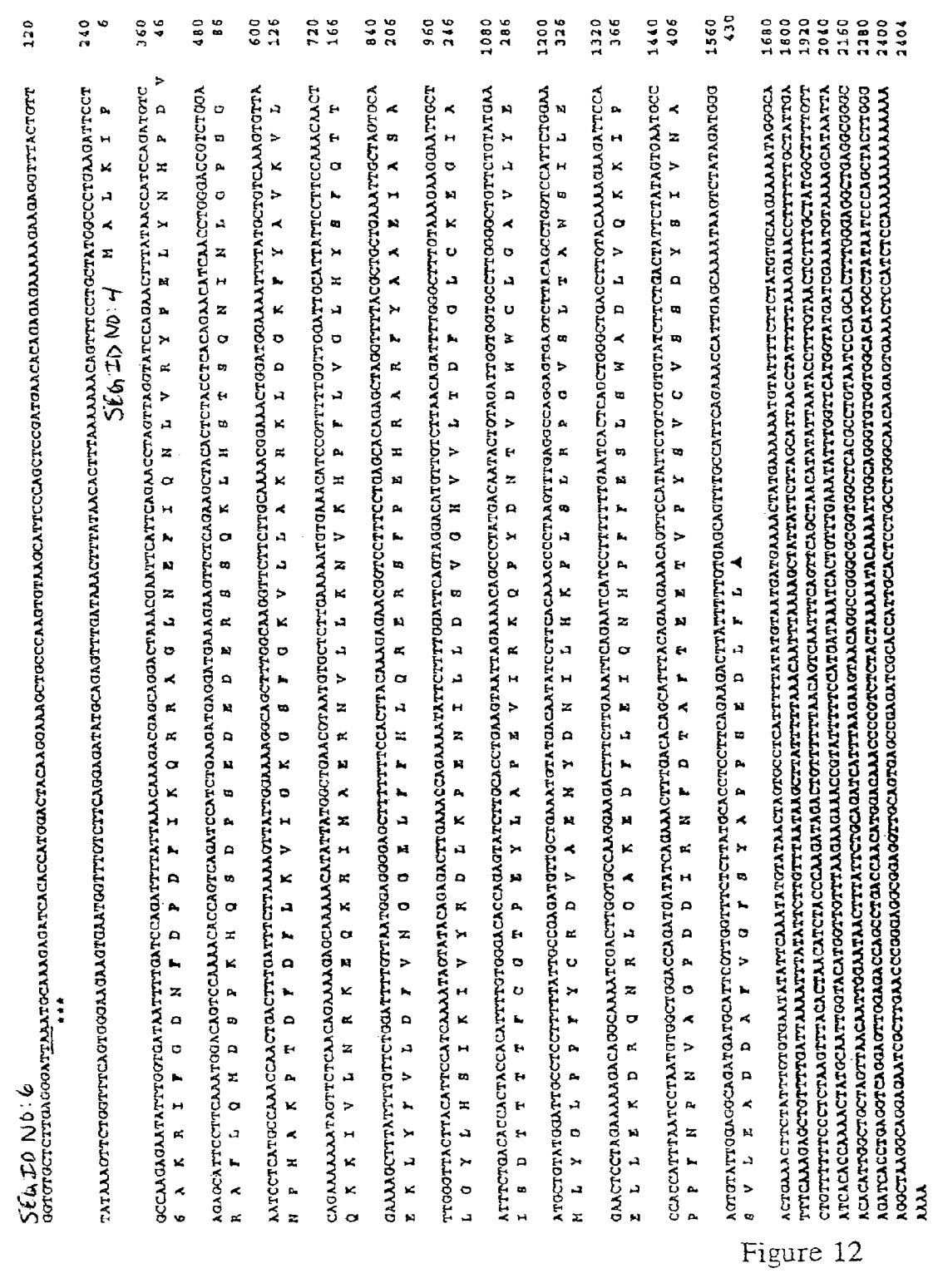

FIG. 12 Nucleotide (SEQ ID NO: 6) and deduced amino acid sequences (SEQ ID NO:4) of human SGK3. Residues 93–389 correspond to the kinase catalytic domain. The termination codon is marked by a sold triangle, the three asterisks denote the position of the most 5' ATG codon and the termination codon that immediately precedes it is underlined.

FIG. 13 Alignment of Amino Acid Sequences of SGK isoforms. The alignment of human (h) SGK1, hSGK2 (SEQ ID NO:8), murine (m) SGK2 (SEQ ID NO:3) and hHGK3 (SEQ ID NO:4) was carried out using the Clustal W program (Thompson, J. D., Higgins, D. G. and Gibson T. J. (1994) *Nuc. Acids. Res.* 22, 4673–4680). Identities are shaded in black and the initiation codons of SGKα (SEQ ID NO:1) and SGKβ (SEQ ID NO:8) are indicated by arrows. The two key phosphorylation sites are marked with asterisks.

Figure 14:
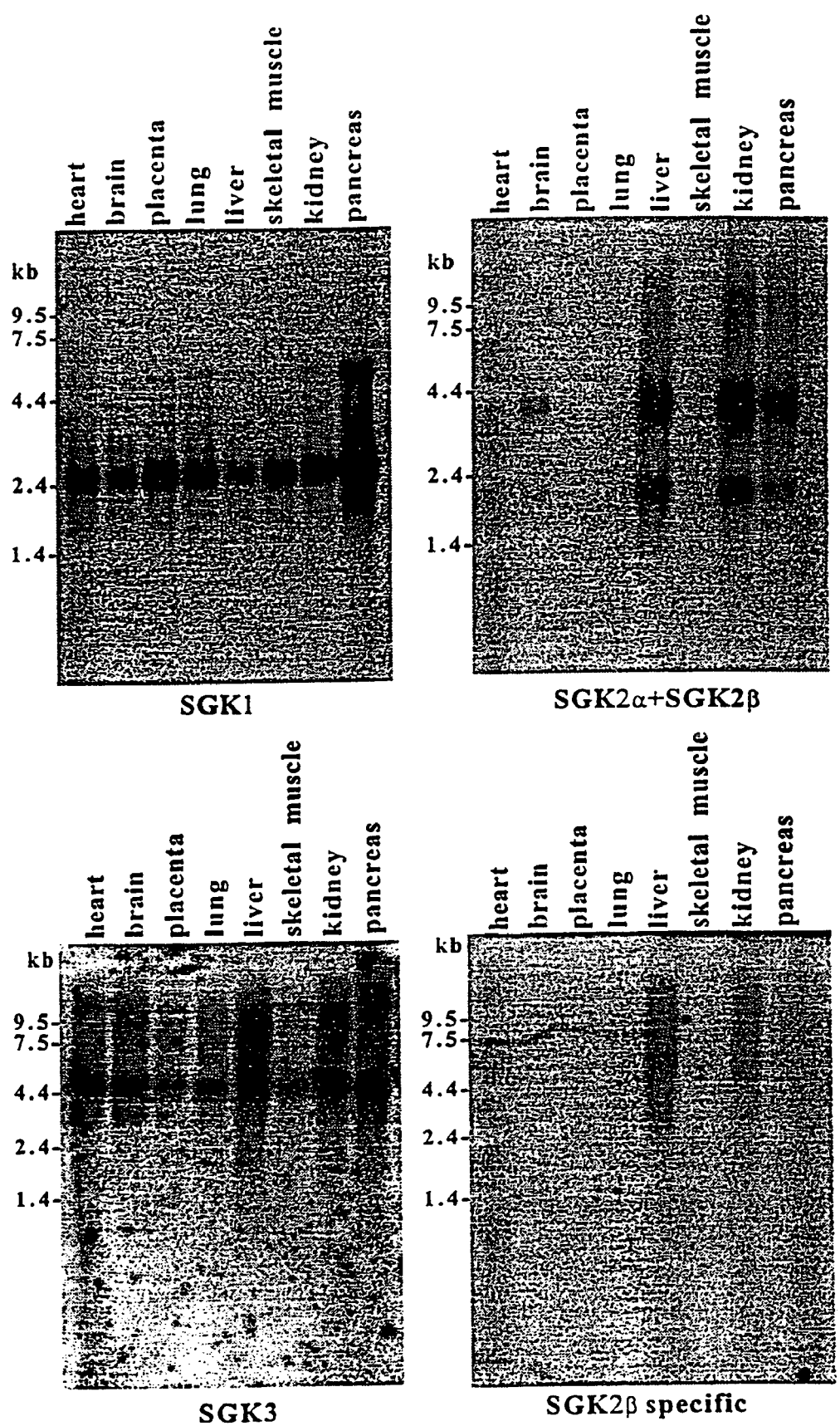

FIG. 14. Expression of the mRNA encoding SGK1, SGK2 and SGK3 in different human tissues. The Northern blots containing 2 µg of poly(A)+ RNA were hybridized with $^{32}$P-labelled SGK1, SGK2 and SGK3 cDNA probes. The membranes were then exposed to X-ray film for 3–5 days. The probe for SGK2 is common to SGK2α and SGK2β. The result obtained with a specific SGK2β probe is shown in a separate panel. The positions of standard RNA markers of defined sizes in kilobases (kb) are marked.

FIG. 15. Induction of the mRNA encoding SGK isoforms by different agonists.

(A) Rat2 fibroblasts that had been deprived of serum for 24 h were incubated for 2 h with 10% foetal bovine serum (serum) or 1 µM dexamethasone (Dex) or with no further additions (control). Total RNA extracted from each dish of cells (5 µg) was subjected to electrophoresis and analysed for SGK isoform transcripts by Northern blotting. To demonstrate equivalent loading of the samples, the membranes were reprobed with $^{32}$P-labelled glyceraldehyde-3-phosphate dehydrogenase (GAPDH) DNA bottom panel). The positions of the standard RNA markers 18S and 28S ribosomal RNA are indicated. (B) Same experiment as A using H4IIE hepatoma cells.

Figure 16:
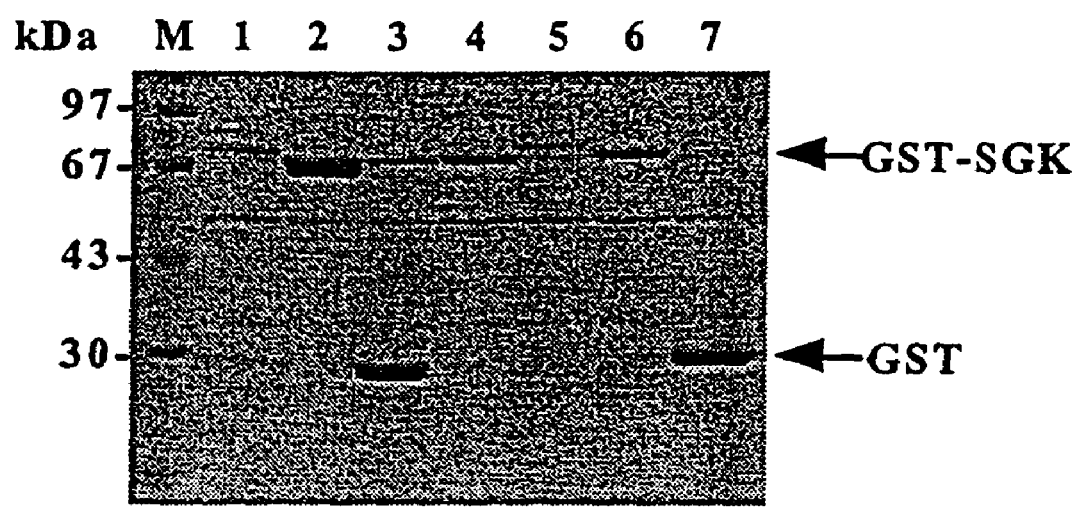

FIG. 16. Expression of SGK isoforms as GST-fusion proteins in 293 cells. GST-fusion proteins were expressed in 293 cells and purified from 200 µg of cell lysate protein by chromatography on glutathione-Sepharose. Proteins eluted with 15 mM glutathione were subjected to electrophoresis on a 10% SDS/polyacrylamide gel and stained with Coomassie Blue. Cells were transfected with following constructs: lane 1, pEBG-SGK1 expressing full-length SGK1; lane 2, pEBG-AN-SGK1 expressing an N-terminally truncated form of SGK1; lane 3, pEBG-SGK2β expressing full length SGK2β; lane 4, pEBG-SGK2α expressing full length of SGK2α; lane 5, pEBG-SGK3 expressing full-length SGK3; lane 6, pEBG-ΔN-SGK3 expressing an N-terminally truncated form of SGK3; lane 7, pEBG-2T expressing GST. The marker proteins (lane M) and their molecular masses are also shown.

FIG. 17. Phosphorylation and activation of wild type and mutant SGK isoforms by PDK1. A, B and C; Purified GST-fusion proteins (0.4 µg) were incubated with PP2A as described under Materials and methods, and microcystin-LR (1 µM) was then added to inactivate PP2A. The SGK isoforms (20 µg/ml) were then phosphorylated using the indicated amounts of purified GST-PDK1. After 30 min at 30° C., SGK activity was measured using Crosstide as substrate. The results are shown ±S.D. for three experiments. The closed circles show the results with wild type SGKs and the open circles results with mutant SGKs in which the residue equivalent to Ser473 of PKB had been changed to Asp. D, E and F; Same as A, B and C, except that 100 µM [γ-$^{32}$P] ATP (500 c.p.m/pmol) was used instead of unlabeled ATP. The reactions were stopped after 30 min by adding SDS and 2-mercaptoethanol to final concentrations of 1% (w/v) and 1% (v/v), respectively, followed by heating for 5 min at 95° C., electrophoresis on 10% SDS/polyacrylamide gels and autoradiography. The upper panels show results with wild type (wt) SGK isoforms and the lower panels results with mutant SGKs. The positions of each SGK isoform and PDK1 on the gels are marked.

Figure 18:
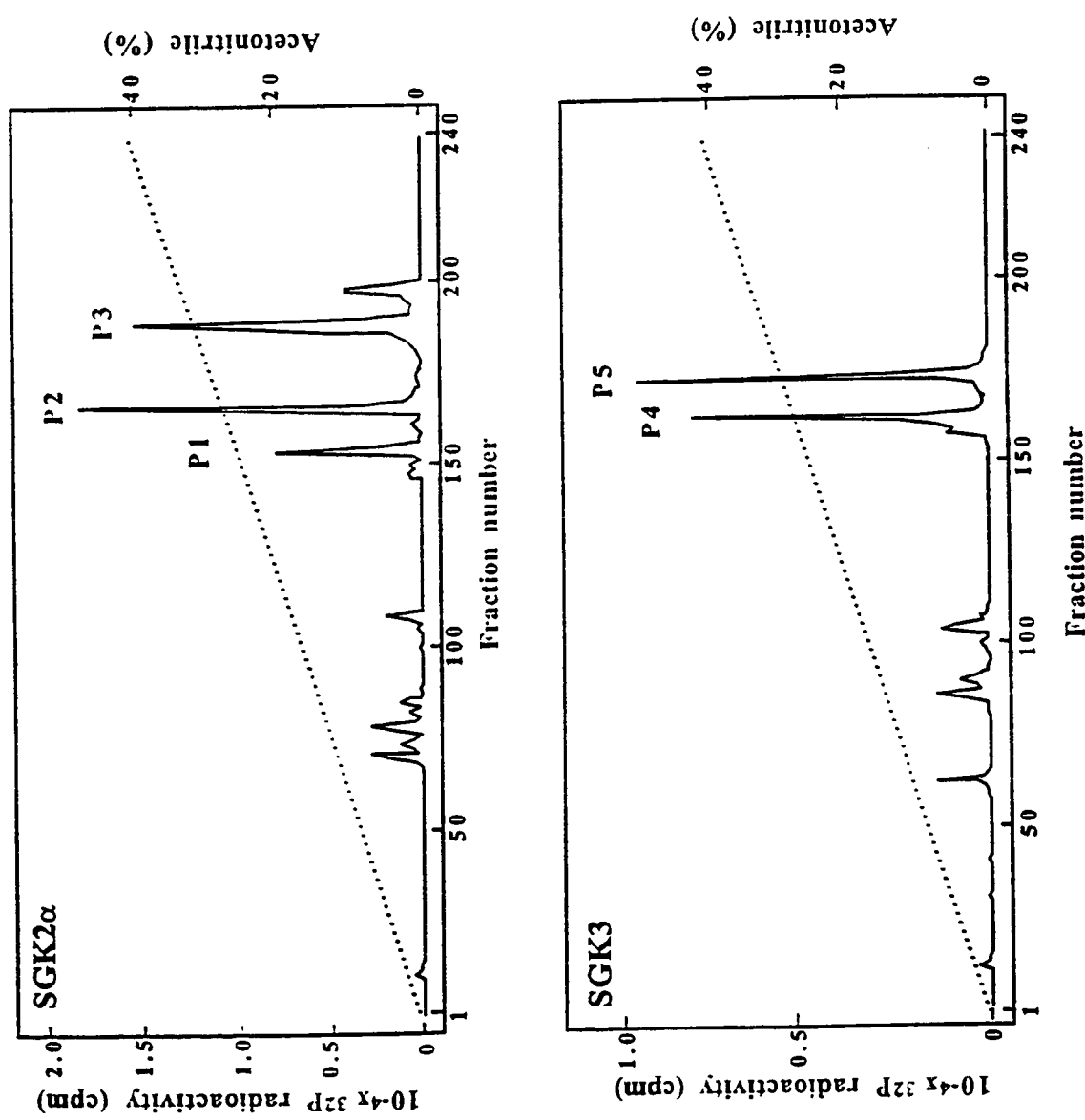

FIG. 18. Separation of tryptic phosphopeptides from SGK2α and SGK3 after phosphorylation by PDK1. GST-SGK2α (upper panel) or GST-SGK3 (lower panel) were inactivated by treatment with PP2A, phosphorylated with PDK1 (1.5 µg/ml) and Mg[γ$^{32}$P]ATP (5000 cpm/pmol), denatured in SDS, alkylated with 4-vinylpyridine and subjected to SDS/polyacrylamide gel electrophoresis as described in the legend to FIG. 17. The bands corresponding to SGK2α and SGK3 were excised, eluted from the gel, precipitated with trichlroacetic acid and digested with trypsin as described previously (Cuenda et al (1996) *EMBO J* 15, 4156–4164). The digest was applied to a Vydac C18 column equilibrated in 0.1% trifluoroacetic acid and the $^{32}$P-peptides (P) resolved using a linear acetontirile gradient in 0.1% trifluroacetic acid at a flow rate of 0.8 ml/min. Fractions of 0.4 ml were collected and analysed for $^{32}$P-radioactivity (full line). The acetonitrile gradient is shown by the diagonal broken line.

Figure 19:
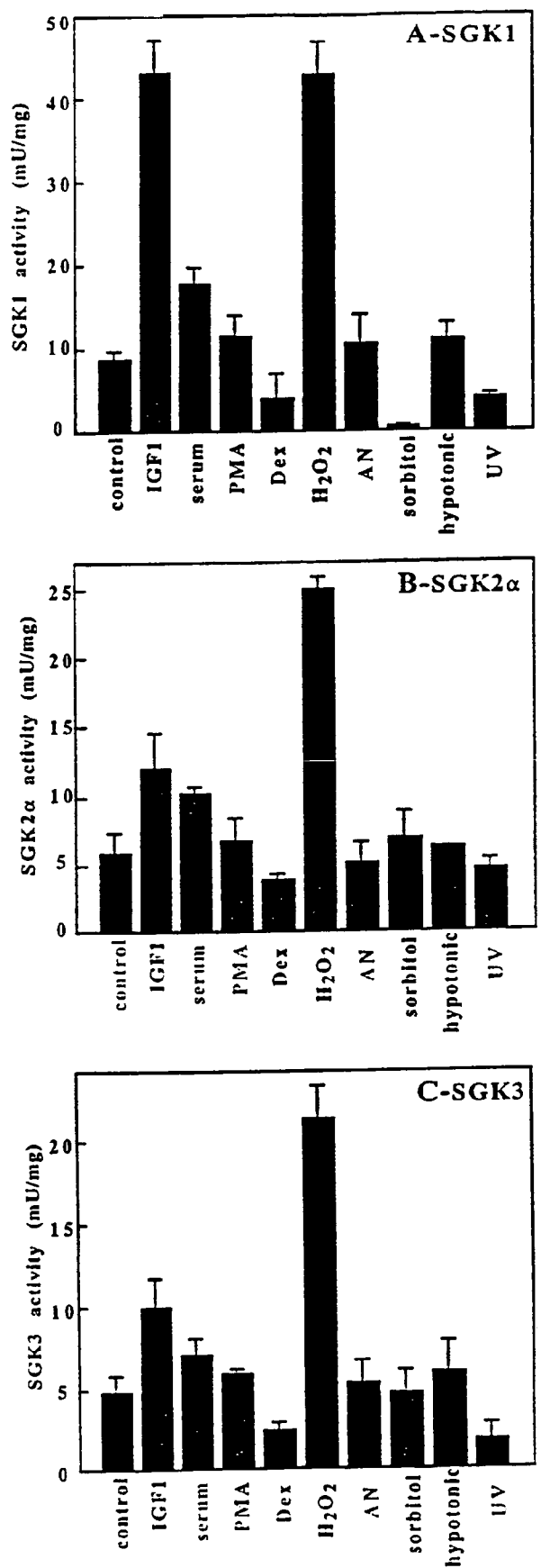

FIG. 19. Activation of SGK isoforms in 293 cells.

Cells were transiently transfected with DNA constructs expressing (A) GST-SGK1, (B), GST-SGK2α and (C) GST-SGK3. At 24 h after transfection, the cells were deprived of serum for 16 h, then exposed to 50 ng/ml IGF-1 (10 min), 400 ng/ml phorbol myristate acetate (PMA) (30 min), 10% serum (30 min), 1 µM dexamethasone (Dex, 60 min), 2 mM $H_2O_2$ (25 min), 5 µg/ml anisomycin (AN, 30 min), 0.4 M sorbitol (30 min), hypotonic stress (1 ml of water added to 3 ml of DMEM, 30 min), UV radiation (30 min after exposure to 200 J/m2) or left untreated (control). After each treatment, the cells were lysed in ice-cold lysis buffer and SGK activity in 100 µg of cell lysate protein was measured. The expression of each isoform was similar in each transfection as judged by SDS/PAGE followed by staining with Coomassie Blue (results not shown). The results are shown ±S.D. for three separate experiments.

Figure 20:
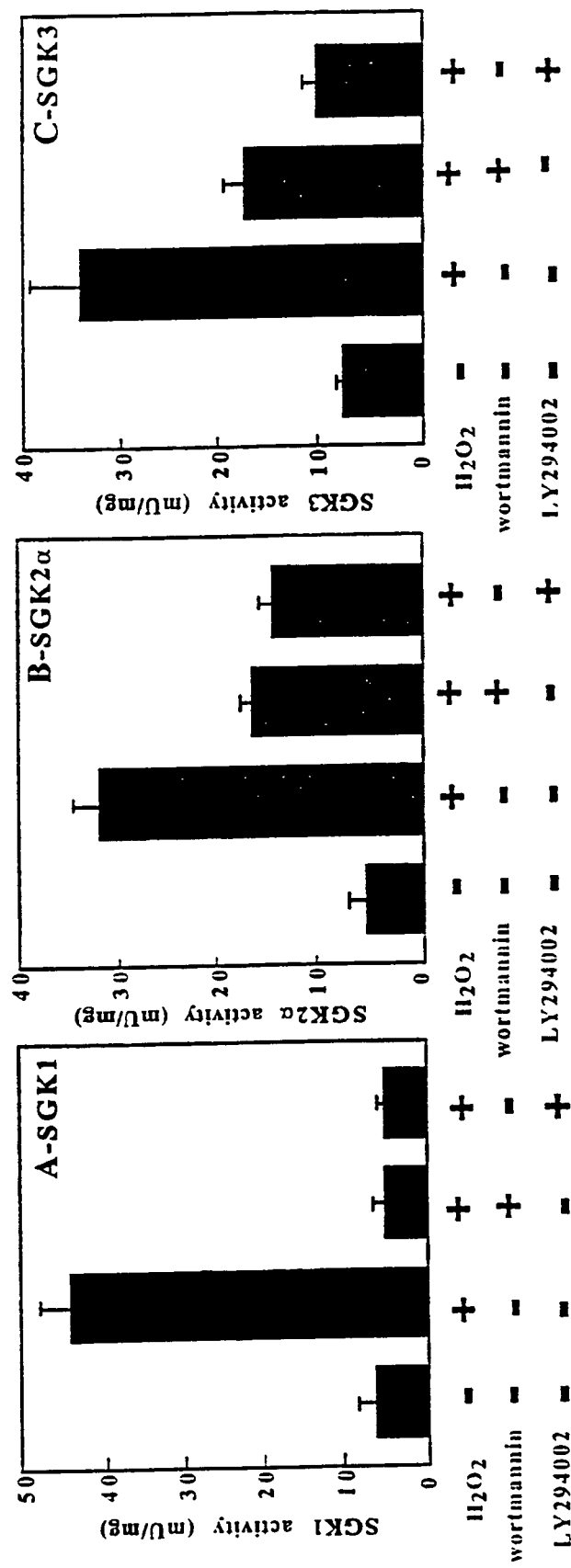

FIG. 20. Effect of PI 3-kinase inhibitors on the activation of SGK isoforms by hydrogen peroxide in 293 cells. Cells were transiently transfected with DNA constructs expressing (A) GST-SGK1, (B) GST-SGK2α and (C) GST-SGK3. At 24 h after transfection, the cells were deprived of serum for 16 h. The transfectants were then pretreated for 10 min with 100 nM wortmannin or for 1 h with 100 μM LY294002 and then stimulated for 25 min with 2 mM $H_2O_2$. The results are shown ±S.D. for three separate experiments.

EXAMPLE 1

Activation of SGK by Agonists that Activate phosphatidylinositide 3-kinase is Mediated by PDK1 and PDK2.

Summary. The PtdIns(3,4,5)$P_3$-dependent activation of protein kinase B (PKB) by 3-phosphoinositide-dependent protein kinases-1 and 2 (PDK1, PDK2) is a key event in mediating the effects of signals that activate PtdIns 3-kinase. Serum and glucocorticoid-induced protein kinase (SGK) is most similar to PKB (54% identity in the catalytic domain) and, although it lacks the PtdIns(3,4,5)$P_3$-binding pleckstrin-homology (PH) domain, it retains the residues in PKI that are phosphorylated by PDK1 (Thr308) and PDK2 (Ser473). Here we show that, like PKB, SGK is activated via a PtdIns 3-kinase-dependent pathway when 293 cells are stimulated with insulin-like growth factor-1 (IGF-1) or exposed to hydrogen peroxide. Consistent with this finding, PDK1 activates SGK in vitro by phosphorylating Thr256, the residue equivalent to Thr308 of PKB, but the rate of activation is unaffected by PtdIns(3,4,5)$P_3$. However, the PDK1-induced activation of SGK in vitro is greatly potentiated by the mutation of Ser422 to Asp (the residue equivalent to Ser473 of PKB). Consistent with this finding, SGK [Ser422Asp] expressed in 293 cells is fully activated by phosphorylation even in unstimulated cells, and this activation is unaffected by inhibitors of PtdIns 3-kinase. In contrast to PKB, the mutation of Ser422 does not by itself induce any activation of SGK and mutation of Thr256 to Asp abolishes activation. Our results are consistent with a model in which the activation of SGK by IGF1 or hydrogen peroxide is initiated by the PtdIns(3,4,5)$P_3$-dependent activation of PDK2 which phosphorylates Ser422. This is then followed by the PtdIns(3,4,5)$P_3$-independent phosphorylation at Thr256, catalysed by PDK1, which activates SGK. Like PKB, SGK preferentially phosphorylates serine and threonine residues that lie in Arg-Xaa-Arg-Xaa-Xaa-(Ser/Thr)- (SEQ. ID. NO:46) motifs, and SGK and PKB inactivated glycogen synthase kinase-3 (GSK-3) at similar rates in vitro. These findings raise the possibility that some physiological roles ascribed to PKB based on the overexpression of constitutively active PKB mutants, may be mediated by SGK.

Materials and Methods

Materials. Human PDK1 was expressed as a glutathione-S-transferase (GST) fusion protein in 293 cells and purified on glutathione-Sepharose [9]. V8 protease (protease Glu-C) and complete protease inhibitor cock-tail were purchased from Boehringer Mannheim. Residues 5–24 of the specific protein inhibitor of cAMP-dependent protein kinase (PKI) and all other peptides were synthesised at the Department of MRC Protein Phosphorylation Unit, University of Dundee, by Mr. F. B. Caudwell. Sources of other materials are given in [6].

Buffer solutions. Buffer A was 50 mM Tris/HCl pH 7.5, 1 mM EDTA, 1 mM EGTA, 1% (w/v) Triton X-100, 1 mM sodium orthovanadate, 50 mM NaF, 5 mM sodium pyrophosphate, 0.27 M sucrose, 0.1% (v/v) 2-mercaptoethanol. Lysis buffer was Buffer A containing 1 μM microcystin-LR, plus complete protease inhibitor cocktail (one tablet/50 ml). Buffer B was 50 mM Tris/HCl pH 7.5, 1 mM EGTA, 0.1% (v/v) 2-mercaptoethanol.

Plasmids expressing SGK and site-directed mutagenesis. A full length cDNA encoding human SGK from an infant brain library was obtained from I.M.A.G.E. Consortium (clone ID 42669) and modified by PCR amplification to introduce a BamHI site at the 5' end (in frame with the GST sequence of the pEBG2T vector) and a KpnI site at the 3' end using, oligonucleotides 5'-ACA CGG ATC CGC CAC CAT GTA TCC ATA TGA TGT TCC AGA TTA TGC TAC GGT GAA AAC TGA GGC TGC TAA GGG C-3' (SEQ. ID. NO:9) and 5'-ACA CGG TAC CGT CGA CTC AGA GGA AAG AGT CCG TGG GAG G-3' (SEQ. ID. NO:10). The PCR product was digested with BamHI and KpnI and inserted into the cloning site of pEBG-2T. A truncated form of SGK (ΔN-SGK) lacking the N-terminal 60 residues was obtained by removing the fragment between the BamHI site at the 5' of the cDNA and a BglII site located 175 bp from the initiation codon, followed by religation after filling the gap with Klenow fragment. All of the point mutations in the SGK gene were introduced by in vitro mutagenesis using PCR.

Expression of SGK in 293 Cells.

Cells were transfected with 10 μg (10 cm dish) or 3 μg (6 cm dish) of the pEBG-SGK constructs using a modified calcium phosphate gel method [6]. At 24 h after transfection, the cells were deprived of serum for 16 h, then incubated for 10 min with or without 100 nM wortmannin or for 1 h with or without other inhibitors, followed by stimulation with 50 ng/ml IGF-1 or 2 mM hydrogen peroxide. The cells were lysed in 1 ml of ice-cold lysis buffer, centrifuged for 5 min at 13,000 g and GST-SGK was purified on glutathione-Sepharose as described for PKB [6]. The glutathione-Sepharose eluate was stored in aliquots at −80° C.

Phosphorylation and assay of SGK. Phosphorylation was carried out at 30° C. in 50 μl incubations containing 50 mM Tris/HCl pH 7.5, 0.1 mM EGTA, 0.1% (v/v) 2-mercaptoethanol, 2.5 μM PKI, 1 μM microcystin-LR, 10 mM magnesium chloride and 100 μM ATP. Where indicated lipid vesicles containing phosphatidylcholine (100 μM), phosphatidyl serine (100 μM) and PtdIns(3,4,5)$P_3$ (1 μM) were also included. SGK activity was assayed exactly as described for PKB [6] using the peptide GRPRTSSFAEG (SEQ. ID. NO:30) ("Crosstide") at 30 μM as substrate. One unit of activity (U) was that amount which catalysed the phosphorylation of 1 mole of Crosstide in one min.

Mapping the site on SGK phosphorylated by PDK1. The N-terminally truncated SGK in which Ser422 had been mutated to Asp (GST-ΔN-SGK[S422D]) (26 μg) was incubated for 20 min at 30° C. with PP2A (30 mU/ml), where one unit of activity is that amount which catalyses the dephosphorylation of 1 nmole of phosphorylase a in one min. After addition of microcystin-LR to 1 μM to inactivate PP2A, the SGK was phosphorylated by incubation for 30 min at 30° C. with GST-PDK1 (2 μg) and [$\gamma^{32}$P]ATP (5,000 cpm/pmol). The reaction was stopped after 30 min by adding SDS and 2-mercaptoethanol to final concentrations of 1% (w/v) and 1% (v/v), respectively, followed by heating at 95° C. for 5 min. The sample was then incubated for 1 h at 30° C. with 2% (v/v) 4-vinylpyridine to alkylate cysteine residues, electrophoresed on a 10% SDS/polyacrylamide gel, and the $^{32}$P-labelled SGK was eluted from the gel and precipitated by the addition of trichloroacetic acid to 20% (w/v). The precipitated protein was washed six times with 0.2 ml of water, resuspended in 0.3 ml of 50 mM $NH_4HCO_3$ (pH 7.8), digested for 18 h with V8 protease (1 μg) and then chromatographed on a Vydac C18 column as described under Results. Peptide fractions were analysed on a Perceptive Biosystems (Framingham, Mass.) Elite STR MALDI- TOF mass spectrometer in the linear and relectron mode, using 10 mg/ml α-cyanocinnamic acid as the matrix. Phosphoamino acid analysis was carried out as described in [26].

Results

Expression of SGK in 293 Cells.

Initial attempts to express SGK with a haemaglutinnin tag at its N-terminus were unsuccessful because the expressed protein was insoluble. The work reported in this example was therefore carried out using GST-fusion proteins, which were soluble when expressed in 293 cells. Full length GST-SGK (FIG. 2A, lane 2) was expressed in 293 cells at a much lower level than GST-PKBα (FIG. 2A, lane 3). This low level of expression appears to be due to the N-terminal 60 residues of SGK, because their removal increased the level of expression 50–250 fold (FIG. 2B, lanes 4 and 5). 10–50 μg of 20% pure full length SGK and 0.5 mg of 80% pure ΔN-SKG(61–431) was usually obtained from 10, 10 cm diameter dishes of cells.

Phosphorylation and Activation of Wild Type SGK by PDK1 in Vitro.

The activity of GST-SGK purified from 293 cells was decreased by 70% following incubation with protein phosphatase 2A (PP2A) (FIG. 3), a serine/threonine-specific phosphatase, and inactivation was prevented by microcystin, a specific PP2A inhibitor [27]. Thus, the basal activity of SGK results from its phosphorylation at one or more serine/threonine residues.

GST-SGK could be phosphorylated by PDK1 (FIG. 4A) and phosphor-ylation was accompanied by a 10-fold increase in the basal activity (FIG. 4B). Almost the same level of activity was attained if GST-SGK was first inactivated by treatment with PP2A and then phosphorylated with PDK1 (data not shown). However, PDK1 phosphorylated GST-SGK much more slowly than PKBα and the maximal stoichiometry of phosphorylation that could be attained was 0.05 mol/mol, compared to 0.5 mol/mol for PKBα. Moreover, unlike the activation of PKBα, the phosphorylation (FIG. 4A) and activation (FIG. 4B) of SGK was unaffected by PtdIns(3,4,5)$P_3$ in the presence (FIG. 4) or absence (data not shown) of lipid vesicles containing phosphatidylserine and phosphatidylcholine.

Effect of Mutation of Ser422 and Thr256 on the Activity of SGK.

PKBα can be partially activated (5-fold) by mutation of Thr308 to Asp or by mutation of Ser473 to Asp, and almost fully activated (20-fold) when both mutations are combined. It was therefore of interest to study the effect of the equivalent mutations on the activity of SGK.

GST-SGK[T256D], GST-SGK[T256E] or GST-SGK [T256A] purified from transfected 293 cells were all much less active than wild-type SGK, the activities being similar to wild-type SGK that had been treated with PP2A (FIG. 3). In contrast, GST-SGK(S422D) purified from 293 cells had a specific activity more than ten-fold higher than that of the wild-type enzyme (FIG. 3). However, the activity of GST-SGK(S422D) did not result from the mutation of Ser422 to Asp per se but from increased phosphorylation, because it could be reduced to the same level as GST-SGK[T256D] or GST-SGK[T256A] by incubation with PP2A (FIG. 2).

GST-SGK[S422A] purified from 293 cells also had very low activity, similar to GST-SGK[T256A] or the wild-type enzyme after treatment with PP2A.

Effect of Mutation of Ser422 or Thr256 on the Phosphorylation of SGK by PDK1 in Vitro.

The mutation of Ser422 to Ala did not affect the extent of phosphorylation of SGK by PDK1 (FIG. 5A), but reduced the extent of activation by 60% (FIG. 5B). In contrast, the mutation of Thr256 to Ala (or mutation of both Thr256 and Ser422 to Ala) reduced phosphorylation by 80–90% (FIG. 5A) and abolished activation by PDK1 (FIG. 5B).

The mutation of Ser422 to Asp stimulated the rate of phosphorylation (FIG. 5C) and activation (FIG. 5D) by PDK1 at least six-fold. In contrast, the GST-SGK[T256A/S422D] double mutant was not activated at all by PDK1 and phosphorylation by PDK1 was reduced by 80–90% (data not shown).

We also mutated Lys 127 in the ATP binding site to Ala to create a "kinase dead" protein. This mutant was phosphorylated at the same rate, and to the same extent, as wild type SGK (FIG. 5A) and, as expected, could not be activated by PDK1 (FIG. 5B).

Identification of Thr256 as the Residue on SGK Phosphorylated by PDK1 in Vitro.

The results described above suggested that the activation of SGK by PDK1 was likely to result from the phosphorylation of Thr256. In order to investigate whether this was so, we used a form of SGK that was truncated at its N-terminus (GST-ΔN-SGK[61–431]) because this mutant was expressed at far higher levels than the wild type enzyme, and Ser422 was also mutated to Asp to to facilitate phosphorylation by PDK1. Like GST-SGK[S422D] (FIG. 3), GST-ΔN-SGK(61–431)[S422D] purified from 293 cells had a high activity, which could be virtually abolished by treatment with PP2A (data not shown).

PP2A-treated GST-ΔN-SGK[S422D] was phosphorylated by PDK1 to a stoichiometry of 0.6 mol/mol protein, and the $^{32}$P-labelled enzyme digested with V8 protease and chromatographed on a C18 column. One major peak and several minor peaks of $^{32}$P radioactivity were observed as shown in FIG. 6A. Analysis of the major peak by MALDI-TOF mass spectroscopy showed that its molecular mass (1923.15) was identical to that expected for the peptide comprising residues 247–262 of SGK (NEEHNSTTSTFCGTPE) (SEQ. ID. NO:2) containing one phosphorylated residue. Residue 247 is preceded by glutamic acid, as expected from the specificity of V8 protease. Phosphoamino acid analysis indicated that this peptide contained phosphothreonine only (inset to FIG. 6A). When this phosphopeptide was subjected to solid phase sequencing, $^{32}$P-radioactivity was released after the 10th cycle of Edman degradation corresponding to Thr256 (FIG. 6B). These results, together with those obtained using the Ser256Ala mutant (FIG. 5A) indicate that SGK is phosphorylated by PDK1 at Thr256, the equivalent residue to Thr308 of PKBα.

Substrate specificity of SGK. We compared the substrate specificities of SGK and PKBα towards several synthetic peptides related to "Crosstide" (Table 1). Like PKBα, SGK had an absolute requirement for an arginine residue five residues N-terminal to the site of phosphorylation since mutation, even to another basic amino acid (Lys), almost abolished activity. The presence of an Arg three residues N-terminal to the site of phosphorylation was also important, but not quite as critical as for PKBα. Like PKBα, SGK required at least one residue C-terminal to the phosphorylation site and a hydrophobic residue was strongly preferred at this position, though not as critical as for PKBα. Another significant difference between PKBα and SGK was that the latter was more tolerant of the substitution of serine by threonine at the site of phosphorylation. Although the results presented in Table 1 were carried out using PDK1-activated GST-ΔN-SGK[S422D], similar results were obtained with full length SGK.

Glycogen synthase kinase-3 (GSK-3) is a protein thought to be a physiological substrate for PKB [28]. When PKBα and SGK were matched for activity towards Crosstide, both enzymes inactivated GSK3 at similar rates (FIG. 7).

Activation of SGK in 293 Cells by Extracellular Signals.

PKB is activated in 293 cells in response to agonists that activate PtdIns 3-kinase, such as insulin or IGF-1 or certain adverse stimuli (heat shock, oxidative stress). Since the activation of PKB results from the phosphorylation of Thr308 and Ser473, and these residues and the sequences surrounding them are highly conserved in SGK (FIG. 1), we investigated whether SGK could be activated by these and/or other signals in 293 cells.

Cells overexpressing GST-SGK were stimulated with IGF-1 or exposed to hydrogen peroxide, which induced a 2.5–4-fold activation (FIGS. 8A and 8B). Activation was strongly suppressed if the cells were first pre-incubated with the PtdIns 3-kinase inhibitor wortmannin (FIG. 8B). In contrast, the immunosuppressant drug rapamycin that prevents the activation of p70 S6 kinase, had no effect on the activation of SGK (data not shown). SGK[T256A] could not be activated by either IGF-1 or hydrogen peroxide.

The IGF-1 and hydrogen peroxide-induced activation was caused by increased phosphorylation because, like the basal activity, the stimulated activity was abolished by treatment with PP2A (FIG. 9). In addition activation by these stimuli was not observed when SGK[T256A] was transfected instead of wild-type SGK (FIG. 8A). The activation of GSTSGK induced by IGF-1 or hydrogen peroxide was slightly slower than activation of GST-PKBα under the same conditions (FIG. 9).

Phorbol myristate acetate (400 ng/ml, 30 min) or EGF (100 ng/ml, 30 min), which are much stronger activators of the classical mitogen-activated protein (MAP) kinase cascade in 293 cells than IGF-1, did not induce any activation of SGK (data not shown).

Activation of SGK Mutants by IGF-1.

The activity of GST-SGK[S422D] was high in 293 cells that had not been stimulated with IGF-1 (FIG. 3) and, interestingly, could not be activated further by IGF-1 (FIG. 10A). Moreover, preincubation of 293 cells with 100 nM wortmannin (30 min) did not affect the high basal activity of SGK (data not shown). In contrast, GST-SGK[S422A] had very low activity in 293 cells that was not increased by IGF-1 (FIG. 10A).

GST-ΔN-SGK was activated similarly to full-length wild-type SGK in response to IGF-1 (FIGS. 10B and 10C), indicating that the N-terminal non-catalytic domain is not required for activation in 293 cells.

Discussion.

Although it is well established that SGK is the product of an immediate early gene whose levels increase within a hour in response to several agonists and pathological conditions (see Introduction), the possibility that SGK is also regulated by reversible phosphorylation has not been investigated previously. In this example, we establish that the activity of SGK expressed in 293 cells is determined by its level of phosphorylation (FIG. 3) which increases within minutes in response to signals that activate PtdIns 3-kinase (FIGS. 8 and 9). We have also provided evidence that the key phosphorylation sites on SGK are Thr256 and Ser422, the residues equivalent to those on PKBα that are targeted by PDK1 and PDK2, respectively.

SGK is phosphorylated and activated by PDK1 in vitro (FIG. 4) and the major site of phosphorylation is Thr256 (FIG. 6). Activation is abolished, and phosphorylation greatly reduced, if Thr256 is mutated to Ala (FIG. 5). Thus the PDK1-induced activation of SGK is mediated by the phosphorylation of Thr256. However, the effects of phosphorylation could not be mimicked by mutating Thr256 to an acidic residue, and such mutations actually reduced activity to the level of the PP2A-treated wild-type enzyme (FIG. 3). This is similar to observations made with p70 S6 kinase [28], but is in contrast to PKBα where mutation of Thr308 to Asp causes partial activation of the enzyme [6]. The finding that phosphorylation of SGK by PDK1 is not totally abolished if Thr256 is mutated to Ala (FIG. 4) indicates that PDK1 is capable of phosphorylating another site(s) on GST-SGK[T256A] in vitro, but the identity of this site and its relevance (if any) to the activation process remains to be evaluated. The Thr308Ala mutant of PKBα (but not the wild-type enzyme) is phosphorylated at Thr304 by PDK1 in vitro without causing any activation (results not shown).

Several lines of evidence suggest that one role for the phosphorylation of Ser422 is to accelerate phosphorylation at Thr256 by PDK1 and hence the activation of SGK. Thus, GST-SGK is phosphorylated by PDK1 in vitro much more slowly than PKBα, but phosphorylation and activation is greatly potentiated by the mutation of Ser422 to Asp (FIG. 5). The Ser422 to Asp mutation also greatly increases the activity of SGK expressed in 293 cells (FIGS. 3 and 9), and this results from increased phosphorylation (presumably at Thr256) because it is abolished by treatment with PP2A (FIG. 3) and because the Thr256Ala/Ser422Asp and Thr256Asp/Ser421-Asp double mutants are inactive.

If it is assumed that the Ser422Asp mutation mimics the effect of phosphorylation at this residue, and that the GST-fusion protein behaves similarly to wild-type SGK, then the following model for the activation of SGK would be consistent with the results obtained in this paper. (1) The PtdIns(3,4,5)P$_3$ generated in response to IGF-1 or hydrogen peroxide activates PDK2 (or a closely related enzyme), which then phosphorylates SGK at Ser422. (2) The phosphorylation of Ser422 greatly potentiates the rate at which SGK is phosphorylated and activated by PDK1 (or a closely related enzyme). This model explains why the IGF-1 induced or hydrogen-peroxide induced activation of SGK in 293 cells is suppressed by wortmannin (FIG. 8B), why the activation of SGK by PDK1 in vitro is independent of PtdIns(3,4,5)P3 (FIG. 4) and why the activity of GST-SGK [S422D] is not suppressed by wortmannin. This model is similar to the mechanism proposed for the activation of p70 S6 kinase [15, 16] but, in order to validate it, it will be necessary to find out whether PDK2 is indeed PtdIns(3,4,5)P3-dependent, and to study the effect of PDK2 on the activation of SGK in the presence and absence of PDK1.

The mechanism of activation of SGK differs from that of PKB in several respects. Firstly, the binding of PtdIns(3,4,5)P$_3$ to the PH domain of PKB is essential before any activation can take place [7]. Secondly, the interaction of PtdIns(3,4,5)P3 with the PH domain of PKB causes its recruitment to the plasma membrane, which may facilitate its activation by menbrane associated PDK1 and PDK2. Thirdly, PDK1 greatly facilitates the PtdIns(3,4,5)P$_3$-dependent activation of PKB in lipid vesicles in vitro, and may therefore also be critical for the activation of PKB at the plasma membrane in vivo. These differences may explain why essentially no activation of PKB occurs in vivo until PtdIns(3,4,5)P$_3$ is elevated and the larger and more rapid activation of PKB by IGF-1 or hydrogen peroxide in 293 cells (FIG. 9). However, like the activation of SGK, the activation of PKB may also be dependent on the interaction of PtdIns(3,4,5)P$_3$ with PDK2.

Like PKB and p70 S6 kinase, SGK phosphorylates peptides at serine or threonine residues that lie in sequences with arginine residues at positions n-3 and n-5 and a large hydrophobic residue at position n+1, where n is the site of phosphorylation. The physiological substrates of SGK are unknown. However, like PKB, SGK is activated by a PtdIns 3-kinase dependent pathway and (unlike p70 S6 kinase) activation is not prevented by the immunosuppressant drug rapamycin. Moreover, when matched for activity towards the standard peptide substrate Crosstide, SGK and PKBα catalysed the inactivation of GSK3 at similar rates (FIG. 7). Since GSK3 is thought to be a physiological substrate of PKB [30], it is therefore possible that some of the physiological roles ascribed to PKB based on the overexpression of constitutively active mutants (reviewed in [2]), may actually be mediated by SGK. Since PKB and SGK may well be activated by the same protein kinases in vivo (PDK1 and PDK2), it may not be possible to distinguish their physiological roles by the use of dominant negative mutants. The developments of drugs that inhibit PKB but not SGK, and vice versa, or the generation of mouse "knockouts" may be necessary to answer these questions.

TABLE 1

Comparison of the activity of SGK and PKBα towards synthetic peptides related to Crosstide.
The experiments were carried out with GST-ΔN-SGK and GST-PKBα purified from 293 cells and activated by PDK1. The activities are presented relative to peptide 1 (Crosstide). The concentration of each peptide was 30 μM. Amino acid substitutions are underlined. The serine residue in Crosstide that is phosphorylated by PKB is marked with an asterisk.

| | Peptide | SGK | PKBα |
|---|---|---|---|
| | | * | |
| 1 | GRPRTSSFAEG (SEQ. ID. NO: 30) | 100% | 100% |
| 2 | RPRTSSF (SEQ. ID. NO: 39) | 154 | 160 |
| 3 | RPRTS_A_F (SEQ. ID. NO: 32) | <1 | <1 |
| 4 | PRTSSF (SEQ. ID. NO: 33) | <1 | <1 |
| 5 | RPRTSS (SEQ. ID. NO: 31) | 10 | <1 |
| 6 | RPRTSTF (SEQ. ID. NO: 35) | 156 | 208 |
| 7 | RPR_AA_TF (SEQ. ID. NO: 36) | 73 | 55 |
| 8 | _K_PRTSSF (SEQ. ID. NO: 37) | 2 | 6 |
| 9 | RP_K_TSSF (SEQ. ID. NO: 38) | 49 | 26 |
| 10 | RPRTSSF (SEQ. ID. NO: 39) | 154 | 160 |
| 11 | RPRTSS_L_ (SEQ. ID. NO: 40) | 135 | 69 |
| 12 | RPRTSS_V_ (SEQ. ID. NO: 41) | 131 | 67 |
| 13 | RPRTSS_A_ (SEQ. ID. NO: 42) | 107 | 26 |
| 14 | RPRTSS_K_ (SEQ. ID. NO: 43) | 146 | 48 |
| 15 | RPRTSS_E_ (SEQ. ID. NO: 44) | 84 | 21 |

EXAMPLE 2

Alternative Assays

A Scintillation Proximity Assay (SPA) system (Amersham International) is used to assess the incorporation of $^{32}P$ radioactivity into Crosstide. In this system, the sample (containing GST-ΔN-SGK activated by PDK1 or GST-ΔN-SGK[Ser422Asp] activated by PDK1, the compound to be tested and [γ-$^{32}$P]ATP or [γ-$^{33}$P]ATP is mixed with beads comprising scintillant and antibodies that bind Crosstide. Conveniently this is done in a 96-well format. The plate is then counted using a suitable scintillation counter, using known parameters for $^{32}$P or $^{33}$P SPA assays. Only $^{32}$P or $^{33}$P that is in proximity to the scintillant, i.e. only that bound to Crosstide that is then bound by the antibody, is detected.

EXAMPLE 3

Assay for Compounds which Modulate SGK Activity

An assay is set up with Crosstide, as described in Example 1 or Example 2. Compounds are tested in the assay and those that give rise to inhibition or activation of SGK are selected for further study. Compounds are further tested for effects on PKBα and those that do not affect the phosphorylation of Crosstide by PKBα are selected.

The compounds tested may be compounds selected on the basis of known properties, for example ability to inhibit other protein kinases, such as PKBα, or may be part of a library of compounds assembled for testing in a variety of screens, for example in a "lead generation" screening programme. The compounds may be natural or synthetic, and may be generated by combinatorial chemistry, as known to those skilled in the art.

The selected compounds may be used in the design of further compounds for manufacture and test, in order to develop a structure-activity relationship (SAR).

EXAMPLE 4

Assay for Polypeptides that Interact with SGK

A yeast two hybrid assay system is set up to identify polynucleotides encoding polypeptides that are capable of associating with SGK in a stable enough manner to allow transcriptional activation to occur. The polynucleotides are (in separate experiments) cDNAs copied from mRNA from cells that are capable of expressing SGK, before or after stimulation capable of stimulating expression of SGK, before or after further stimulation capable of activating the expressed SGK, and from cells which do not express SGK. Interactions which are found in a subset only of these cell types are of particular interest.

The polypeptide encoded by the polynucleotide is determined by sequencing the insert by the Sanger method as described in Example 1 and well known to those skilled in the art to obtain a predicted amino acid sequence.

REFERENCES

1. Cohen et al (1997) FEBS Lett 410, 3–10.
2. Alessi & Cohen (1998) Curr Opin. Genet. Dev. 8, 55–62
3. Franke et al (1995) Cell 81, 727–736.
4. Burgering & Coffer (1995) Nature 376, 599–602.
5. Kohn et al (1995) EMBO J. 14, 4288–4295.
6. Alessi et al (1996) EMBO J. 1 5, 6541–6551.
7. Alessi et al (1997) Curr. Biol. 7, 261–269.
8. Stokoe et al (1997) Science 277: 567–570.
9. Alessi et al (1997) Curr. Biol. 7, 776–789.
10. Stephens et al (1998) Science 279, 710–714.
12. Andjelkovic et at (1997) J. Biol. Chem. 272, 31515–31324.
11. Currie et at (1998) Biochem J. 337, 575–583.
13. Goransson et at (1998) Biochem. Biophys. Res. Commun. 246, 249–254.
14. Anderson et at (1998) Curr. Biol. 8, 684–691
15. Alessi et al (1998) Curr. Biol. 8, 69–81.
16. Pullen et at (1998) Science 279, 707–710.
17. Le Good et at (1998) Science 281(5385):2042–5.
18. Webster et at (1993) Mol. Cell. Biol. 13, 1031–2040.
19. Webster et at (1993) J. Biol. Chem. 268, 11482–114485
20. Richards et at (1995) Hormone Res. 50, 223–255
21. Waidegger et al (1997) Proc.Natl.Acad.Sci. USA 94, 4440–4445
22. Hollister et at (1997) Neurosci Lett. 79, 1111–1119
23. Imaizumi et at (1994) Mol. Brain Res. 26, 189–196
24. Maiyar et at (1996) J. Biol. Chem. 271, 12414–14222
25. Maiyar et at (1997) Mol. Endocrinol. 11, 312–329
26. Boyle et at (1991) Methods Enzymol. 201, 110–149.
27. MacKintosh et at (1991) FEBS Lett 264, 187–192.
28. Pearson et at (1995) EMBO J. 14, 5279–5287.
29. Stokoe et at (1992) EMBO J. 11, 3985–3994.
30. Cross et at (1995) Nature 378, 785–789.

EXAMPLE 5

Characterisation of the Structure and Regulation of Two Novel Isoforms of Serum and Glucocorticoid-Induced Protein Kinase Abbreviations:—SGK, serum and glucocorticoid-regulated protein kinase; PKB, protein kinase B, PDK1,3-phosphoinositide-dependent protein kinase-1; protein kinase C-related protein kinase-2 (PRK2); PI, phosphatidylinositol; IGF1, insulin-like growth factor-1; GSK3, glycogen synthase kinase-3; GST, glutathione S-transferase; PMA, phorbol myristate acetate; PP2A, protein phosphatase 2A; PCR, polymerase chain reaction.

We show in Example 1 and [18] and subsequently others [19] have shown that, like PKB, SGK is also activated within minutes via a phosphorylation mechanism when cells are stimulated with insulin, insulin-like growth factor-1 (IGF1) or serum, or exposed to oxidative stress.

Here, we identify two novel isoforms of SGK, termed SGK2 and SGK3, which are the products of distinct genes, and compare their tissue distribution, induction by serum and glucocorticoids, activation by phosphorylation and substrate specificity with SGK (hereafter termed SGK1). Despite, their high degree of sequence similarity with SGK1, the mechanisms that regulate the level and activity of SGK2 and SGK3 differ significantly from SGK1 in several respects.

Like SGK1, the mRNA encoding SGK3 is expressed in all tissues examined, but SGK2 mRNA is only present at significant levels in liver, kidney and pancreas and, at lower levels, in the brain. The levels of SGK2 mRNA in H4IIE cells and SGK3 mRNA in Rat2 fibroblasts are not increased by stimulation with serum or dexamethasone, whereas the level of SGK1 mRNA is increased greatly by one or both agonists. SGK2 and SGK3 are activated in vitro by PDK1, albeit more slowly than SGK1, and their activation is accompanied by the phosphorylation of Thr193 and Thr253, respectively, the residues equivalent to the Thr in the "activation loop" of PKB that is targetted by PDK1. The PDK1-catalysed phosphorylation and activation of SGK2 and SGK3, like SGK1, is greatly potentiated by mutating Ser356 and Ser419, respectively, to Asp, these residues being equivalent to the C-terminal phosphorylation site of PKB. Like SGK1, SGK2 and SGK3 are activated five-fold via a phosphorylation mechanism when cells are exposed to hydrogen peroxide but, in contrast to SGK1, activation is only suppressed partially by inhibitors of PI 3-kinase. SGK2 and SGK3 are activated to a smaller extent by IGF1 (2-fold) than SGK1 (5-fold). Like PKB and SGK1, SGK2 and SGK3 preferentially phosphorylate Ser and Thr residues that lie in Arg-Xaa-Arg-Xaa-Xaa-Ser/Thr (SEQ. ID. NO:46) motifs. This raises the possibility that some physiological roles ascribed to PKB on the basis of overexpression studies with constitutively active mutant enzyme, may be mediated by isoforms of SGK.

Materials and Methods

Materials. Human PDK1 was expressed as a glutathione S-transferase (GST) fusion protein in 293 cells and purified by affinity chromatography on glutathione-Sepharose [5]. Dexamethasone, wortmannin and LY 294002 were purchased from Sigma (Poole, U.K.). All peptides were synthesized by Dr Graham Blumberg (Department of Biochemistry, University of Bristol, U.K.). Expression plasmids of SGK1 and an N-terminally truncated form of SGK1(SGK1[61–431]) were identical to pEBG-SGK and pEBG-ΔN-SGK[61–431] described in Example 1 and [18]. The pEBG-2T-2 vector was made by insertion with 5'-GAT CTC GGA TCC ACT AAC GGT AC-3' (SEQ. ID. NO:11) and 5'-CGT TAG TGG ATC CGA-3' (SEQ. ID. NO: 12) between BamHI and KpnI sites of pEBG-2T. This introduced a new BamHI site which was located in a different reading frame from the original pEBG-2T vector.

Buffer solutions. Buffer A comprised 50 mM Tris/HCl, pH 7.5, 1 mM EDTA, 1 mM EGTA, 1% (w/v) Triton X-100, 1 mM sodium orthovanadate, 50 mM NaF, 5 mM sodium pyrophosphate, 0.27 M sucrose, and 0.1% (v/v) 2-mercaptoethanol. Buffer B comprised 50 mM Tris/HCl, pH 7.5, 1 mM EGTA, 0.1% (v/v) 2-mercaptoethanol. Buffer C comprised 50 mM Tris/HCl, pH 7.5, 150 mM NaCl, 0.1 mM EGTA, 0.5 mM dithiothreitol and 1 mg/ml bovine serum albumin. Cell lysis buffer was Buffer A containing 1 μM microcystin-LR, 0.2 mM phenylmethylsulphonyl fluoride and protease-inhibitor cocktail (one tablet/500 ml).

Cloning of SGK isoforms. A full length clone encoding human SGK2 was obtained as follows. Analysis of expressed sequence tag (EST) AA130828 (IMAGE Consortium, St. Louis, Mo., USA) showed that it encoded a novel kinase which was homologous to human SGK1. A 5'-RACE was then carried out using human kidney cDNA (Marathon-Ready cDNA, Clontech, Calif., USA) as a template, since there was no stop codon upstream of first ATG. The primers used for 5'-RACE of SGK2 were 5'-GCT CTG GAC TTG GGG TCC CAG CTG GGC-3' (SEQ. ID. NO:13), 5'-GTT GAT GTT CCC ATT GGC CCT GGA GGG-3' (SEQ. ID. NO:14) and 5'-GCT GGG CAT TTG GGT TGG CTG AAG GCC-3' (SEQ. ID. NO:15). Fragments of 200–220 bp were obtained in all three cases and the PCR products were cloned into the pCR-2.1-TOPO vector (Invitrogen, USA). Eight clones out of 10 clones analysed possessed a 200 bp fragment and sequence analysis showed that these corresponded to the 5' portion of EST AA130828. We designated this protein kinase as SGK2α. Two other clones had longer fragments (500 and 600 bp). Sequence analysis showed that these clones corresponded to another form of SGK2 with an additional 60 amino acid residues at the N-terminus and a different 5' non-coding region. This enzyme was designated SGK2β. A mouse clone (accession number AI 386362) was also identified by interrogating the NCBI EST database with the sequence of human SGK2α, that was predicted to encode a full length protein of mouse SGK2α. We also assembled the full length murine cDNA using the clones AA790370 (which encodes the first 1240 nucleotides) and AA138663 (that starts from nucleotide 1140 and terminates in the polyA tail).

A full length clone encoding human SGK3 was obtained as follows. Analysis of EST AA219166 (IMAGE Consortium) showed that it encoded the partial sequence of a novel protein kinase which had homology to SGK1 and SGK2. Since this cDNA contained a gap in the central portion, a PCR reaction was carried out using a human skeletal muscle library as a template. The Primers used for the PCR were 5'-AACATCCGTTTTTGGTTGGATTGC-3' (SEQ. ID. NO:16) and 5'-GGGTAGATGTTAGTGTAAAC-3' (SEQ. ID. NO:17). Since this clone did not contain an initiating ATG codon, 5'-RACE was carried out using human kidney cDNA as a template. The primers used for 5'-RACE were 5'-ATA AAG TTC TGG ATA CCT AAC TAG G-3' (SEQ. ID. NO:18), 5'-GAA GGA ATG CTC TGA CAT CTG GAT GG-3' (SEQ. ID. NO:19) and 5'-GAT CTG ACT GGT GTT TTG GAC TGT CC-3') (SEQ. ID. NO:20). Unlike the 5' RACE of SGK2, which showed sharp bands of PCR products when analysed on an agarose gel, that of SGK3 produced a smear. We therefore ligated these heterogeneous products into a pCR-2.1-TOPO vector (Invitrogen, USA) and analyzed the 20 clones obtained. Sequence analysis revealed that 12 clones contained the missing part of the new SGK sequence, which we called SGK3.

In order to introduce a BamHI site at the 5'-end in-frame with the GST sequence of the pEBG-2T-2 vector, and a NotI site at the 3'-end of each open reading frame, PCR amplification was performed using the following primers: SGK2α: 5'-GGA TCC AGC TGC CTG ATC ATT GCT AC-3' (SEQ. ID. NO:21) and 5-GCG GCC GCC TAG CAA TCC AAG ATG TCA TC-3 (SEQ. ID. NO:22); SGK2β: 5'-GGA TCC CAG GGG TTG CTT ACC TCG GG-3' (SEQ. ID. NO:23) and 5'-GCG GCC GCC TAG CAA TCC AAG ATG TCA TC-3' (SEQ. ID. NO:24); full length SGK3: 5'-GGA TCC AAG CCC TGA AGA AGA TTC CTG CC-3' (SEQ. ID. NO:25) and 5'-GCG GCC GCT CAC AAA AAT AAG TCT TC-3' (SEQ. ID. NO:27); SGK3 lacking the N-terminal 52 residues (ΔN-SGK3[53–429]): 5'-GGA TCC TGG ACA GTC CAA AAC ACC AG-3'(SEQ. ID. NO:28) and 5'-GCG GCC GCT CAC AAA AAT AAG TCT TC-3' (SEQ. ID. NO:29). The PCR products were cloned into a pCR-2.1-TOPO vector (Invitrogen) and sequenced. Each fragment was digested with BamHI and NotI and inserted into the cloning site of pEBG-2T-2. Ser356 of SGK2α and Ser419 of SGK3 were mutated to Asp by in vitro mutagenesis using PCR.

Expression of SGK isoforms in 293 cells. Each 6 cm and 10 cm diameter dish of cells were transfected with 10 μg or 3 μg, respectively, of the pEBG-SGK constructs using a modified calcium-phosphate method [3]. At 24 h after transfection, the cells were deprived of serum for 16 h, then stimulated in one of the following ways: 50 ng/ml IGF-1 (10 min), 400 ng/ml phorbolmyristate acetate (PMA) (30 min), 10% foetal bovine serum (30 min), 1 μM dexamethasone (60 min), 2 mM $H_2O_2$ (25 min), 5 μg/ml anisomycin (30 min), 0.4 M sorbitol (30 min), 30 min of hypo-osmotic stress (3 ml of DMEM diluted to 4 ml with water) and UV-C irradiation (200 $J/m^2$). After each treatment, the cells were lysed and the activity of SGK isoforms was measured after affinity purification of the GST-fusion proteins on glutathione Sepharose, as described previously for SGK1 [18].

Dephosphorylation, Phosphorylation and Assay of SGK Isoforms in Vitro.

Each GST-SGK isoform (0.4 μg) was incubated for 20 min at 30° C. with protein phosphatase 2A (PP2A, 30 mU/ml) in a 10 μl incubation containing 20 mM Tris/HCl, pH 7.5, 0.1% (v/v) 2-mercaptoethanol, 0.1 mM EGTA and 1 mg/ml bovine serum albumin. After addition of microcystin-LR to 1 μM to inactivate PP2A, SGK (0.4 μg) was phosphorylated for 30 min at 30° C. in a mixture (20 μl) containing 50 mM Tris/HCl, pH 7.5, 10 mM MgCl2, 0.1% (v/v) 2-mercaptoethanol, 0.1 mM EGTA, GST-PDK1 (0.03–300 ng) diluted in Buffer C and 100 μM unlabelled ATP. SGK assays were initiated by the addition of 30 μl of a mixture containing 50 mM Tris/HCl, pH 7.5, 10 mM $MgCl_2$, 0.1% (v/v) 2-mercaptoethanol, 0.1 mM EGTA, 100 μM [γ-$^{32}$P] ATP (500 c.p.m/pmol), 50 μM of the peptide substrate Crosstide (GRPRTSSFAEG) (SEQ. ID. NO:30) and 4.2 μM of residues 5–24 of the specific protein inhibitor of adenosine 3'5' cyclic monophosphate-dependent protein kinase. After 10 min at 30° C., the reactions were terminated by spotting aliquots on to P81 phosphocellulose paper, followed by immediate immersion in 75 mM phosphoric acid. The papers were washed, dried and analysed [3]. One unit (U) of SGK was that amount which phosphorylated 1 nmole of Crosstide in one min.

Preparation of RNA and Northern blotting. Rat2 fibroblasts or H4IIE hepatoma cells ($10^6$ cells) were plated on to 10 cm dishes and incubated for 24 h in Dulbecco's modified Eagles' medium (DMEM) containing 10% foetal bovine serum (FBS). The medium was changed to DMEM without serum and the cells incubated for a further 24 h. After stimulation with 10% FBS and 1 μM dexamethasone, total RNA was isolated from the cells using an RNeasy Mini kit (QIAGEN, West Sussex, UK). RNA (5 μg) was electrophoresed through 1.2% agarose gels in presence of 0.67 M formaldehyde, transferred to Hybond-N+(Amersham Pharmacia Biotech, UK) and cross-linked under ultraviolet light (UV Stratalinker, Stratagene, La Jolla, Calif., USA). $^{32}$P-labelled probes were generated by labelling the open reading frames of each SGK isoform with [γ-$^{32}$P] DATP using a Multiprime DNA labelling kit (Amersham Pharmacia Biotech) Hybridization was performed in Rapid-hyb buffer (Amersham Pharmacia Biotech) for 2 h at 65° C. Membranes were washed with 2×SSC/0.1% SDS for 30 min at room temperature and then for 15 min at 65° C., then washed with 0.2×SSC/0.1% SDS for 15 min at 65° C. and exposed to X-ray film (Hyperfilm, Amersham) at −70° C. for 3–5 days.

Results.

Cloning of novel SGK isoforms. SGK was originally identified as a glucocorticoid and osmotic stress-responsive gene (see Introduction). Searching for new SGK isoforms, the NCBI database was interrogated with the sequence of SGK. This search identified two human ESTs that showed considerable similarity to the original gene. Sequence analysis of these ESTs revealed that they represent two new isoforms of the SGK gene family, that we term SGK2 and SGK3. The original SGK isoform is therefore termed SGK1.

As none of these ESTs were full length clones, 5' RACE and PCR reactions were carried out to obtain the missing parts of the sequence (see Methods). This led to the identification of two splice variants of SGK2, termed SGK2α and SGK2β (FIG. 11). SGK2α encodes a protein of 368 residues with a calculated molecular mass of 41.1 kDa, SGK2β a protein of 428 amino acids with a calculated molecular mass of 47.6 kDa. An EST encoding murine SGK2α was also identified (FIG. 13). Unlike human SGK2α, the murine cDNA contains an in-frame stop codon immediately preceding the initiating Met. This establishes that the shortest splice variant does indeed start at this position.

The nucleotide sequence of SGK3 contained two in frame ATG codons (FIG. 12). The sequence surrounding the second ATG conforms more closely to the consensus that frequently surrounds initiation codons. Moreover, a stop codon (TAA) is present immediately upstream of the first ATG (FIG. 12). For these reasons, the site of initiation is assumed to be the second ATG. This would encode a 430 residue 49.0 kDa protein. If the first ATG is used for initiation, it would generate a polypeptide 62 amino acids longer.

The amino acid sequences of the three SGK isoforms are about 80% identical to one another in the catalytic domain, while the short C-terminal non-catalytic domains are less similar (44–68% identity). The N-terminal 85 residues that precede the catalytic domain are much less similar. In this region there is only about 25% identity between SGK1 and SGK3 and almost no identity between SGK2 and the other isoforms (FIG. 13).

Tissue distribution of SGK isoform mRNAs. As reported previously by others [13], the level of SGK1 mRNA was similar in all tissues tested, with a major 2.6 kb transcript and a minor 7 kb transcript. The highest levels of both transcripts were in the pancreas. The level of SGK3 mRNA was also similar in each tissue, with a major 5 kb transcript in each case. In contrast, mRNA which hybridises with a probe that recognises SGK2α and SGK2β had a much more restricted tissue distribution, 2.1 kb and 4.0 kb transcripts being present in liver, kidney, pancreas and brain (FIG. 14). An SGK2β-specific probe also recognised transcripts in liver and kidney, but the levels were much lower and the signal was rather diffuse.

Effect of serum and dexamethasone on the level of SGK isoform mRNA in Rat2 fibroblasts and H4IIE hepatoma cells. SGK1 is an immediate early gene and its mRNA increases greatly within one hour of stimulation with serum and glucocorticoids in several cell lines [11]. We therefore examined the effects of these stimuli on mRNA encoding all three SGK isoforms. In Rat2 fibroblasts SGK1 mRNA was strongly induced by serum or dexamethasone after 2 h as expected, whereas the level of SGK3 mRNA was not affected by these agonists. SGK2 mRNA was not expressed in Rat2 fibroblasts (FIG. 15A). In rat H4IIE hepatoma cells dexamethasone, but not serum, induced the formation of SGK1 mRNA, whereas the level of SGK2 mRNA was unaffected by either agonist. SGK3 mRNA was not expressed in H4IIE cells (FIG. 15B)

Expression of SGK isoforms in 293 cells. All three isoforms were expressed as GST-fusion proteins in 293 cells. The sizes of GST-SGK2α (70 kDa), GST-SGK3 (75 kDa) and GST-ΔN-SGK3 (70 kDa) were consistent with their calculated molecular masses (FIG. 16). However, nearly all the GST-SGK2β was expressed as free GST (25 kDa) presumably due to proteolysis of the full length fusion protein (FIG. 16, lane 3). Deletion of the N-terminal region of SGK3 improved its level of expression (FIG. 16, lanes 5 and 6), although not to the same extent as SGK1 (FIG. 16, lanes 1 and 2). Typically 400 μg, 100 μg and 150 μg of 90% pure GST-ΔN-SGK1[61–431], 80% pure GST-SGK2α and 90% pure GST-ΔN-SGK3[53–429], respectively, were obtained from ten, 10 cm diameter dishes of cells.

Phosphorylation and activation of SGK isoforms by PDK1. The two key phosphorylation sites corresponding to residues Thr308 and Ser473 of PKBα [3] are conserved in SGK2 (Thr193 and Ser356 in SGK2α) and SGK3 (Thr253 and Ser419), as well as SGK1 (Thr256 and Ser422). We (Example 1 and [18]) and subsequently others [19] have shown that PDK1 activates wild type SGK1 in vitro by phosphorylating Thr256 (see also FIGS. 17A and 17D). Wild type SGK2α and SGK3 were also activated by PDK1 in vitro, although higher concentrations of PDK1 were required for activation (FIGS. 17B and 17C) and phosphorylation (FIGS. 17E and 17F), especially with SGK2. Maximal activation of all SGK isoforms was observed after incubation for 30 min with 1.5 μg/ml PDK1 (FIGS. 17A, 17B and 17C). At this concentration of PDK1, the stoichiometries of phosphorylation were close to 1 mol/mol for SGK1 and SGK3 and 0.2 mol/mol for SGK2 (data not shown). If the PDK1 concentration was increased 10-fold, the level of phosphorylation of SGK2 and SGK3 increased considerably, but without any further activation (FIGS. 17D, 17E and 17F). This suggested that PDK1 is capable of phosphorylating other sites on SGK2 and SGK3 that do not affect activity directly.

We have demonstrated that an SGK1 mutant in which Ser422 (the PDK2 site) is mutated to aspartic acid has a specific activity more than 10-fold higher than that of the wild type enzyme after expression in 293 cells (Example 1 and [18]). This high basal activity results from increased phosphorylation at Thr256, and can be abolished by treatment with PP2A (Example 1 and [18]). In the present study, we found that PP2A-treated SGK1 [Ser422Asp] was reactivated (FIG. 17A) and phosphorylated (FIG. 17D) at a much higher rate than PP2A-treated wild type SGK1.

The corresponding mutants of SGK2 and SGK3 in which the serines equivalent to Ser422 of SGK1 were mutated to aspartic acid (SGK2[Ser356Asp] and SGK3[Ser419Asp]) also had high activities after expression in 293 cells (data not shown). After treatment with PP2A, SGK2α was inactivated and, as for SGK1, SGK2[Ser356Asp] was activated (FIG. 17B) and phosphorylated (FIG. 17E) by PDK1 much more effectively than wild type SGK2α. In contrast SGK3 [Ser419Asp] could not be inactivated by PP2A and incubation with PDK1 and MgATP did not increase activity further (FIG. 17C). SGK3[Ser419Asp] did however become phosphorylated upon incubation with MgATP even in the absence of PDK1 (FIG. 17F), presumably as a result of autophosphorylation. Phosphorylation did not appear to be catalysed by PDK1 present as a contaminant, because no PDK1 could be detected in the preparation by immunoblotting (data not shown).

The SGK2[Ser356Asp] mutant and wild type SGK3 were incubated for 30 min at 30° C. using 1.5 μg/ml PDK1 and MgATP which led to the incorporation of 1.2 and 1.3 mol phosphate per mol protein, respectively. The reactions were terminated, digested with trypsin and phosphopeptides chromatographed on a C18 column as in Example 1 and [18] (FIG. 18). The major phosphothreonine-containing peptides from the SGK2 and SGK3 digests (peptides P2 and P5 in FIGS. 18A and 18B) were subdigested with N-Asp proteinase and subjected to MALDI-TOF mass spectrometry and solid phase Edman sequencing [20] to identify the sites of phosphorylation. These experiments revealed that the phosphopeptide from SGK2 corresponded to residues 189–207 phosphorylated at Thr193, while the SGK3 phosphopeptide corresponded to residues 249–267 phosphorylated at Thr253. These experiments establish that PDK1 does indeed phosphorylate SGK2 and SGK3 at sites equivalent to Thr256 of SGK1.

The phosphoserine-containing tryptic peptides P1, P3 and P4 (FIG. 18) were also analysed by MALDI-TOF mass spectrometry and Edman sequencing. These experiments revealed that peptide P1 corresponded to residues 277–287 phosphorylated at Ser279, while peptide P3 comprised residues 334–367 phosphorylated at Ser334. Peptide P4 corresponded to residues 73 to 99 and was phosphorylated at either Ser75 or Ser77; the latter was the major site of phosphorylation. These findings are considered further under discussion.

The activation of SGK2 and SGK3 by PDK1 was unaffected by lipid vesicles containing phosphatidylserine and phosphatidylcholine, and slightly inhibited by the further inclusion of 10 μM PI 3,4,5-trisphosphate (data not shown). These results are similar to those obtained previously with SGK1.

Substrate specificities of SGK isoforms. We have shown that SGK1 and PKB have similar specificities towards a panel of synthetic peptides, preferentially phosphorylating serine and threonine residues that lie in Arg-Xaa-Arg-Xaa-Xaa-Ser/Thr motifs (Example 1 and [18]). In the present Example, the specificity requirements of SGK2α and SGK3 were also found be similar (Table 2), although SGK3 appears to tolerate the presence of a lysine instead of an arginine at position n-3 (when n is the site of phosphorylation) a little better than SGK1 or SGK2α (Table 2).

TABLE 2

Comparison of the activity of SGK isoforms toward synthetic peptides related to Crosstide.
The experiments were carried out with GST-ΔN-SGK1[S422D], GST-SGK2α[S356D] and GST-ΔN-SGK3[S419D] purified from 293 cells. The activities are presented relative to peptide 1 (Crosstide). The concentration of each peptide was 30 µM. Amino acid substitutions to peptide 2 are underlined. The result shown is the average of two experiments each agreeing to ±10%.

| Peptide | SGK1 activity % | SGK2 activity % | SGK3 activity % |
| --- | --- | --- | --- |
| 1 GRPRTSSFAEG (SEQ. ID. NO: 30) | 100 | 100 | 100 |
| 2 RPRTSSF (SEQ. ID. NO: 39) | 135 | 182 | 137 |
| 3 RPRTSAF (SEQ. ID. NO: 32) | <1 | <1 | <1 |
| 4 PRTSSF (SEQ. ID. NO: 33) | <1 | <1 | <1 |
| 5 RPRTSS (SEQ. ID. NO: 31) | 5.1 | 8 | 18 |
| 6 RPRTSTF (SEQ. ID. NO: 35) | 129 | 192 | 156 |
| 7 RPRAATF (SEQ. ID. NO: 36) | 44 | 61 | 56 |
| 8 KPRTSSF (SEQ. ID. NO: 37) | <1 | <1 | <1 |
| 9 RPKTSSF (SEQ. ID. NO: 38) | 11 | 8 | 48 |
| 10 RPRTSSF (SEQ. ID. NO: 39) | 135 | 182 | 137 |
| 11 RPRTSSL (SEQ. ID. NO: 40) | 108 | 185 | 113 |
| 12 RPRTSSV (SEQ. ID. NO: 41) | 90 | 124 | 139 |
| 13 RPRTSSA (SEQ. ID. NO: 42) | 49 | 82 | 123 |
| 14 RPRTSSK (SEQ. ID. NO: 43) | 84 | 128 | 200 |
| 15 RPRTSSE (SEQ. ID. NO: 44) | 28 | 34 | 67 |

Activation of SGK isoforms in 293 cells. Each SGK isoform was expressed in 293 cells and their ability to be activated acutely by a variety of stimuli was examined. As reported previously (Example 1 and [18, 19]), stimulation with IGF1 induced a four to five-fold increase in SGK1 activity (FIG. 19), which reached a maximum after 10 min (data not shown). In contrast, SGK2α and SGK3 were only activated two-fold by IGF1 (FIG. 19). Activation was maximal after 5 min and sustained for at least 20 min (data not shown). The agonist which produced the strongest activation of SGK2α and SGK3 (5-fold) was hydrogen peroxide similar to that observed with SGK1 (FIG. 19). Serum was also a weak activator of all three isoforms. However, osmotic shock (treatment with 0.4M sorbitol), which potently inhibited SGK1, had no effect on the activity of SGK2α or SGK3 (FIG. 19).

The activation of SGK2 and SGK3 induced by hydrogen peroxide was only inhibited partially when the cells were preincubated with wortmannin or LY 294002 (two inhibitors of PI 3-kinase) prior to stimulation with hydrogen peroxide. In contrast, the activation of SGK1 was abolished (FIG. 20).

Discussion. In this Example we identify two novel isoforms of SGK1, termed SGK2 and SGK3, which share 80% identity with SGK1 in their catalytic domains. Nevertheless, despite this similarity, SGK2 and SGK3 differ significantly from each other, and from SGK1, in a number of respects. Firstly, the mRNAs encoding SGK1 and SGK3 are widely expressed, but that encoding SGK2 has a more restricted distribution, being highly expressed in liver, kidney and pancreas and, at lower levels, in the brain (FIG. 4). Secondly, SGK2 mRNA and SGK3 mRNA are not increased by cell stimulation with serum or glucocorticoids (FIG. 15), whereas SGK1 mRNA levels increase greatly within 1 h of exposure to these agonists ([11], FIG. 15).

SGK2 and SGK3 are activated by PDK1 in vitro, albeit more slowly than SGK1 (FIG. 17), and activation is accompanied by the phosphorylation of the same residue in the "activation loop" between kinase subdomains VII and VIII (Thr256 in SGK1, Thr193 in SGK2 and Thr253 in SGK3). Moreover, like SGK1 (Example 1 and [18]) and p70 S6 kinase [9], the PDK1-catalysed phosphorylation and activation of SGCK2 and SGK3 in vitro is greatly potentiated by mutation to Asp of the C-terminal Ser (Ser422 in SGK1, Ser356 in SGK2 and Ser419 in SGK3), suggesting that phosphorylation of this residue is a prerequisite for the PDK1-catalysed phosphorylation of the activation loop Thr. These observations raise the question of the identity of the protein kinase(s) that phosphorylates SGK isoforms at the C-terminal Ser. PDK1 is converted to a form that phosphorylates PKB at Ser473 as well as Thr308 by interaction with a peptide corresponding to the C-terminal sequence of PRK2 [6]. Whether PDK1 can be converted to a form that phosphorylates SGK isoforms at both sites by interaction with a different protein, or whether this residue is phosphorylated by a distinct protein kinase in vivo, remains to be established.

In contrast to SGK1, which is phosphorylated by PDK1 at one major site (Thr256; Example 1 and [18]), SGK2 and SGK3 become phosphorylated at two additional serine residues when incubated with PDK1 and MgATP (FIG. 18). SGK2 is phosphorylated at Ser279 and Ser334, as well as Thr193. The sequence surrounding Ser334 (Ser-Ile-Gly-Cys-Thr-Pro-Asp-Thr-Val-Ala) (SEQ. ID. NO:50) resembles that surrounding Thr193 (Thr-Phe-Cys-Gly-Thr-Pro-Glu-Tyr-Leu-Ala) (SEQ. ID. NO:51) (FIG. 13), suggesting that Ser334 is phosphorylated by PDK1 and raising the possibility that physiological substrates of PDK1 might include proteins that are not kinases. Serines equivalent to Ser334 are present in SGK1 and SGK3 (FIG. 3), but are not phosphorylated significantly by PDK1 [18] (FIG. 18). The reason for this is unclear, but may be related to the particular amino acid replacements that occur in the vicinity of this residue.

Interestingly, Ser279 lies in an Arg-Xaa-Arg-Xaa-Xaa-Ser (SEQ. ID. NO:46) sequence (FIG. 13), which conforms to the optimal consensus for phosphorylation by SGK and PKB [18, 22]. This suggests that Ser279 phosphorylation is likely to be an autophosphorylation event catalysed by SGK2 itself after it has been activated by PDK1. This finding also raises the intriguing possibility that Ser279 may be phosphorylated by another protein kinase in vivo, such as another SGK isoform or PKB. It will clearly be of considerable interest to examine whether Ser279 phosphorylation occurs in cells and tissues and whether it alters the catalytic and regulatory properties of SGK2. Ser279 is not conserved in either SGK1 or SGK3 (FIG. 13).

SGK3 also became phosphorylated at two serines (Ser77 and Ser79) upon incubation with PDK1 and MgATP, which are not conserved in SGK1 or SGK2 (FIG. 13). Although these residues do not lie in optimal consensus sequences for either SGK or PDK1, they are probably autophosphorylation events catalysed by SGK3 for two reasons. Firstly, activated SGK3 autophosphorylates in the absence of PDK1 (FIG. 17F); secondly the SGK3 concentration in these incubations is very high compared to those used with optimal peptide substrates; thirdly, basic residues (Lys74 and His 76) are present three residues N-terminal to Ser 77 and Ser79, which is one of the prerequisites for phosphorylation by SGK.

The response of SGK2 and SGK3 to agonists also differs in several respects from SGK1. For example, SGK2 and SGK3 are activated by IGF1 to a smaller extent (although just as rapidly) as SGK1 (FIG. 19). The activation in response to hydrogen peroxide is similar for all three isoforms (five fold), but inhibitors of PI 3-kinase only suppress the activation of SGK2 and SGK3 partially, whereas the activation of SGK1 is abolished (FIG. 20). In addition, SGK2 and SGK3 activities are unaffected by exposure to osmotic stress, whereas SGK1 (FIG. 19) and PKB [23] activities are virtually abolished. The subcellular localisation of SGK2 and SGK3 may be compared with that of SGK1. These isoforms may translocate to the nucleus or another organelle(s) in response to different agonists in a similar manner to SGK1 [19]. The development of isoform-specific antibodies sufficiently sensitive to detect the endogenous levels of SGK2 and SGK3 may be useful in determining the subcellular location of SGK2 and SGK3.

A number of physiological roles have been ascribed to PKB based on results obtained by overexpression of constitutively active mutants (reviewed in [1, 2]). However, SGK isoforms have a similar specificity to PKB (Table 2) and are activated in vivo by the same stimuli. Moreover, SGK1 can mimic the ability of PKB to inactivate glycogen synthase kinase 3 (GSK3) in vitro and in cotransfection experiments (Example 1 and [18]). It is therefore possible that some physiological roles thought to be performed by PKB are mediated by an SGK isoform. Conversely, activation of the epithelial sodium channel produced by coexpression with SGK1 in *Xenopus oocytes* [16] may really mediated by another SGK isoform or by PKB.

REFERENCES FOR EXAMPLE 5

1. Alessi & Cohen, P (1998) *Curr. Opin. Genet. Dev.* 8, 55–62.
2. Cohen, P. (1999) *Phil. Trans. R. Soc. Lond.* B 354, 485–495.
3. Alessi et al (1996) *EMBO J.* 15, 6541–6551.
4. Alessi et al (1997) *Curr. Biol.* 7, 261–269.
5. Alessi et al (1997) *Curr. Biol.* 7, 776–789.
6. Balendran et al (1999) *Curr. Biol.* 9, 393–404.
7. Le Good et al (1998) *Science* 281, 2042–2045.
8. Dutil et al (1998) *Curr. Biol.* 8, 1366–1375.
9. Alessi et al (1998) *Curr. Biol.* 8, 69–81.
10. Pullen et al (1998) *Science* 279, 710–714.
11. Webster et al (1993) *J. Biol. Chem.* 268, 11482–114485.
12. Richards et al (1995) *Hormone Res.* 50, 223–255.
13. Waldegger et al (1997) *Proc.Natl.Acad.Sci. USA* 94, 4440–4445.
14. Hollister et al (1997) *Neurosci Lett.* 79, 1111–1119.
15. Imaizumi et al (1994) *Mol. Brain Res.* 26, 189–196
16. Naray-Fejes-Toth et al (1999) *J. Biol. Chem.* 274, 16973–16978.
17. Maiyar et al (1996) *J. Biol. Chem.* 271, 12414–14222.
18. Kobayashi & Cohen, P. (1999) *Biochem. J.* 339, 319–328.
19. Park et al (1999) *EMBO J.* 18, 3024–3033.
20. Morrice & Powis, S. J. (1998) *Curr. Biol.* 8, 713–716.
21. Balendran, A, Currie, R., Armstrong, C., Avruch, J. and Alessi, D. R. (1999) submitted
22. Alessi et al (1996) *FEBS Lett.* 399, 333–338.
23. Meier et al (1998) *EMBO J.* 17, 7294–7303.
24. Thompson et al (1994) *Nuc. Acids Res.* 22,4673–4680.
25. Cuenda et al (1996) *EMBO J.* 15, 4156–4164.

The invention claimed is:

1. A method of activating a serum and glucocorticoid-induced protein kinase (SGK) comprising:
   contacting a SGK comprising SEQ ID NO:45 or SEQ ID NO:48 or both with a compound wherein the SGK is phosphorylated by the compound and wherein the compound has PDK1 or PDK2 activity.

2. A method according to claim 1 wherein the SGK is phosphorylated on the residue equivalent to Thr256 of full-length human SGK1.

3. A method according to claim 1 wherein the SGK is phosphorylated on the residue equivalent to Ser422 of full-length human SGK1.

4. A method according to claim 3 wherein the SGK is further phosphorylated on the residue equivalent to Thr256 of full-length human SGK1.

5. The method according to claims 1, 2, or 3, wherein the SGK is SGK1, SGK2α, SGK2β or SGK3.

6. The method according to claims 1, 2, or 3 wherein the compound phosphorylates a polypeptide which comprises SEQ ID NO:48.

7. The method according to claim 1, 2, or 3 wherein the compound having PDK2 activity phosphorylates a polypeptide which comprises SEQ ID No:45.

8. The method according to claim 1, wherein the SGK is capable of phosphorylating a polypeptide comprising SEQ ID NO:49.

9. The method according to claim 8, wherein the SGK SEQ ID NO:1, SEQ ID NO:3, SEQ ID NO:4 or SEQ ID NO:8.

10. The method according to claim 1, wherein the compound is in a preparation.

* * * * *

SEQUENCE LISTING

<160> NUMBER OF SEQ ID NOS: 51

<210> SEQ ID NO 1
<211> LENGTH: 367
<212> TYPE: PRT
<213> ORGANISM: Homo sapiens

<400> SEQUENCE: 1

```
Met Asn Ser Ser Pro Ala Gly Thr Pro Ser Pro Gln Pro Ser Arg Ala
1               5                   10                  15

Asn Gly Asn Ile Asn Leu Gly Pro Ser Ala Asn Pro Asn Ala Gln Pro
            20                  25                  30

Thr Asp Phe Asp Phe Leu Lys Val Ile Gly Lys Gly Asn Tyr Gly Lys
        35                  40                  45

Val Leu Leu Ala Lys Arg Lys Ser Asp Gly Ala Phe Tyr Ala Val Lys
    50                  55                  60

Val Leu Gln Lys Lys Ser Ile Leu Lys Lys Lys Glu Gln Ser His Ile
65                  70                  75                  80

Met Ala Glu Arg Ser Val Leu Leu Lys Asn Val Arg His Pro Phe Leu
                85                  90                  95

Val Gly Leu Arg Tyr Ser Phe Gln Thr Pro Glu Lys Leu Tyr Phe Val
            100                 105                 110

Leu Asp Tyr Val Asn Gly Gly Glu Leu Phe Phe His Leu Gln Arg Glu
        115                 120                 125

Arg Arg Phe Leu Glu Pro Arg Ala Arg Phe Tyr Ala Ala Glu Val Ala
    130                 135                 140

Ser Ala Ile Gly Tyr Leu His Ser Leu Asn Ile Ile Tyr Arg Asp Leu
145                 150                 155                 160
```

-continued

Lys Pro Glu Asn Ile Leu Leu Asp Cys Gln Gly His Val Val Leu Thr
                165                 170                 175

Asp Phe Gly Leu Cys Lys Glu Gly Val Glu Pro Glu Asp Thr Thr Ser
            180                 185                 190

Thr Phe Cys Gly Thr Pro Glu Tyr Leu Ala Pro Glu Val Leu Arg Lys
        195                 200                 205

Glu Pro Tyr Asp Arg Ala Val Asp Trp Trp Cys Leu Gly Ala Val Leu
    210                 215                 220

Tyr Glu Met Leu His Gly Leu Pro Pro Phe Tyr Ser Gln Asp Val Ser
225                 230                 235                 240

Gln Met Tyr Glu Asn Ile Leu His Gln Pro Leu Gln Ile Pro Gly Gly
                245                 250                 255

Arg Thr Val Ala Ala Cys Asp Leu Leu Gln Ser Leu Leu His Lys Asp
            260                 265                 270

Gln Arg Gln Arg Leu Gly Ser Lys Ala Asp Phe Leu Glu Ile Lys Asn
        275                 280                 285

His Val Phe Phe Ser Pro Ile Asn Trp Asp Asp Leu Tyr His Lys Arg
    290                 295                 300

Leu Thr Pro Pro Phe Asn Pro Asn Val Thr Gly Pro Ala Asp Leu Lys
305                 310                 315                 320

His Phe Asp Pro Glu Phe Thr Gln Glu Ala Val Ser Lys Ser Ile Gly
                325                 330                 335

Cys Thr Pro Asp Thr Val Ala Ser Ser Ser Gly Ala Ser Ser Ala Phe
            340                 345                 350

Leu Gly Phe Ser Tyr Ala Pro Glu Asp Asp Asp Ile Leu Asp Cys
        355                 360                 365

<210> SEQ ID NO 2
<211> LENGTH: 16
<212> TYPE: PRT
<213> ORGANISM: Artificial Sequence
<220> FEATURE:
<223> OTHER INFORMATION: synthetic construct

<400> SEQUENCE: 2

Asn Glu Glu His Asn Ser Thr Thr Ser Thr Phe Cys Gly Thr Pro Glu
1               5                   10                  15

<210> SEQ ID NO 3
<211> LENGTH: 367
<212> TYPE: PRT
<213> ORGANISM: Mus musculus

<400> SEQUENCE: 3

Met Ala Ser Ser Pro Val Gly Val Pro Ser Pro Gln Pro Ser Arg Ala
1               5                   10                  15

Asn Gly Asn Ile Asn Leu Gly Pro Ser Ala Asn Pro Asn Ala Arg Pro
                20                  25                  30

Thr Asp Phe Asp Phe Leu Lys Val Ile Gly Lys Gly Asn Tyr Gly Lys
            35                  40                  45

Val Leu Leu Ala Lys Arg Lys Ser Asp Gly Ala Phe Tyr Ala Val Lys
        50                  55                  60

Val Leu Gln Lys Lys Ser Ile Leu Lys Asn Lys Glu Gln Asn His Ile
65                  70                  75                  80

Met Ala Glu Arg Asn Val Leu Leu Lys Asn Val Arg His Pro Phe Leu
                85                  90                  95

Val Gly Leu Arg Tyr Ser Phe Gln Thr Pro Glu Lys Leu Tyr Phe Val

```
            100                 105                 110
Leu Asp Tyr Val Asn Gly Gly Glu Leu Phe His Leu Gln Arg Glu
        115                 120                 125
Arg Arg Phe Leu Glu Pro Arg Ala Arg Phe Tyr Thr Ala Glu Val Ala
    130                 135                 140
Ser Ala Ile Gly Tyr Leu His Ser Leu Asn Ile Ile Tyr Arg Asp Leu
145                 150                 155                 160
Lys Pro Glu Asn Ile Leu Leu Asp Cys Gln Gly His Val Val Leu Thr
                165                 170                 175
Asp Phe Gly Leu Cys Lys Glu Cys Val Glu Pro Glu Thr Thr Ser
        180                 185                 190
Thr Phe Cys Gly Thr Pro Glu Tyr Leu Ala Pro Glu Val Leu Arg Lys
        195                 200                 205
Glu Pro Tyr Asp Arg Ala Val Asp Trp Trp Cys Leu Gly Ala Val Leu
    210                 215                 220
Tyr Glu Met Leu His Gly Leu Pro Pro Phe Phe Asn Thr Asp Val Ala
225                 230                 235                 240
Gln Met Tyr Glu Asn Ile Leu His Gln Pro Leu Gln Ile Pro Gly Gly
                245                 250                 255
Arg Thr Val Ala Ala Cys Asp Leu Leu Gln Gly Leu Leu His Lys Asp
        260                 265                 270
Gln Arg Gln Arg Leu Gly Ser Lys Glu Asp Phe Leu Asp Ile Lys Asn
        275                 280                 285
His Met Phe Phe Ser Pro Ile Asn Trp Asp Asp Leu Tyr His Lys Arg
        290                 295                 300
Leu Thr Pro Pro Phe Asn Pro Asn Val Glu Gly Pro Ala Asp Leu Lys
305                 310                 315                 320
His Phe Asp Pro Glu Phe Thr Gln Glu Ala Val Ser Lys Ser Ile Gly
                325                 330                 335
Cys Thr Pro Asp Thr Val Ala Ser Ser Ser Gly Ala Ser Ser Ala Phe
                340                 345                 350
Leu Gly Phe Ser Tyr Ala Gln Asp Asp Asp Asp Ile Leu Asp Ser
        355                 360                 365

<210> SEQ ID NO 4
<211> LENGTH: 429
<212> TYPE: PRT
<213> ORGANISM: Homo sapiens

<400> SEQUENCE: 4

Met Ala Leu Lys Ile Pro Ala Lys Arg Ile Phe Gly Asp Asn Phe Asp
1               5                   10                  15
Pro Asp Phe Ile Lys Gln Arg Arg Ala Gly Leu Asn Glu Phe Ile Gln
                20                  25                  30
Asn Leu Val Arg Tyr Pro Glu Leu Tyr Asn His Pro Asp Val Arg Ala
            35                  40                  45
Phe Leu Gln Met Asp Ser Pro Lys His Gln Ser Asp Pro Ser Glu Asp
        50                  55                  60
Glu Asp Glu Arg Ser Ser Gln Lys Leu His Ser Thr Ser Gln Asn Ile
65                  70                  75                  80
Asn Leu Gly Pro Ser Gly Asn Pro His Ala Lys Pro Thr Asp Phe Asp
                85                  90                  95
Phe Leu Lys Val Ile Gly Lys Gly Ser Phe Gly Lys Val Leu Leu Ala
            100                 105                 110
```

-continued

```
Lys Arg Lys Leu Asp Gly Lys Phe Tyr Ala Val Lys Val Leu Gln Lys
            115                 120                 125

Lys Ile Val Leu Asn Arg Lys Glu Gln Lys His Ile Met Ala Glu Arg
130                 135                 140

Asn Val Leu Leu Lys Asn Val Lys His Pro Phe Leu Val Gly Leu His
145                 150                 155                 160

Tyr Ser Phe Gln Thr Thr Glu Lys Leu Tyr Phe Val Leu Asp Phe Val
                165                 170                 175

Asn Gly Gly Glu Leu Phe Phe His Leu Gln Arg Glu Arg Ser Phe Pro
            180                 185                 190

Glu His Arg Ala Arg Phe Tyr Ala Ala Glu Ile Ala Ser Ala Leu Gly
        195                 200                 205

Tyr Leu His Ser Ile Lys Ile Val Tyr Arg Asp Leu Lys Pro Glu Asn
    210                 215                 220

Ile Leu Leu Asp Ser Val Gly His Val Val Leu Thr Asp Phe Gly Leu
225                 230                 235                 240

Cys Lys Glu Gly Ile Ala Ile Ser Asp Thr Thr Thr Phe Cys Gly
                245                 250                 255

Thr Pro Glu Tyr Leu Ala Pro Glu Val Ile Arg Lys Gln Pro Tyr Asp
            260                 265                 270

Asn Thr Val Asp Trp Trp Cys Leu Gly Ala Val Leu Tyr Glu Met Leu
        275                 280                 285

Tyr Gly Leu Pro Pro Phe Tyr Cys Arg Asp Val Ala Glu Met Tyr Asp
    290                 295                 300

Asn Ile Leu His Lys Pro Leu Ser Leu Arg Pro Gly Val Ser Leu Thr
305                 310                 315                 320

Ala Trp Ser Ile Leu Glu Glu Leu Leu Glu Lys Asp Arg Gln Asn Arg
                325                 330                 335

Leu Gly Ala Lys Glu Asp Phe Leu Glu Ile Gln Asn His Pro Phe Phe
            340                 345                 350

Glu Ser Leu Ser Trp Ala Asp Leu Val Gln Lys Lys Ile Pro Pro Pro
        355                 360                 365

Phe Asn Pro Asn Val Ala Gly Pro Asp Asp Ile Arg Asn Phe Asp Thr
    370                 375                 380

Ala Phe Thr Glu Glu Thr Val Pro Tyr Ser Val Cys Val Ser Ser Asp
385                 390                 395                 400

Tyr Ser Ile Val Asn Ala Ser Val Leu Glu Ala Asp Asp Ala Phe Val
                405                 410                 415

Gly Phe Ser Tyr Ala Pro Pro Ser Glu Asp Leu Phe Leu
            420                 425
```

<210> SEQ ID NO 5
<211> LENGTH: 2146
<212> TYPE: DNA
<213> ORGANISM: Homo sapiens

<400> SEQUENCE: 5

```
atgggttcag actttatgcc ctgaaaagat ccttccagcc ctggccatct tggacttctg      60
gagctaccct ggctcacagg ggtcttgttg ccctgggtgt ccccagttct tgaaaagaat     120
cagcctggga gggccacaca cctgaccatc ccccttttatc ccttctgaga tgtttgttag     180
gaagtctggg tccaggggat atcatttctt gttccatcca tgcagggggtt gcttacctcg     240 ggtaggaaac cctcaggcgg tgcaggtgca acaggtaggg gaggatggag agggcagtgg     300
tgcctgaagc cctggatggg cggagctgac cccccaacac caactctatc atgcctgctc     360
```

-continued

```
ctccctgtcc ccccagagct gcctgatcat tgctacagaa tgaactctag cccagctggg      420
accccaagtc cacagccctc cagggccaat gggaacatca acctggggcc ttcagccaac      480
ccaaatgccc agcccacgga cttcgacttc tcaaagtca tcggcaaagg gaactacggg       540
aaggtcctac tggccaagcg caagtctgat ggggcgttct atgcagtgaa ggtactacag      600
aaaaagtcca tcttaaagaa gaaagagcag agccacatca tggcagagcg cagtgtgctt      660
ctgaagaacg tgcggcaccc cttcctcgtg ggcctgcgct actccttcca gacacctgag      720
aagctctact tcgtgctcga ctatgtcaac ggggagagc tcttcttcca cctgcagcgg       780
gagcgccggt tcctggagcc ccgggccagg ttctacgctg ctgaggtggc cagcgccatt      840
ggctacctgc actccctcaa catcatttac agggatctga accagagaa cattctcttg        900 gactgccagg gacacgtggt gctgacggat tttggcctct gcaaggaagg tgtagagcct      960
gaagacacca catccacatt ctgtggtacc cctgagtact tggcacctga agtgcttcgg     1020
aaagagcctt atgatcgagc agtggactgg tggtgcttgg gggcagtcct ctacgagatg     1080
ctccatggcc tgccgccctt ctacagccaa gatgtatccc agatgtatga gaacattctg     1140
caccagccgc tacagatccc cggaggccgg acagtggccg cctgtgacct cctgcaaagc     1200
cttctccaca aggaccagag gcagcggctg ggctccaaag cagactttct tgagattaag     1260
aaccatgtat tcttcagccc cataaactgg gatgacctgt accacaagag gctaactcca     1320
cccttcaacc caaatgtgac aggacctgct gacttgaagc attttgaccc agagttcacc     1380
caggaagctg tgtccaagtc cattggctgt acccctgaca ctgtggccag cagctctggg     1440
gcctcaagtg cattcctggg atttctctat gcgccagagg atgatgacat cttggattgc     1500
tagaagagaa ggacctgtga aactactgag gccagctggt attagtaagg aattaccttc     1560
agctgctagg aagagcgact caaactaaca atggcttcaa cgagaagcag gtttattttt     1620
tccagcacat aaaagaaaaa taatgtttcg gagtccagga ctggcaggac aggtcatcag     1680
atactcagag gctgtatctc tgccctgcca accttgacaa atggcttcca atgttaggtt     1740
tgctacaaga tggttactgg agctctagct gcctattttg tgtttaggga agggaaaatg     1800
gaggaagggg gagaagagca aagggcgctt ttaaagagct ttcccaaaag ctccccccaa     1860
tgacttttgc ttccatctca ctaaccaccc acccctacct ggaatggagg ctgggaaatg     1920
tggcttattt gctgggtacg tgactatccc taataacaaa ggggttttga ccctaagaca     1980
ttaggggaga atgttgggta ggcagccagc cctcttttac catagggcct cctggtgttt     2040
ggattttgat ctcaatgtgt aaaatgacag agatgtaaca agctcatagg gtatcaatat     2100
ctcttattgt tctatgttga aaaaaaaaaa aaaaaaaaa aaaaa                       2146
```

<210> SEQ ID NO 6
<211> LENGTH: 2404
<212> TYPE: DNA
<213> ORGANISM: Homo sapiens

<400> SEQUENCE: 6

```
ggtgtgctct tgagggatta aatgcaaaga gatcacacca tggactacaa ggaaagctgc       60
ccaagtgtaa gcattcccag ctccgatgaa cacagagaga aaagaagag gtttactgtt       120 tataaagttc tggtttcagt gggaagaagt gaatggtttg tcttcaggag atatgcagag      180
tttgataaac tttataacac tttaaaaaaa cagtttcctg ctatggccct gaagattcct      240
gccaagagaa tatttggtga taattttgat ccagatttta ttaaacaaag acgagcagga      300
```

-continued

```
ctaaacgaat tcattcagaa cctagttagg tatccagaac tttataacca tccagatgtc    360
agagcattcc ttcaaatgga cagtccaaaa caccagtcag atccatctga agatgaggat    420
gaaagaagtt ctcagaagct acactctacc tcacagaaca tcaacctggg accgtctgga    480
aatcctcatg ccaaaccaac tgactttgat ttcttaaaag ttattggaaa aggcagcttt    540
ggcaaggttc ttcttgcaaa acggaaactg gatggaaaat tttatgctgt caaagtgtta    600
cagaaaaaaa tagttctcaa cagaaaagag caaaaacata ttatgctgaa cgtaatgtg     660
ctcttgaaaa atgtgaaaca tccgtttttg gttggattgc attattcctt ccaaacaact    720
gaaaagcttt attttgttct ggattttgtt aatggagggg agcttttttt ccacttacaa    780
agagaacggt cctttcctga gcacagagct aggttttacg ctgctgaaat tgctagtgca    840
ttgggttact tacattccat caaaatagta tacagagact tgaaaccaga aaatattctt    900
ttggattcag taggacatgt tgtcttaaca gattttgggc tttgtaaaga aggaattgct    960
atttctgaca ccactaccac attttgtggg acaccagagt atcttgcacc tgaagtaatt   1020
agaaaacagc cctatgacaa tactgtagat tggtggtgcc ttgggctgt tctgtatgaa    1080
atgctgtatg gattgcctcc ttttttattgc cgagatgttg ctgaaatgta tgacaatatc   1140
cttcacaaac ccctaagttt gaggccagga gtgagtctta cagcctggtc cattctggaa   1200
gaactcctag aaaaagacag gcaaaatcga cttggtgcca aggaagactt tcttgaaatt   1260
cagaatcatc ctttttttga atcactcagc tgggctgacc ttgtacaaaa gaagattcca   1320
ccaccattta atcctaatgt ggctggacca atgatatca gaaactttga cacagcattt    1380
acagaagaaa cagttccata ttctgtgtgt gtatcttctg actattctat agtgaatgcc   1440
agtgtattgg aggcagatga tgcattcgtt ggtttctctt atgcacctcc ttcagaagac   1500
ttatttttgt gagcagtttg ccattcagaa accattgagc aaaataagtc tatagatggg   1560
actgaaactt ctatttgtgt gaatatattc aaatatgtat aactagtgcc tcatttttat   1620
atgtaatgat gaaaactatg aaaaaatgta ttttcttcta tgtgcaagaa aaatagggca   1680
tttcaaagag ctgttttgat taaaatttat attcttgttt aataagctta tttttaaaca   1740
atttaaaagc tattattctt agcattaacc tattttttaaa gaaaccttt ttgctattga    1800
ctgttttttc cctctaagtt tacactaaca tctacccaag atagactgtt ttttaacagt   1860
caatttcagt tcagctaaca tatattaata cctttgtaac tctttgctat ggcttttgtt   1920
atcacaccaa aactatgcaa ttggtacatg gttgtttaag aagaaaccgt attttttccat   1980
gataaatcac tgtttgaaat atttggttca tggtatgatc gaaatgtaaa agcataatta   2040
acacattggc tgctagttaa caattggaat aactttattc tgcagatcat ttaagaagta   2100
acaggccggg cgcggtggct cacgcctgta atcccagcac tttgggaggc tgaggcgggc   2160
agatcacctg aggtcaggag ttggagacca gcctgaccaa catggacaaa ccccgtctct   2220
actaaaaata caaaattggc cagggtgtgg tggcacatgcc tataatccca gctacttggg   2280
aggctaaggc aggagaatcg cttgaacccg ggaggcggag gttgcagtga gccgagatcg   2340
caccattgca ctcctgcctg ggcaacaaga gtgaaactcc atctccaaaa aaaaaaaaaa   2400
aaaa                                                                2404
```

<210> SEQ ID NO 7
<211> LENGTH: 1834
<212> TYPE: DNA
<213> ORGANISM: Homo sapiens

<400> SEQUENCE: 7

-continued

```
gaagagggca gagccgtgca tggggctgct ccccaggacc tgagcaggaa cctggagttt      60
tcagagctgc ctgatcattg ctacagaatg aactctagcc cagctgggac cccaagtcca     120
cagccctcca gggccaatgg aacatcaac ctggggcctt cagccaaccc aaatgcccag      180
cccacggact tcgacttcct caaagtcatc ggcaaaggga actacggaa ggtcctactg      240 gccaagcgca gtctgatgg ggcgttctat gcagtgaagg tactacagaa aaagtccatc      300
ttaaagaaga aagagcagag ccacatcatg gcagagcgca gtgtgcttct gaagaacgtg     360
cggcacccct cctcgtggg cctgcgctac tccttccaga cacctgagaa gctctacttc      420
gtgctcgact atgtcaacgg gggagagctc ttcttccacc tgcagcggga gcgccggttc     480
ctggagcccc gggccaggtt ctacgctgct gaggtggcca cgccattgg ctacctgcac      540 tccctcaaca tcatttacag ggatctgaaa ccagagaaca ttctcttgga ctgccaggga     600
cacgtggtgc tgacggattt tggcctctgc aaggaaggtg tagagcctga agacaccaca    660
tccacattct gtggtacccc tgagtacttg gcacctgaag tgcttcggaa agagccttat     720
gatcgagcag tggactggtg gtgcttgggg gcagtcctct acgagatgct ccatggcctg    780
ccgcccttct acagccaaga tgtatcccag atgtatgaga cattctgca ccagccgcta      840 cagatcccg gaggccggac agtggccgcc tgtgacctcc tgcaaagcct tctcccacaag     900 gaccagaggc agcggctggg ctccaaagca gactttcttg agattaagaa ccatgtattc     960
ttcagcccca taaactggga tgacctgtac cacaagaggc taactccacc cttcaaccca    1020
aatgtgacag gacctgctga cttgaagcat tttgacccag agttcaccca ggaagctgtg    1080
tccaagtcca ttggctgtac ccctgacact gtggccagca gctctgggc ctcaagtgca     1140 ttcctgggat tttcttatgc gccagaggat gatgacatct tggattgcta aagagaagg    1200 acctgtgaaa ctactgaggc cagctggtat tagtaaggaa ttaccttcag ctgctaggaa    1260
gagcgactca aactaacaat ggcttcaacg agaagcaggt ttatttttttc cagcacataa   1320 aagaaaaata atgtttcgga gtccaggact ggcaggacag gtcatcagat actcagaggc    1380
tgtatctctg ccctgccaac cttgacaaat ggcttccaat gttaggtttg ctacaagatg    1440
gttactggag ctctagctgc ctattttgtg tttagggaag ggaaaatgga ggaaagggga    1500
gaagagcaaa gggcgctttt aaagagcttt cccaaaagct cccccaatg acttttgctt     1560 ccatctcact aaccacccac ccctacctgg aatggaggct gggaaatgtg gcttatttgc    1620
tgggtacgtg actatcccta ataacaaagg ggttttgacc ctaagacatt aggggagaat    1680
gttgggtagg cagccagccc tcttttacca tagggcctcc tggtgtttgg attttgatct    1740
caatgtgtaa aatgacagag atgtaacaag ctcatagggt atcaatatct cttattgttc    1800
tatgttgaaa aaaaaaaaaa aaaaaaaaa aaaa                                 1834
```

<210> SEQ ID NO 8  
<211> LENGTH: 427  
<212> TYPE: PRT  
<213> ORGANISM: Homo sapiens

<400> SEQUENCE: 8

```
Met Gln Gly Leu Leu Thr Ser Gly Arg Lys Pro Ser Gly Gly Arg
1               5                   10                  15

Cys Thr Gly Arg Gly Gly Trp Arg Gly Gln Trp Cys Leu Lys Pro Trp
            20                  25                  30

Met Gly Gly Ala Asp Pro Pro Thr Pro Thr Leu Ser Cys Leu Leu Leu
        35                  40                  45
```

-continued

```
Pro Val Pro Pro Glu Leu Pro Asp His Cys Tyr Arg Met Asn Ser Ser
 50                  55                  60
Pro Ala Gly Thr Pro Ser Pro Gln Pro Ser Arg Ala Asn Gly Asn Ile
 65                  70                  75                  80
Asn Leu Gly Pro Ser Ala Asn Pro Asn Ala Gln Pro Thr Asp Phe Asp
                 85                  90                  95
Phe Leu Lys Val Ile Gly Lys Gly Asn Tyr Gly Lys Val Leu Leu Ala
            100                 105                 110
Lys Arg Lys Ser Asp Gly Ala Phe Tyr Ala Val Lys Val Leu Gln Lys
        115                 120                 125
Lys Ser Ile Leu Lys Lys Lys Glu Gln Ser His Ile Met Ala Glu Arg
    130                 135                 140
Ser Val Leu Leu Lys Asn Val Arg His Pro Phe Leu Val Gly Leu Arg
145                 150                 155                 160
Tyr Ser Phe Gln Thr Pro Glu Lys Leu Tyr Phe Val Leu Asp Tyr Val
                165                 170                 175
Asn Gly Gly Glu Leu Phe Phe His Leu Gln Arg Glu Arg Arg Phe Leu
            180                 185                 190
Glu Pro Arg Ala Arg Phe Tyr Ala Ala Glu Val Ala Ser Ala Ile Gly
        195                 200                 205
Tyr Leu His Ser Leu Asn Ile Ile Tyr Arg Asp Leu Lys Pro Glu Asn
    210                 215                 220
Ile Leu Leu Asp Cys Gln Gly His Val Val Leu Thr Asp Phe Gly Leu
225                 230                 235                 240
Cys Lys Glu Gly Val Glu Pro Glu Asp Thr Thr Ser Thr Phe Cys Gly
                245                 250                 255
Thr Pro Glu Tyr Leu Ala Pro Glu Val Leu Arg Lys Glu Pro Tyr Asp
            260                 265                 270
Arg Ala Val Asp Trp Trp Cys Leu Gly Ala Val Leu Tyr Glu Met Leu
        275                 280                 285
His Gly Leu Pro Pro Phe Tyr Ser Gln Asp Val Ser Gln Met Tyr Glu
    290                 295                 300
Asn Ile Leu His Gln Pro Leu Gln Ile Pro Gly Gly Arg Thr Val Ala
305                 310                 315                 320
Ala Cys Asp Leu Leu Gln Ser Leu Leu His Lys Asp Gln Arg Gln Arg
                325                 330                 335
Leu Gly Ser Lys Ala Asp Phe Leu Glu Ile Lys Asn His Val Phe Phe
            340                 345                 350
Ser Pro Ile Asn Trp Asp Asp Leu Tyr His Lys Arg Leu Thr Pro Pro
        355                 360                 365
Phe Asn Pro Asn Val Thr Gly Pro Ala Asp Leu Lys His Phe Asp Pro
    370                 375                 380
Glu Phe Thr Gln Glu Ala Val Ser Lys Ser Ile Gly Cys Thr Pro Asp
385                 390                 395                 400
Thr Val Ala Ser Ser Ser Gly Ala Ser Ser Ala Phe Leu Gly Phe Ser
                405                 410                 415
Tyr Ala Pro Glu Asp Asp Asp Ile Leu Asp Cys
            420                 425

<210> SEQ ID NO 9
<211> LENGTH: 73
<212> TYPE: DNA
<213> ORGANISM: Artificial Sequence
<220> FEATURE:
```

```
<223> OTHER INFORMATION: PCR PRIMER

<400> SEQUENCE: 9
acacggatcc gccaccatgt atccatatga tgttccagat tatgctacgg tgaaaactga    60
ggctgctaag ggc                                                       73

<210> SEQ ID NO 10
<211> LENGTH: 40
<212> TYPE: DNA
<213> ORGANISM: Artificial Sequence
<220> FEATURE:
<223> OTHER INFORMATION: PCR PRIMER

<400> SEQUENCE: 10
acacggtacc gtcgactcag aggaaagagt ccgtgggagg                          40

<210> SEQ ID NO 11
<211> LENGTH: 23
<212> TYPE: DNA
<213> ORGANISM: Artificial Sequence
<220> FEATURE:
<223> OTHER INFORMATION: PCR PRIMER

<400> SEQUENCE: 11
gatctcggat ccactaacgg tac                                            23

<210> SEQ ID NO 12
<211> LENGTH: 15
<212> TYPE: DNA
<213> ORGANISM: Artificial Sequence
<220> FEATURE:
<223> OTHER INFORMATION: PCR PRIMER

<400> SEQUENCE: 12
cgttagtgga tccga                                                     15

<210> SEQ ID NO 13
<211> LENGTH: 27
<212> TYPE: DNA
<213> ORGANISM: Artificial Sequence
<220> FEATURE:
<223> OTHER INFORMATION: PCR PRIMER

<400> SEQUENCE: 13
gctctggact tggggtccca gctgggc                                        27

<210> SEQ ID NO 14
<211> LENGTH: 27
<212> TYPE: DNA
<213> ORGANISM: Artificial Sequence
<220> FEATURE:
<223> OTHER INFORMATION: PCR PRIMER

<400> SEQUENCE: 14
gttgatgttc ccattggccc tggaggg                                        27

<210> SEQ ID NO 15
<211> LENGTH: 27
<212> TYPE: DNA
<213> ORGANISM: Artificial Sequence
<220> FEATURE:
<223> OTHER INFORMATION: Pcr Primer

<400> SEQUENCE: 15
gctgggcatt tgggttggct gaaggcc                                        27
```

```
<210> SEQ ID NO 16
<211> LENGTH: 24
<212> TYPE: DNA
<213> ORGANISM: Artificial Sequence
<220> FEATURE:
<223> OTHER INFORMATION: PCR PRIMER

<400> SEQUENCE: 16
aacatccgtt tttggttgga ttgc                                              24

<210> SEQ ID NO 17
<211> LENGTH: 20
<212> TYPE: DNA
<213> ORGANISM: Artificial Sequence
<220> FEATURE:
<223> OTHER INFORMATION: PCR PRIMER

<400> SEQUENCE: 17
gggtagatgt tagtgtaaac                                                   20

<210> SEQ ID NO 18
<211> LENGTH: 25
<212> TYPE: DNA
<213> ORGANISM: Artificial Sequence
<220> FEATURE:
<223> OTHER INFORMATION: PCR PRIMER

<400> SEQUENCE: 18
ataaagttct ggatacctaa ctagg                                             25

<210> SEQ ID NO 19
<211> LENGTH: 26
<212> TYPE: DNA
<213> ORGANISM: Artificial Sequence
<220> FEATURE:
<223> OTHER INFORMATION: PCR PRIMER

<400> SEQUENCE: 19
gaaggaatgc tctgacatct ggatgg                                            26

<210> SEQ ID NO 20
<211> LENGTH: 26
<212> TYPE: DNA
<213> ORGANISM: Artificial Sequence
<220> FEATURE:
<223> OTHER INFORMATION: PCR PRIMER

<400> SEQUENCE: 20
gatctgactg gtgttttgga ctgtcc                                            26

<210> SEQ ID NO 21
<211> LENGTH: 26
<212> TYPE: DNA
<213> ORGANISM: Artificial Sequence
<220> FEATURE:
<223> OTHER INFORMATION: PCR PRIMER

<400> SEQUENCE: 21
ggatccagct gcctgatcat tgctac                                            26

<210> SEQ ID NO 22
<211> LENGTH: 29
<212> TYPE: DNA
<213> ORGANISM: Artificial Sequence
<220> FEATURE:
```

<223> OTHER INFORMATION: PCR PRIMER

<400> SEQUENCE: 22
gcggccgcct agcaatccaa gatgtcatc                29

<210> SEQ ID NO 23
<211> LENGTH: 26
<212> TYPE: DNA
<213> ORGANISM: Artificial Sequence
<220> FEATURE:
<223> OTHER INFORMATION: PCR PRIMER

<400> SEQUENCE: 23
ggatcccagg ggttgcttac ctcggg                26

<210> SEQ ID NO 24
<211> LENGTH: 29
<212> TYPE: DNA
<213> ORGANISM: Artificial Sequence
<220> FEATURE:
<223> OTHER INFORMATION: PCR PRIMER

<400> SEQUENCE: 24
gcggccgcct agcaatccaa gatgtcatc                29

<210> SEQ ID NO 25
<211> LENGTH: 29
<212> TYPE: DNA
<213> ORGANISM: Artificial Sequence
<220> FEATURE:
<223> OTHER INFORMATION: PCR PRIMER

<400> SEQUENCE: 25
ggatccaagc cctgaagaag attcctgcc                29

<210> SEQ ID NO 26
<211> LENGTH: 29
<212> TYPE: DNA
<213> ORGANISM: Artificial Sequence
<220> FEATURE:
<223> OTHER INFORMATION: PCR PRIMER

<400> SEQUENCE: 26
ggatccaagc cctgaagaag attcctgcc                29

<210> SEQ ID NO 27
<211> LENGTH: 26
<212> TYPE: DNA
<213> ORGANISM: Artificial Sequence
<220> FEATURE:
<223> OTHER INFORMATION: PCR PRIMER

<400> SEQUENCE: 27
gcggccgctc acaaaaataa gtcttc                26

<210> SEQ ID NO 28
<211> LENGTH: 26
<212> TYPE: DNA
<213> ORGANISM: Artificial Sequence
<220> FEATURE:
<223> OTHER INFORMATION: PCR PRIMER

<400> SEQUENCE: 28
ggatcctgga cagtccaaaa caccag                26

<210> SEQ ID NO 29
<211> LENGTH: 26
<212> TYPE: DNA
<213> ORGANISM: Artificial Sequence
<220> FEATURE:
<223> OTHER INFORMATION: PCR PRIMER

<400> SEQUENCE: 29
gcggccgctc acaaaaataa gtcttc                                          26

<210> SEQ ID NO 30
<211> LENGTH: 11
<212> TYPE: PRT
<213> ORGANISM: Artificial Sequence
<220> FEATURE:
<223> OTHER INFORMATION: synthetic construct

<400> SEQUENCE: 30

Gly Arg Pro Arg Thr Ser Ser Phe Ala Glu Gly
1               5                   10

<210> SEQ ID NO 31
<211> LENGTH: 6
<212> TYPE: PRT
<213> ORGANISM: Artificial Sequence
<220> FEATURE:
<223> OTHER INFORMATION: synthetic construct

<400> SEQUENCE: 31

Arg Pro Arg Thr Ser Ser
1               5

<210> SEQ ID NO 32
<211> LENGTH: 7
<212> TYPE: PRT
<213> ORGANISM: Artificial Sequence
<220> FEATURE:
<223> OTHER INFORMATION: synthetic construct

<400> SEQUENCE: 32

Arg Pro Arg Thr Ser Ala Phe
1               5

<210> SEQ ID NO 33
<211> LENGTH: 6
<212> TYPE: PRT
<213> ORGANISM: Artificial Sequence
<220> FEATURE:
<223> OTHER INFORMATION: synthetic construct

<400> SEQUENCE: 33

Pro Arg Thr Ser Ser Phe
1               5

<210> SEQ ID NO 34
<211> LENGTH: 6
<212> TYPE: PRT
<213> ORGANISM: Artificial Sequence
<220> FEATURE:
<223> OTHER INFORMATION: synthetic construct

<400> SEQUENCE: 34

Arg Pro Arg Thr Ser Ser
1               5

<210> SEQ ID NO 35
<211> LENGTH: 7

```
<212> TYPE: PRT
<213> ORGANISM: Artificial Sequence
<220> FEATURE:
<223> OTHER INFORMATION: synthetic construct

<400> SEQUENCE: 35

Arg Pro Arg Thr Ser Thr Phe
1               5

<210> SEQ ID NO 36
<211> LENGTH: 7
<212> TYPE: PRT
<213> ORGANISM: Artificial Sequence
<220> FEATURE:
<223> OTHER INFORMATION: synthetic construct

<400> SEQUENCE: 36

Arg Pro Arg Ala Ala Thr Phe
1               5

<210> SEQ ID NO 37
<211> LENGTH: 7
<212> TYPE: PRT
<213> ORGANISM: Artificial Sequence
<220> FEATURE:
<223> OTHER INFORMATION: synthetic construct

<400> SEQUENCE: 37

Lys Pro Arg Thr Ser Ser Phe
1               5

<210> SEQ ID NO 38
<211> LENGTH: 7
<212> TYPE: PRT
<213> ORGANISM: Artificial Sequence
<220> FEATURE:
<223> OTHER INFORMATION: synthetic construct

<400> SEQUENCE: 38

Arg Pro Lys Thr Ser Ser Phe
1               5

<210> SEQ ID NO 39
<211> LENGTH: 7
<212> TYPE: PRT
<213> ORGANISM: Artificial Sequence
<220> FEATURE:
<223> OTHER INFORMATION: synthetic construct

<400> SEQUENCE: 39

Arg Pro Arg Thr Ser Ser Phe
1               5

<210> SEQ ID NO 40
<211> LENGTH: 7
<212> TYPE: PRT
<213> ORGANISM: Artificial Sequence
<220> FEATURE:
<223> OTHER INFORMATION: synthetic construct

<400> SEQUENCE: 40

Arg Pro Arg Thr Ser Ser Leu
1               5

<210> SEQ ID NO 41
<211> LENGTH: 7
<212> TYPE: PRT
```

```
<213> ORGANISM: Artificial Sequence
<220> FEATURE:
<223> OTHER INFORMATION: synthetic construct

<400> SEQUENCE: 41

Arg Pro Arg Thr Ser Ser Val
1               5

<210> SEQ ID NO 42
<211> LENGTH: 7
<212> TYPE: PRT
<213> ORGANISM: Artificial Sequence
<220> FEATURE:
<223> OTHER INFORMATION: synthetic construct

<400> SEQUENCE: 42

Arg Pro Arg Thr Ser Ser Ala
1               5

<210> SEQ ID NO 43
<211> LENGTH: 7
<212> TYPE: PRT
<213> ORGANISM: Artificial Sequence
<220> FEATURE:
<223> OTHER INFORMATION: synthetic construct

<400> SEQUENCE: 43

Arg Pro Arg Thr Ser Ser Lys
1               5

<210> SEQ ID NO 44
<211> LENGTH: 7
<212> TYPE: PRT
<213> ORGANISM: Artificial Sequence
<220> FEATURE:
<223> OTHER INFORMATION: synthetic construct

<400> SEQUENCE: 44

Arg Pro Arg Thr Ser Ser Glu
1               5

<210> SEQ ID NO 45
<211> LENGTH: 6
<212> TYPE: PRT
<213> ORGANISM: Unknown
<220> FEATURE:
<223> OTHER INFORMATION: Consensus sequence from mammalian protein
      kinase, for example human, rat or mouse.
<220> FEATURE:
<221> NAME/KEY: MISC_FEATURE
<222> LOCATION: (2)..(3)
<223> OTHER INFORMATION: residues 2 and 3 are any amino acid
<220> FEATURE:
<221> NAME/KEY: MISC_FEATURE
<222> LOCATION: (4)..(4)
<223> OTHER INFORMATION: F or Y
<220> FEATURE:
<221> NAME/KEY: MISC_FEATURE
<222> LOCATION: (5)..(5)
<223> OTHER INFORMATION: S or T
<220> FEATURE:
<221> NAME/KEY: MISC_FEATURE
<222> LOCATION: (6)..(6)
<223> OTHER INFORMATION: F or Y

<400> SEQUENCE: 45

Phe Xaa Xaa Xaa Xaa Xaa
1               5
```

```
<210> SEQ ID NO 46
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (4)..(5)
<223> OTHER INFORMATION: any amino acid
<220> FEATURE:
<221> NAME/KEY: MISC_FEATURE
<222> LOCATION: (6)..(6)
<223> OTHER INFORMATION: S or T

<400> SEQUENCE: 46

Arg Xaa Arg Xaa Xaa Xaa
1               5

<210> SEQ ID NO 47
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (4)..(5)
<223> OTHER INFORMATION: any amino acid
<220> FEATURE:
<221> NAME/KEY: MISC_FEATURE
<222> LOCATION: (6)..(6)
<223> OTHER INFORMATION: S or T
<220> FEATURE:
<221> NAME/KEY: MISC_FEATURE
<222> LOCATION: (7)..(7)
<223> OTHER INFORMATION: amino acid is preferably hydrophobic

<400> SEQUENCE: 47

Arg Xaa Arg Xaa Xaa Xaa Xaa
1               5

<210> SEQ ID NO 48
<211> LENGTH: 13
<212> TYPE: PRT
<213> ORGANISM: Unknown
<220> FEATURE:
<223> OTHER INFORMATION: Consensus sequence from mammalian protein
      kinase, for example human, rat or mouse.
<220> FEATURE:
<221> NAME/KEY: MISC_FEATURE
<222> LOCATION: (1)..(1)
<223> OTHER INFORMATION: basic residue
<220> FEATURE:
<221> NAME/KEY: MISC_FEATURE
<222> LOCATION: (7)..(7)
<223> OTHER INFORMATION: P or I
<220> FEATURE:
<221> NAME/KEY: MISC_FEATURE
<222> LOCATION: (8)..(8)
<223> OTHER INFORMATION: D or E
<220> FEATURE:
<221> NAME/KEY: MISC_FEATURE
<222> LOCATION: (10)..(10)
<223> OTHER INFORMATION: L, I, or M

<400> SEQUENCE: 48
```

```
Xaa Thr Phe Cys Gly Thr Xaa Xaa Tyr Xaa Ala Pro Glu
1               5                   10

<210> SEQ ID NO 49
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: R or K
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: any amino acid, preferably R
<220> FEATURE:
<221> NAME/KEY: MISC_FEATURE
<222> LOCATION: (4)..(5)
<223> OTHER INFORMATION: any amino acid
<220> FEATURE:
<221> NAME/KEY: MISC_FEATURE
<222> LOCATION: (6)..(6)
<223> OTHER INFORMATION: S or T
<220> FEATURE:
<221> NAME/KEY: MISC_FEATURE
<222> LOCATION: (7)..(7)
<223> OTHER INFORMATION: any amino acid, preferably hydrophobic

<400> SEQUENCE: 49

Xaa Xaa Xaa Xaa Xaa Xaa Xaa
1               5

<210> SEQ ID NO 50
<211> LENGTH: 10
<212> TYPE: PRT
<213> ORGANISM: Artificial Sequence
<220> FEATURE:
<223> OTHER INFORMATION: synthetic construct

<400> SEQUENCE: 50

Ser Ile Gly Cys Thr Pro Asp Thr Val Ala
1               5                   10

<210> SEQ ID NO 51
<211> LENGTH: 10
<212> TYPE: PRT
<213> ORGANISM: Artificial Sequence
<220> FEATURE:
<223> OTHER INFORMATION: synthetic construct

<400> SEQUENCE: 51

Thr Phe Cys Gly Thr Pro Glu Thr Leu Ala
1               5                   10
```